(12) United States Patent
Boggs et al.

(10) Patent No.: US 7,622,494 B2
(45) Date of Patent: Nov. 24, 2009

(54) CHEMICAL COMPOUNDS

(75) Inventors: Sharon Davis Boggs, Durham, NC (US); John G Catalano, Durham, NC (US); Kristjan S Gudmundsson, Durham, NC (US); Leah D'Aurora Richardson, Durham, NC (US); Paul Richard Sebahar, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 237 days.

(21) Appl. No.: 10/569,524

(22) PCT Filed: Jun. 7, 2004

(86) PCT No.: PCT/US2004/017982

§ 371 (c)(1), (2), (4) Date: Feb. 24, 2006

(87) PCT Pub. No.: WO2005/023245

PCT Pub. Date: Mar. 17, 2005

(65) Prior Publication Data

US 2006/0281804 A1    Dec. 14, 2006

Related U.S. Application Data

(60) Provisional application No. 60/497,845, filed on Aug. 26, 2003.

(51) Int. Cl.
*A61K 31/403* (2006.01)
*C07D 209/82* (2006.01)

(52) U.S. Cl. .................................... 514/411; 548/439
(58) Field of Classification Search ................ 514/411; 548/439

See application file for complete search history.

(56) References Cited

U.S. PATENT DOCUMENTS

| 7,351,733 B2 | 4/2008 | Boggs et al. |
| 2003/0139609 A1 | 7/2003 | Xing et al. |
| 2004/0006054 A1 | 1/2004 | Xing et al. |
| 2004/0009613 A1 | 1/2004 | Ott et al. |
| 2005/0287177 A1 | 12/2005 | Goodson et al. |

FOREIGN PATENT DOCUMENTS

WO          01/43741 A1    6/2001

OTHER PUBLICATIONS

Smith, M. B. Organic Synthesis, McGraw-Hill, Inc. 1994, Chapter 1.*
Xing, Chenguo et al., "Design of Cancer-Specific Antitumor Agents Based on Aziridinylcyclopent[b]indoloquinones," Journal of Medicinal Chemistry, vol. 43, No. 3, pp. 457-466, 2000.
Skibo, Edward B., et al., "Aziridinyl Quinone Antitumor Agents Based on Indoles and Cyclopent[b]indoles: Structure-Activity Relationships for Cytotoxicity and Antitumor Activity," Journal of Medicinal Chemistry, vol. 44, No. 22, pp. 3545-3562, 2001.

* cited by examiner

*Primary Examiner*—Rebecca L Anderson
*Assistant Examiner*—Jason Nolan
(74) *Attorney, Agent, or Firm*—Karen L. Prus

(57) ABSTRACT

The present invention relates to compounds that are useful in the treatment of human papillomaviruses, and also to the methods for the making and use of such compounds.

25 Claims, No Drawings

CHEMICAL COMPOUNDS

This application is filed pursuant to 35 U.S.C. § 371 as a United States National Phase Application of International Application No. PCT/US2004/017982 filed Jun. 7,2004, which claims priority from U.S. 60/497,845 filed Aug. 26, 2003.

FIELD OF THE INVENTION

The present invention relates to novel compounds that are useful in the treatment of human papillomavirus infections, and also to the methods for the making and use of such compounds.

BACKGROUND OF THE INVENTION

Human Papillomaviruses (HPVs) are small nonenveloped DNA viruses involved in many conditions and diseases. For example HPVs cause a wide variety of benign and pre-malignant tumors.

HPV is spread by direct contact. HPVs may be divided into two categories: cutaneous and mucosal. The cutaneous HPVs cause warts on hands and feet, such as common, plantar, filiform, or flat warts. The mucosal HPV types infect the anogenital region and the oral cavity. Approximately 100 different types of HPV have been characterized to date. Approximately 40 HPV types specifically infect the genital and oral mucosa.

Mucosal HPVs are most frequently sexually transmitted and, with an incidence roughly twice that of herpes simplex virus infection, HPVs are considered one of the most common sexually transmitted diseases (STDs) throughout the world.

Infection with the human papillomavirus (HPV) may not cause any symptoms and does not always produce visible genital warts. When symptoms do develop, they usually occur 2 to 3 months after infection with the virus. Symptoms have been known to develop, however, from 3 weeks to many years after infection occurs. As such, HPV may be spread unknowingly.

More than 25 HPV types that are implicated in anogenital diseases are broadly classified as either low risk or high risk. Low risk HPVs, such as HPV-6 and HPV-11, are the etiological cause of genital warts (condyloma acuminata). High risk HPVs, such as HPV-16, 18, 31, 33, 35, 39, 45, 51, 52, 56, 58, 59, and 68, may not produce visible genital warts. Rather the high-risk viral types may be identified by DNA testing. High risk HPVs such as HPV-16 and HPV-18 may be found on Pap screening tests and be related to precancerous cervical cell change, cervical dysplasia, and cervical cancer. In fact, high-risk HPV types, such as 16, 18, 31, 33, and 35, are strongly associated with precancerous and cancerous changes of the cervix. Most cervical cancers (about 90%). contain one of these high-risk types. High risk HPV infection creates a life-time risk of invasive cancer in the range of 5-10% for untreated infection.

In addition to cervical cancer, high risk HPVs are associated with a number of anal and perianal cancers.

Current treatments for genital warts and cervical dysplasia include physical removal such as cryotherapy, electrosurgery, and surgical excision. Currently, there are no effective antiviral treatments for HPV infection.

SUMMARY OF THE INVENTION

The present invention includes a method for the treatment or prophylaxis of conditions or disorders due to HPV infection comprising the administration of a compound of formula (I):

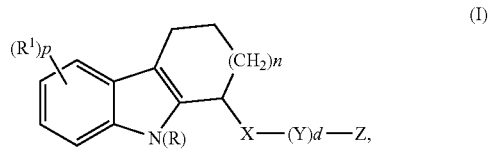

wherein:
n is 0, 1, or 2;
R is hydrogen or alkyl;
X is $NR^2$, O, or $S(O)_m$;
each $R^1$ is the same or different and is independently selected from the group consisting of hydrogen, halogen, haloalkyl, alkyl, alkenyl, alkynyl, cycloalkyl, cycloalkenyl, $-R^{10}$cycloalkyl, Ay, $-NHR^{10}$Ay, Het, $-NHHet$, $-NHR^{10}$Het, $OR^2$, $-OAy$, $-OHet$, $-R^{10}OR^2$, $-NR^2R^3$, $-NR^2Ay$, $-R^{10}NR^2R^3$, $-R^{10}NR^2Ay$, $-R^{10}C(O)R^2$, $-C(O)R^2$, $-CO_2R^2$, $-R^{10}CO_2R^2$, $-C(O)NR^2R^3$, $-C(O)Ay$, $-C(O)NR^2Ay$, $-C(O)Het$, $-C(O)NHR^{10}Het$, $-R^{10}C(O)NR^2R^3$, $-C(S)NR^2R^3$, $-R^{10}C(S)NR^2R^3$, $-R^{10}NHC(NH)NR^2R^3$, $-C(NH)NR^2R^3$, $-R^{10}C(NH)NR^2R^3$, $-S(O)_2NR^2R^3$, $-S(O)_2NR^2Ay$, $-R^{10}SO_2NHCOR^2$, $-R^{10}SO_2NR^2R^3$, $-R^{10}SO_2R^2$, $-S(O)_mR^2$, cyano, nitro, or azido;
Y is optionally substituted alkylene, optionally substituted cycloalkylene, optionally substituted alkenylene, optionally substituted cycloalkenylene, or optionally substituted alkynylene;
d is 0 or 1;
Z is $-R^2$, $-OR^2$, $-C(O)R^2$, $-C(O)_2R^2$, $-S(O)_mR^2_1-$ $C(O)NR^2R^3$-Het, or -Ay, provided when d is 0, then Z is not -Het or -Ay;
each m independently is 0, 1 or 2;
each $R^{10}$ is the same or different and is independently selected from alkylene, cycloalkylene, alkenylene, cycloalkenylene, and alkynylene;
p is selected from 0, 1, 2, 3, or 4;
each of $R^2$ and $R^3$ are the same or different and are independently selected from the group consisting of hydrogen, alkyl, alkenyl, alkynyl, cycloalkyl, cycloalkenyl, -$R^{10}$cycloalkyl, $-R^{10}OH$, $-R^{10}(OR^{10})_w$, and $-R^{10}NR^5R^6$;
w is 1-10;
each of $R^5$ and $R^6$ are the same or different and are independently selected from the group consisting of alkyl, cycloalkyl, alkenyl, cycloalkenyl, and alkynyl;
Ay represents an optionally substituted aryl group;
Het represents an optionally substituted 5- or 6-membered heterocyclyl or heteroaryl group;
including administration of pharmaceutically acceptable salts, solvates, and physiologically functional derivatives thereof.

In one embodiment, when d is 1, preferably Y is optionally substituted alkylene, namely optionally substituted with alkyl, dialkyl, or aryl. More preferably Y is methylene substituted with methyl, dimethyl, or optionally substituted phenyl.

In another embodiment, when d is 1, preferably Y is optionally substituted cycloalkylene. More preferably Y is indane.

Preferably when Ay is a substituted aryl, said aryl is substituted with alkyl, alkoxy, halogen, haloalkyl, alkylamine, nitro, or cyano. Preferably when p is 1, $R^1$ is halogen. More preferably $R^1$ is bromo or chloro.

Preferably n is 1.

Preferably X is —NH.

Preferably Z is -Ay. More preferably -Ay is phenyl.

In one embodiment p is 1, $R^1$ is halogen, n is 1, X is NH, $(Y)_d$ is substituted alkylene, and Z is aryl. More preferably $R^1$ is bromo or chloro and is substituted para to the depicted N atom, said alkylene is substituted with alkyl, and said aryl is phenyl. More preferably alkyl is methyl.

In one embodiment p is 1, $R^1$ is halogen, n is 1, X is NH, $(Y)_d$ is cycloalkylene, and Z is $R^2$. More preferably $R^1$ is bromo or chloro and is substituted para to the depicted N atom, $R^2$ is hydrogen, and $(Y)_d$ is indane.

Preferred compounds of the present invention include:

N-Benzyl-2,3,4,9-tetrahydrocarbazole-1-amine hydrochloride salt

N-(4-Methoxybenzyl)-2,3,4,9-tetrahydro-1H-carbazol-1-amine hydrochloride salt

N-(2-Phenylethyl)-2,3,4,9-tetrahydro-1H-carbazol-1-amine hydrochloride salt

N-[(1R)-1-Phenylethyl]-2,3,4,9-tetrahydro-1H-carbazol-1-amine hydrochloride salt N-Cyclohexyl-2,3,4,9-tetrahydro-1H-carbazol-1-amine hydrochloride salt N-(2,3-Dihydro-1H-inden-2-yl)-2,3,4,9-tetrahydro-1H-carbazol-1-amine hydrochloride salt N-Propyl-2,3,4,9-tetrahydro-1H-carbazol-1-amine hydrochloride salt N-(2-Methoxyethyl)-2,3,4,9-tetrahydro-1H-carbazol-1-amine hydrochloride salt (2R)-2-Phenyl-2-(2,3,4,9-tetrahydro-1H-carbazol-1-ylamino)ethanol hydrochloride salt N-[(1S)-1-Methyl-3-phenylpropyl]-2,3,4,9-tetrahydro-1H-carbazol-1-aminehydrochloride salt N-(1,3-Benzodioxol-5-ylmethyl)-2,3,4,9-tetrahydro-1H-carbazol-1-amine hydrochloride salt 6-Bromo-N-(2-phenylethyl)-2,3,4,9-tetrahydro-1H-carbazol-1-amine hydrochloride salt (1R)-6-Bromo-N-(2,3-dihydro-1H-inden-2-yl)-2,3,4,9-tetrahydro-1H-carbazol-1-amine hydrochloride salt (1S)-6-Bromo-N-(2,3-dihydro-1H-inden-2-yl)-2,3,4,9-tetrahydro-1H-carbazol-1-amine hydrochloride salt N-Benzyl-6-bromo-2,3,4,9-tetrahydro-1H-carbazol-1-amine hydrochloride salt 6-Bromo-N-[(1R)-1-phenylethyl]-2,3,4,9-tetrahydro-1H-carbazol-1-amine hydrochloride salt (1R)-6-bromo-N-[(1R)-1-phenylethyl]-2,3,4,9-tetrahydro-1H-carbazol-1-amine hydrochloride salt (1S)-6-Bromo-N-[(1R)-1-phenylethyl]-2,3,4,9-tetrahydro-1H-carbazol-1-amine hydrochloride salt 6-Bromo-N-(1-methyl-1-phenylethyl)-2,3,4,9-tetrahydro-1H-carbazol-1-amine hydrochloride salt 6-Bromo-N-[(1S)-1-phenylethyl]-2,3,4,9-tetrahydro-1H-carbazol-1-amine hydrochloride salt (1S)-6-Bromo-N-[(1S)-1-phenylethyl]-2,3,4,9-tetrahydro-1H-carbazol-1-amine hydrochloride salt (1R)-6-Bromo-N-[(1S)-1-phenylethyl]-2,3,4,9-tetrahydro-1H-carbazol-1-amine hydrochloride salt 6-Bromo-N-methyl-N-(2-phenylethyl)-2,3,4,9-tetrahydro-1H-carbazol-1-amine hydrochloride salt 6-Bromo-9-methyl-N-(2-phenylethyl)-2,3,4,9-tetrahydro-1H-carbazol-1-amine hydrochloride salt 6-Bromo-N-[(2R)-2-phenylpropyl]-2,3,4,9-tetrahydro-1H-carbazol-1-amine hydrochloride salt 6-Methyl-N-(2-phenylethyl)-2,3,4,9-tetrahydro-1H-carbazol-1-amine hydrochloride salt N-(2,3-Dihydro-1H-inden-2-yl)-6-methyl-2,3,4,9-tetrahydro-1H-carbazol-1-amine hydrochloride salt 6-Methyl-N-[(1R)-1-phenylethyl]-2,3,4,9-tetrahydro-1H-carbazol-1-amine hydrochloride salt (1R)-6-Methyl-N-[(1R)-1-phenylethyl]-2,3,4,9-tetrahydro-1H-carbazol-1-amine hydrochloride salt (1S)-6-Methyl-N-[(1R)-1-phenylethyl]-2,3,4,9-tetrahydro-1H-carbazol-1-amine hydrochloride salt 6-Methyl-N-[(1S)-1-phenylethyl]-2,3,4,9-tetrahydro-1H-carbazol-1-amine hydrochloride salt (1S)-6-Methyl-N-[(1S)-1-phenylethyl]-2,3,4,9-tetrahydro-1H-carbazol-1-amine hydrochloride salt (1R)-6-Methyl-N-[(1S)-1-phenylethyl]-2,3,4,9-tetrahydro-1H-carbazol-1-amine hydrochloride salt N-Benzyl-6-nitro-2,3,4,9-tetrahydro-1H-carbazol-1-amine hydrochloride salt 6-Nitro-N-[(1R)-1-phenylethyl]-2,3,4,9-tetrahydro-1H-carbazol-1-amine hydrochloride salt 7-Bromo-N-(2-phenylethyl)-1,2,3,4-tetrahydrocyclopenta[b]indol-3-amine hydrochloride salt (3R)-7-Bromo-N-[(1R)-1-phenylethyl]-1,2,3,4-tetrahydrocyclopenta[b]indol-3-amine hydrochloride salt (3S)-7-Bromo-N-[(1R)-1-phenylethyl]-1,2,3,4-tetrahydrocyclopenta[b]indol-3-amine hydrochloride salt N-Benzyl-6-methoxy-2,3,4,9-tetrahydro-1H-carbazol-1-amine hydrochloride salt N-Benzyl-2-bromo-5,6,7,8,9,10-hexahydrocyclohepta[b]indol-6-amine hydrochloride 2-Bromo-N-[(1R)-1-phenylethyl]-5,6,7,8,9,10-hexahydrocyclohepta[b]indol-6-amine hydrochloride 2-Bromo-N-(2-phenylethyl)-5,6,7,8,9,10-hexahydrocyclohepta[b]indol-6-amine hydrochloride 6-Bromo-N-(4-fluorobenzyl)-2,3,4,9-tetrahydro-1H-carbazol-1-amine hydrochloride N-Benzyl-6-(trifluoromethyl)-2,3,4,9-tetrahydro-1H-carbazol-1-amine hydrochloride N-[(1R)-1-Phenylethyl]-6-(trifluoromethyl)-2,3,4,9-tetrahydro-1H-carbazol-1-amine hydrochloride N-Benzhydryl-6-bromo-2,3,4,9-tetrahydro-1H-carbazol-1-amine hydrochloride N-Benzyl-7-bromo-2,3,4,9-tetrahydro-1H-carbazol-1-amine hydrochloride 7-Bromo-N-[(1R)-1-phenylethyl]-2,3,4,9-tetrahydro-1H-carbazol-1-amine hydrochloride 7-Bromo-N-(2,3-dihydro-1H-inden-2-yl)-2,3,4,9-tetrahydro-1H-carbazol-1-amine hydrochloride 6-Bromo-1-[(phenylmethyl)oxy]-2,3,4,9-tetrahydro-1H-carbazole N-(6-Bromo-2,3,4,9-tetrahydro-1H-carbazol-1-yl)-N'-isopropylurea Methyl 6-bromo-2,3,4,9-tetrahydro-1H-carbazol-1-ylcarbamate N-(6-Bromo-2,3,4,9-tetrahydro-1H-carbazol-1-yl)acetamide N-(6-Bromo-2,3,4,9-tetrahydro-1H-carbazol-1-yl)cyclohexanecarboxamide N-(6-Bromo-2,3,4,9-tetrahydro-1H-carbazol-1-yl)methanesulfonamide N-(6-Bromo-2,3,4,9-tetrahydro-1H-carbazol-1-yl)urea; and N-Benzyl-8-bromo-2,3,4,9-tetrahydro-1H-carbazol-1-amine hydrochloride.

More preferred compounds of the present invention include:

N-Benzyl-2,3,4,9-tetrahydrocarbazole-1-amine hydrochloride salt
N-(4-Methoxybenzyl)-2,3,4,9-tetrahydro-1H-carbazol-1-amine hydrochloride salt
N-(2-Phenylethyl)-2,3,4,9-tetrahydro-1H-carbazol-1-amine hydrochloride salt
N-(2,3-Dihydro-1H-inden-2-yl)-2,3,4,9-tetrahydro-1H-carbazol-1-amine hydrochloride salt
N-[(1S)-1-Methyl-3-phenylpropyl]-2,3,4,9-tetrahydro-1H-carbazol-1-aminehydrochloride salt
N-(1,3-Benzodioxol-5-ylmethyl)-2,3,4,9-tetrahydro-1H-carbazol-1-amine hydrochloride salt
6-Bromo-N-(2-phenylethyl)-2,3,4,9-tetrahydro-1H-carbazol-1-amine hydrochloride salt
(1R)-6-Bromo-N-(2,3-dihydro-1H-inden-2-yl)-2,3,4,9-tetrahydro-1H-carbazol-1-amine hydrochloride salt
(1S)-6-Bromo-N-(2,3-dihydro-1H-inden-2-yl)-2,3,4,9-tetrahydro-1H-carbazol-1-amine hydrochloride salt
N-Benzyl-6-bromo-2,3,4,9-tetrahydro-1H-carbazol-1-amine hydrochloride salt
6-Bromo-N-[(1R)-1-phenylethyl]-2,3,4,9-tetrahydro-1H-carbazol-1-amine hydrochloride salt
(1R)-6-bromo-N-[(1R)-1-phenylethyl]-2,3,4,9-tetrahydro-1H-carbazol-1-amine hydrochloride salt
(1S)-6-Bromo-N-[(1R)-1-phenylethyl]-2,3,4,9-tetrahydro-1H-carbazol-1-amine hydrochloride salt
6-Bromo-N-(1-methyl-1-phenylethyl)-2,3,4,9-tetrahydro-1H-carbazol-1-amine hydrochloride salt
6-Bromo-N-[(1S)-1-phenylethyl]-2,3,4,9-tetrahydro-1H-carbazol-1-amine hydrochloride salt
(1S)-6-Bromo-N-[(1S)-1-phenylethyl]-2,3,4,9-tetrahydro-1H-carbazol-1-amine hydrochloride salt
(1R)-6-Bromo-N-[(1S)-1-phenylethyl]-2,3,4,9-tetrahydro-1H-carbazol-1-amine hydrochloride salt
6-Bromo-N-methyl-N-(2-phenylethyl)-2,3,4,9-tetrahydro-1H-carbazol-1-amine hydrochloride salt
6-Bromo-N-[(2R)-2-phenylpropyl]-2,3,4,9-tetrahydro-1H-carbazol-1-amine hydrochloride salt
6-Methyl-N-(2-phenylethyl)-2,3,4,9-tetrahydro-1H-carbazol-1-amine hydrochloride salt
N-(2,3-Dihydro-1H-inden-2-yl)-6-methyl-2,3,4,9-tetrahydro-1H-carbazol-1-amine hydrochloride salt
6-Methyl-N-[(1R)-1-phenylethyl]-2,3,4,9-tetrahydro-1H-carbazol-1-amine hydrochloride salt
(1R)-6-Methyl-N-[(1R)-1-phenylethyl]-2,3,4,9-tetrahydro-1H-carbazol-1-amine hydrochloride salt
(1S)-6-Methyl-N-[(1R)-1-phenylethyl]-2,3,4,9-tetrahydro-1H-carbazol-1-amine hydrochloride salt
6-Methyl-N-[(1S)-1-phenylethyl]-2,3,4,9-tetrahydro-1H-carbazol-1-amine hydrochloride salt
(1S)-6-Methyl-N-[(1S)-1-phenylethyl]-2,3,4,9-tetrahydro-1H-carbazol-1-amine hydrochloride salt
(1R)-6-Methyl-N-[(1S)-1-phenylethyl]-2,3,4,9-tetrahydro-1H-carbazol-1-amine hydrochloride salt
6-Nitro-N-[(1R)-1-phenylethyl]-2,3,4,9-tetrahydro-1H-carbazol-1-amine hydrochloride salt
(3R)-7-Bromo-N-[(1R)-1-phenylethyl]-1,2,3,4-tetrahydrocyclopenta[b]indol-3-amine hydrochloride salt
N-Benzyl-6-methoxy-2,3,4,9-tetrahydro-1H-carbazol-1-amine hydrochloride salt
N-Benzyl-2-bromo-5,6,7,8,9,10-hexahydrocyclohepta[b]indol-6-amine hydrochloride
2-Bromo-N-[(1R)-1-phenylethyl]-5,6,7,8,9,10-hexahydrocyclohepta[b]indol-6-amine hydrochloride
2-Bromo-N-(2-phenylethyl)-5,6,7,8,9,10-hexahydrocyclohepta[b]indol-6-amine hydrochloride
6-Bromo-N-(4-fluorobenzyl)-2,3,4,9-tetrahydro-1H-carbazol-1-amine hydrochloride
N-Benzyl-6-(trifluoromethyl)-2,3,4,9-tetrahydro-1H-carbazol-1-amine hydrochloride
N-[(1R)-1-Phenylethyl]-6-(trifluoromethyl)-2,3,4,9-tetrahydro-1H-carbazol-1-amine hydrochloride
N-Benzhydryl-6-bromo-2,3,4,9-tetrahydro-1H-carbazol-1-amine hydrochloride
7-Bromo-N-[(1R)-1-phenylethyl]-2,3,4,9-tetrahydro-1H-carbazol-1-amine hydrochloride
7-Bromo-N-(2,3-dihydro-1H-inden-2-yl)-2,3,4,9-tetrahydro-1H-carbazol-1-amine hydrochloride
6-Bromo-1-[(phenylmethyl)oxy]-2,3,4,9-tetrahydro-1H-carbazole
N-(6-Bromo-2,3,4,9-tetrahydro-1H-carbazol-1-yl)-N'-isopropylurea
Methyl 6-bromo-2,3,4,9-tetrahydro-1H-carbazol-1-ylcarbamate
N-(6-Bromo-2,3,4,9-tetrahydro-1H-carbazol-1-yl)cyclohexanecarboxamide
N-(6-Bromo-2,3,4,9-tetrahydro-1H-carbazol-1-yl)methanesulfonamide; and
N-(6-Bromo-2,3,4,9-tetrahydro-1H-carbazol-1-yl)urea.

Even still more preferred compounds include:

N-(4-Methoxybenzyl)-2,3,4,9-tetrahydro-1H-carbazol-1-amine hydrochloride salt
N-(1,3-Benzodioxol-5-ylmethyl)-2,3,4,9-tetrahydro-1H-carbazol-1-amine hydrochloride salt
6-Bromo-N-(2-phenylethyl)-2,3,4,9-tetrahydro-1H-carbazol-1-amine hydrochloride salt
(1R)-6-Bromo-N-(2,3-dihydro-1H-inden-2-yl)-2,3,4,9-tetrahydro-1H-carbazol-1-amine hydrochloride salt
(1S)-6-Bromo-N-(2,3-dihydro-1H-inden-2-yl)-2,3,4,9-tetrahydro-1H-carbazol-1-amine hydrochloride salt
N-Benzyl-6-bromo-2,3,4,9-tetrahydro-1H-carbazol-1-amine hydrochloride salt
6-Bromo-N-[(1R)-1-phenylethyl]-2,3,4,9-tetrahydro-1H-carbazol-1-amine hydrochloride salt
(1R)-6-bromo-N-[(1R)-1-phenylethyl]-2,3,4,9-tetrahydro-1H-carbazol-1-amine hydrochloride salt
(1S)-6-Bromo-N-[(1R)-1-phenylethyl]-2,3,4,9-tetrahydro-1H-carbazol-1-amine hydrochloride salt
6-Bromo-N-(1-methyl-1-phenylethyl)-2,3,4,9-tetrahydro-1H-carbazol-1-amine hydrochloride salt
6-Bromo-N-[(1S)-1-phenylethyl]-2,3,4,9-tetrahydro-1H-carbazol-1-amine hydrochloride salt
(1S)-6-Bromo-N-[(1S)-1-phenylethyl]-2,3,4,9-tetrahydro-1H-carbazol-1-amine hydrochloride salt
(1R)-6-Bromo-N-[(1S)-1-phenylethyl]-2,3,4,9-tetrahydro-1H-carbazol-1-amine hydrochloride salt
6-Bromo-N-methyl-N-(2-phenylethyl)-2,3,4,9-tetrahydro-1H-carbazol-1-amine hydrochloride salt
6-Bromo-N-[(2R)-2-phenylpropyl]-2,3,4,9-tetrahydro-1H-carbazol-1-amine hydrochloride salt
6-Methyl-N-(2-phenylethyl)-2,3,4,9-tetrahydro-1H-carbazol-1-amine hydrochloride salt
N-(2,3-Dihydro-1H-inden-2-yl)-6-methyl-2,3,4,9-tetrahydro-1H-carbazol-1-amine hydrochloride salt
6-Methyl-N-[(1R)-1-phenylethyl]-2,3,4,9-tetrahydro-1H-carbazol-1-amine hydrochloride salt
(1R)-6-Methyl-N-[(1R)-1-phenylethyl]-2,3,4,9-tetrahydro-1H-carbazol-1-amine hydrochloride salt (1R)-6-Methyl-N-[(1S)-1-phenylethyl]-2,3,4,9-tetrahydro-1H-carbazol-1-amine hydrochloride salt 6-Nitro-N-[(1R)-1-phenylethyl]-2,3,4,9-tetrahydro-1H-carbazol-1-amine hydrochloride salt (3R)-7-Bromo-N-[(1R)-1-phenylethyl]-1,2,3,4-tetrahydrocyclopenta[b]indol-3-amine hydrochloride salt N-Benzyl-2-bromo-5,6,7,8,9,10-hexahydrocyclohepta[b]indol-6-amine hydrochloride 2-Bromo-N-[(1R)-1-phenylethyl]-5,6,7,8,9,10-hexahydrocyclohepta[b]indol-6-amine hydrochloride 2-Bromo-N-(2-phenylethyl)-5,6,7,8,9,10-hexahydrocyclohepta[b]indol-6-amine hydrochloride 6-Bromo-N-(4-fluorobenzyl)-2,3,4,9-tetrahydro-1H-carbazol-1-amine hydrochloride N-Benzyl-6-(trifluoromethyl)-2,3,4,9-tetrahydro-1H-carbazol-1-amine hydrochloride N-[(1R)-1-Phenylethyl]-6-(trifluoromethyl)-2,3,4,9-tetrahydro-1H-carbazol-1-amine hydrochloride N-Benzhydryl-6-bromo-2,3,4,9-tetrahydro-1H-carbazol-1-amine hydrochloride 7-Bromo-N-[(1R)-1-phenylethyl]-2,3,4,9-tetrahydro-1H-carbazol-1-amine hydrochloride 7-Bromo-N-(2,3-dihydro-1H-inden-2-yl)-2,3,4,9-tetrahydro-1H-carbazol-1-amine hydrochloride 6-Bromo-1-[(phenylmethyl)oxy]-2,3,4,9-tetrahydro-1H-carbazole N-(6-Bromo-2,3,4,9-tetrahydro-1H-carbazol-1-yl)-N'-isopropylurea Methyl 6-bromo-2,3,4,9-tetrahydro-1H-carbazol-1-ylcarbamate N-(6-Bromo-2,3,4,9-tetrahydro-1H-carbazol-1-yl)cyclohexanecarboxamide; and N-(6-Bromo-2,3,4,9-tetrahydro-1H-carbazol-1-yl)methanesulfonamide.

One embodiment of the present invention further includes:

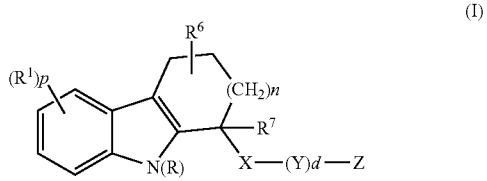

(I)

including salts, solvates and pharmaceutically functional derivatives, wherein $R^6$ is H, alkyl, —$OR^2$, —$NR^2R^3$, Ay, Het, —$C(O)R^2$, —$CO_2R^2$, —$CONR^2R^3$, —$S(O)_mR^2$, or oxo, where $R^2$, $R^3$, m, Ay, and Het are as defined; and $R^7$ is H or alkyl;

provided $R^6$ and $R^7$ are not both H.

One aspect of the present invention includes compounds selected from

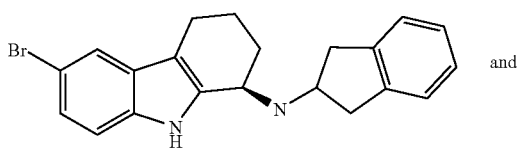 and

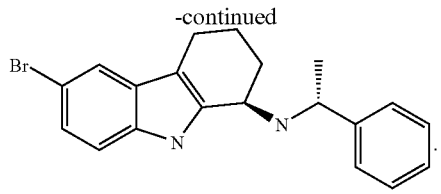

One aspect of the present invention includes a pharmaceutical composition comprising a compound of the present invention and a pharmaceutically acceptable carrier.

One aspect of the present invention includes a compound of the present invention for use as an active therapeutic substance.

One aspect of the present invention includes a compound of the present invention for use in the treatment or prophylaxis of diseases and conditions caused by oncogenic viruses, including adenoviruses, retroviruses, and retroviruses such as polyoma viruses and papilloma viruses (formerly referred to as from the papovavirus family).

One aspect of the present invention includes a compound of the present invention for use in the treatment or prophylaxis of conditions or disorders due to HPV infection. Particularly the condition or disease is warts, genital warts, cervical dysplasia, recurrent respiratory papillomatosis, or cancers associated with papillomavirus infection. More particularly the cancer is anogenital cancers, head and neck cancers, and skin cancers. More particularly the anogenital cancers are cervical, anal and perianal, vulvar, vaginal, and penile cancers; the head and neck cancers are oral pharyngeal region and esophagus cancers; and the skin cancers are basal cell carcinoma and squamous cell carcinoma.

Another aspect of the present invention also includes the use of a compound of the present invention in the manufacture of a medicament for use in the treatment or prophylaxis of oncogenic viruses, including adenoviruses, retroviruses, and viruses from the papovavirus family, such as polyoma viruses and papilloma viruses.

One aspect of the present invention includes the use of a compound of the present invention in the manufacture of a medicament for use in the treatment or prophylaxis of conditions or disorders due to HPV infection. Particularly the present invention includes usefulness with regard to the treatment and/or prophylaxis of warts, genital warts, cervical dysplasia, recurrent respiratory papillomatosis, or cancers associated with papillomavirus infection.

One aspect of the present invention includes a method for the treatment or prophylaxis of oncogenic viruses, including adenoviruses, retroviruses, and viruses from the papovavirus family, such as polyoma viruses and papilloma viruses comprising the administration of a compound according to the present invention.

One aspect of the present invention includes a method for the treatment or prophylaxis of conditions or disorders due to HPV infection comprising the administration of a compound according to the present invention. Particularly the condition or disorder is warts, genital warts, cervical dysplasia, recurrent respiratory papillomatosis, or cancers associated with papillomavirus infection.

As noted herein, p is defined as 0, 1, 2, 3, 4, or 5. Notably, as will be appreciated by those skilled in the art, the value(s) of p should not exceed the substitutable positions on the depicted rings. Further, n is defined as 0, 1, or 2. For clarity, when n is 0, a 5-membered ring is described.

DETAILED DESCRIPTION OF THE PREFERRED EMBODIMENT

Terms are used within their accepted meanings. The following definitions are meant to clarify, but not limit, the terms defined.

As used herein the term "alkyl" refers to a straight or branched chain hydrocarbon, preferably having from one to twelve carbon atoms, that may be optionally substituted, with multiple degrees of substitution included within the present invention. Examples of "alkyl" as used herein include, but are not limited to, methyl, ethyl, propyl, isopropyl, isobutyl, n-butyl, tert-butyl, isopentyl, n-pentyl, and substituted versions thereof.

As used throughout this specification, the preferred number of atoms, such as carbon atoms, will be represented by, for example, the phrase "$C_x$-$C_y$ alkyl," which refers to an alkyl group, as herein defined, containing the specified number of carbon atoms. Similar terminology will apply for other preferred terms and ranges as well.

As used herein the term "alkenyl" refers to a straight or branched chain aliphatic hydrocarbon containing one or more carbon-to-carbon double bonds that may be optionally substituted, with multiple degrees of substitution included within the present invention. Examples include, but are not limited to, vinyl, allyl, and the like and substituted versions thereof.

As used herein the term "alkynyl" refers to a straight or branched chain aliphatic hydrocarbon containing one or more carbon-to-carbon triple bonds that may be optionally substituted, with multiple degrees of substitution included within the present invention. Examples include, but are not limited to, ethynyl and the like and substituted versions thereof.

As used herein, the term "alkylene" refers to a straight or branched chain divalent hydrocarbon radical, preferably having from one to ten carbon atoms. Alkylene groups as defined herein may optionally be substituted, with multiple degrees of substitution included within the present invention. Examples of "alkylene" as used herein include, but are not limited to, methylene, ethylene, n-propylene, n-butylene, and substituted versions thereof.

As used herein, the term "alkenylene" refers to a straight or branched chain divalent hydrocarbon radical, preferably having from one to ten carbon atoms, containing one or more carbon-to-carbon double bonds that may be optionally substituted, with multiple degrees of substitution included within the present invention. Examples include, but are not limited to, vinylene, allylene or 2-propenylene, and the like and substituted versions thereof.

As used herein, the term "alkynylene" refers to a straight or branched chain divalent hydrocarbon radical, preferably having from one to ten carbon atoms, containing one or more carbon-to-carbon triple bonds that may be optionally substituted, with multiple degrees of substitution included within the present invention. Examples include, but are not limited to, ethynylene and the like and substituted versions thereof.

As used herein, the term "cycloalkyl" refers to an optionally substituted non-aromatic cyclic hydrocarbon ring, which optionally includes an alkylene linker through which the cycloalkyl may be attached, with multiple degrees of substitution included within the present invention. Exemplary "cycloalkyl" groups include, but are not limited to, cyclopropyl, cyclobutyl, cyclopentyl, cyclohexyl, cycloheptyl, and substituted versions thereof. As used herein, the term "cycloalkyl" includes an optionally substituted fused polycyclic hydrocarbon saturated ring and aromatic ring system, namely polycyclic hydrocarbons with less than maximum number of non-cumulative double bonds, for example where a saturated hydrocarbon ring (such as a cyclopentyl ring) is fused with an aromatic ring (herein "aryl," such as a benzene ring) to form, for example, groups such as indane.

As used herein, the term "cycloalkenyl" refers to an optionally substituted non-aromatic cyclic hydrocarbon ring containing one or more carbon-to-carbon double bonds which optionally includes an alkylene linker through which the cycloalkenyl may be attached, with multiple degrees of substitution included within the present invention. Exemplary "cycloalkenyl" groups include, but are not limited to, cyclopropenyl, cyclobutenyl, cyclopentenyl, cyclohexenyl, cycloheptenyl, and substituted versions thereof.

As used herein, the term "cycloalkylene" refers to a divalent, optionally substituted non-aromatic cyclic hydrocarbon ring, with multiple degrees of substitution included within the present invention. Exemplary "cycloalkylene" groups include, but are not limited to, cyclopropylene, cyclobutylene, cyclopentylene, cyclohexylene, cycloheptylene, including fused systems with reference to the above definition for "cycloalkyl," and further including substituted versions thereof.

As used herein, the term "cycloalkenylene" refers to a divalent optionally substituted non-aromatic cyclic hydrocarbon ring containing one or more carbon-to-carbon double bonds, with multiple degrees of substitution included within the present invention. Exemplary "cycloalkenylene" groups include, but are not limited to, cyclopropenylene, cyclobutenylene, cyclopentenylene, cyclohexenylene, cycloheptenylene, and substituted versions thereof.

As used herein, the term "heterocycle" or "heterocyclyl" refers to an optionally substituted mono- or polycyclic ring system containing one or more degrees of unsaturation and also containing one or more heteroatoms. Preferred heteroatoms include N, O, and/or S, including N-oxides, sulfur oxides, and dioxides. Preferably the ring is three to twelve-membered and is either fully saturated or has one or more degrees of unsaturation. Multiple degrees of substitution are included within the present definition. Such rings may be optionally fused to one or more of another "heterocyclic" ring(s) or cycloalkyl ring(s). Examples of "heterocyclic" groups include, but are not limited to, tetrahydrofuran, pyran, 1,4-dioxane, 1,3-dioxane, piperidine, pyrrolidine, morpholine, tetrahydrothiopyran, and tetrahydrothiophene.

As used herein, the term "aryl" refers to an optionally substituted benzene ring or to an optionally substituted fused benzene ring system, for example anthracene, phenanthrene, or naphthalene ring systems. Multiple degrees of substitution are included within the present definition. Examples of "aryl" groups include, but are not limited to, phenyl, 2-naphthyl, 1-naphthyl, and substituted derivatives thereof.

As used herein, the term "heteroaryl" refers to an optionally substituted monocyclic five to seven membered aromatic ring, or to an optionally substituted fused bicyclic aromatic ring system comprising two of such aromatic rings. These heteroaryl rings contain one or more nitrogen, sulfur, and/or oxygen atoms, where N-oxides, sulfur oxides, and dioxides are permissible heteroatom substitutions. Multiple degrees of substitution are included within the present definition. Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, benzimidizole, imidazopyridine, pyrazolopyridine, pyrazolopyrimidine, and substituted versions thereof.

As used herein the term "halogen" refers to fluorine, chlorine, bromine, or iodine.

As used herein the term "haloalkyl" refers to an alkyl group, as defined herein, which is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo, and iodo. The term "haloalkyl" should be interpreted to include such substituents as perfluoroalkyl groups and the like.

As used herein the term "alkoxy" refers to the group —$OR^a$, where $R^a$ is alkyl as defined above.

As used herein the term "alkoxycarbonyl" refers to groups such as:

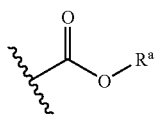

where the $R^a$ represents an alkyl group as herein defined.

As used herein the term "aryloxycarbonyl" refers to groups such as:

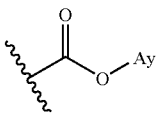

where the Ay represents an aryl group as herein defined.

As used herein the term "heteroaryloxycarbonyl" refers to groups such as:

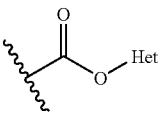

where the Het represents a heteroaryl group as herein defined.

As used herein the term "nitro" refers to the group —$NO_2$.

As used herein the term "cyano" refers to the group —CN.

As used herein the term "azido" refers to the group —$N_3$.

As used herein the term "acyl" refers to the group $R^bC$(O)—, where $R^b$ is alkyl, aryl, heteroaryl, or heterocyclyl, as each is defined herein.

As used herein the term "oxo" refers to the group =O.

Also, as used herein throughout the present specification, the phrase "optionally substituted" or variations thereof denote an optional substitution, including multiple degrees of substitution, with one or more substitutent group. The phrase should not be interpreted as duplicative of the substitutions herein described and depicted. Exemplary optional substituent groups include acyl; alkyl; alkenyl; alkynyl; alkylsulfonyl; alkoxy; alkoxycarbonyl; cyano; halogen; haloalkyl; hydroxy; nitro; aryl, which may be further substituted with acyl, alkoxy, alkyl, alkenyl, alkynyl, alkylsulfonyl, cyano, halogen, haloalkyl, hydroxy, or nitro; heteroaryl, which may be further substituted with acyl, alkoxy, alkyl, alkenyl, alkynyl, alkylsulfonyl, cyano, halogen, haloalkyl, hydroxy, or nitro; arylsulfonyl, which may be further substituted with acyl, alkoxy, alkyl, alkenyl, alkynyl, alkylsulfonyl, cyano, halogen, haloalkyl, hydroxy, or nitro; heteroarylsulfonyl, which may be further substituted with acyl, alkoxy, alkyl, alkenyl, alkynyl, alkylsulfonyl, cyano, halogen, haloalkyl, hydroxy, or nitro; aryloxy, which may be further substituted with acyl, alkoxy, alkyl, alkenyl, alkynyl, alkylsulfonyl, cyano, halogen, haloalkyl, hydroxy, or nitro; heteroaryloxy, which may be further substituted with acyl, alkoxy, alkyl, alkenyl, alkynyl, alkylsulfonyl, cyano, halogen, haloalkyl, hydroxy, or nitro; aryloxycarbonyl, which may be further substituted with acyl, alkoxy, alkyl, alkenyl, alkynyl, alkylsulfonyl, cyano, halogen, haloalkyl, hydroxy, or nitro; heteroaryloxycarbonyl, which may be further substituted with acyl, alkoxy, alkyl, alkenyl, alkynyl, alkylsulfonyl, cyano, halogen, haloalkyl, hydroxy, or nitro; or —$N(R^*)_2$; where for each occurrence $R^*$ is independently selected from H, alkyl, alkenyl, alkynyl, cycloalkyl, heterocyclyl, aryl, aralkyl, heteroaryl, heteroaralkyl, alkylsulfonyl, arylsulfonyl, or heteroarylsulfonyl, where each occurrence of such aryl or heteroaryl may be substituted with one or more acyl, alkoxy, alkyl, alkenyl, alkylsulfonyl, cyano, halogen, haloalkyl, hydroxy, or nitro, or the two $R^*$s may combine to form a ring, optionally having additional heteroatoms, optionally having one or more degrees of unsaturation, and optionally being further substituted with acyl, alkoxy, alkyl, alkenyl, alkynyl, alkylsulfonyl, cyano, halogen, haloalkyl, hydroxy, or nitro.

The compounds of formulas (I) may crystallize in more than one form, a characteristic known as polymorphism, and such polymorphic forms ("polymorphs") are within the scope of formula (I). Polymorphism generally can occur as a response to changes in temperature, pressure, or both. Polymorphism can also result from variations in the crystallization process. Polymorphs can be distinguished by various physical characteristics known in the art such as x-ray diffraction patterns, solubility, and melting point.

Certain of the compounds described herein contain one or more chiral centers, or may otherwise be capable of existing as multiple stereoisomers. The scope of the present invention includes mixtures of stereoisomers as well as purified enantiomers or enantiomerically/diastereomerically enriched mixtures. Also included within the scope of the invention are the individual isomers of the compounds represented by formula (I), as well as any wholly or partially equilibrated mixtures thereof. The present invention also includes the individual isomers of the compounds represented by the formulas above as mixtures with isomers thereof in which one or more chiral centers are inverted.

Typically, but not absolutely, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts.

Representative pharmaceutically acceptable salts include, but should not be considered limited to, acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of Formula I, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of the present invention that, upon administration to a mammal, is capable of providing (directly or indirectly) a compound of the present invention or an active metabolite thereof. Such derivatives, for example, esters and amides, will be clear to those skilled in the art, without undue experimentation. Reference may be made to the teaching of *Burger's Medicinal Chemistry And Drug Discovery*, $5^{th}$ Edition, Vol 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal, or human that is being sought, for instance, by a researcher or clinician. The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. For use in therapy, therapeutically effective amounts of a compound of formula (I), as well as salts, solvates, and physiological functional derivatives thereof, may be administered as the raw chemical. Additionally, the active ingredient may be presented as a pharmaceutical composition.

Accordingly, the invention further provides pharmaceutical compositions that include effective amounts of compounds of the formula (I) and salts, solvates, and physiological functional derivatives thereof, and one or more pharmaceutically acceptable carriers, diluents, or excipients. The compounds of formula (I) and salts, solvates, and physiologically functional derivatives thereof, are as herein described. The carrier(s), diluent(s) or excipient(s) must be acceptable, in the sense of being compatible with the other ingredients of the formulation and not deleterious to the recipient of the pharmaceutical composition.

In accordance with another aspect of the invention there is also provided a process for the preparation of a pharmaceutical formulation including admixing a compound of the formula (I) or salts, solvates, and physiological functional derivatives thereof, with one or more pharmaceutically acceptable carriers, diluents or excipients.

A therapeutically effective amount of a compound of the present invention will depend upon a number of factors. For example, the species, age, and weight of the recipient, the precise condition requiring treatment and its severity, the nature of the formulation, and the route of administration are all factors to be considered. The therapeutically effective amount ultimately should be at the discretion of the attendant physician or veterinarian. Regardless, an effective amount of a compound of formula (I) for the treatment of humans suffering from frailty, generally, should be in the range of 0.1 to 100 mg/kg body weight of recipient (mammal) per day. More usually the effective amount should be in the range of 1 to 10 mg/kg body weight per day. Thus, for a 70 kg adult mammal the actual amount per day would usually be from 70 to 700 mg. This amount may be given in a single dose per day or in a number (such as two, three, four, five, or more) of sub-doses per day such that the total daily dose is the same. An effective amount of a salt, solvate, or physiologically functional derivative thereof, may be determined as a proportion of the effective amount of the compound of formula (I) per se. Similar dosages should be appropriate for treatment of the other conditions referred to herein.

Pharmaceutical formulations may be presented in unit dose forms containing a predetermined amount of active ingredient per unit dose. Such a unit may contain, as a non-limiting example, 0.5 mg to 1 g of a compound of the formula (I), depending on the condition being treated, the route of administration, and the age, weight, and condition of the patient. Preferred unit dosage formulations are those containing a daily dose or sub-dose, as herein above recited, or an appropriate fraction thereof, of an active ingredient. Such pharmaceutical formulations may be prepared by any of the methods well known in the pharmacy art.

Pharmaceutical formulations may be adapted for administration by any appropriate route, for example by an oral (including buccal or sublingual), rectal, nasal, topical (including buccal, sublingual or transdermal), vaginal, or parenteral (including subcutaneous, intramuscular, intravenous or intradermal) route. Such formulations may be prepared by any method known in the art of pharmacy, for example by bringing into association the active ingredient with the carrier(s) or excipient(s). By way of example, and not meant to limit the invention, with regard to certain conditions and disorders for which the compounds of the present invention are believed useful certain routes will be preferable to others. Based upon the physical manifestations that are often associated with HPV infection, rectal, topical, or vaginal routes of administration may be preferable. As one example, for the treatment or prophylaxis of cervical dysplasia the preferred route may be a vaginal route.

Pharmaceutical formulations adapted for oral administration may be presented as discrete units such as capsules or tablets; powders or granules; solutions or suspensions, each with aqueous or non-aqueous liquids; edible foams or whips; or oil-in-water liquid emulsions or water-in-oil liquid emulsions. For instance, for oral administration in the form of a tablet or capsule, the active drug component can be combined with an oral, non-toxic pharmaceutically acceptable inert carrier such as ethanol, glycerol, water, and the like. Generally, powders are prepared by comminuting the compound to a suitable fine size and mixing with an appropriate pharmaceutical carrier such as an edible carbohydrate, as, for example, starch or mannitol. Flavorings, preservatives, dispersing agents, and coloring agents can also be present.

Capsules are made by preparing a powder, liquid, or suspension mixture and encapsulating with gelatin or some other appropriate shell material. Glidants and lubricants such as colloidal silica, talc, magnesium stearate, calcium stearate, or solid polyethylene glycol can be added to the mixture before the encapsulation. A disintegrating or solubilizing agent such as agar-agar, calcium carbonate or sodium carbonate can also be added to improve the availability of the medicament when the capsule is ingested. Moreover, when desired or necessary, suitable binders, lubricants, disintegrating agents, and coloring agents can also be incorporated into the mixture. Examples of suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants useful in these dosage forms include, for example, sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Tablets are formulated, for example, by preparing a powder mixture, granulating or slugging, adding a lubricant and disintegrant, and pressing into tablets. A powder mixture may be prepared by mixing the compound, suitably comminuted, with a diluent or base as described above. Optional ingredients include binders such as carboxymethylcellulose, aliginates, gelatins, or polyvinyl pyrrolidone, solution retardants such as paraffin, resorption accelerators such as a quaternary salt, and/or absorption agents such as bentonite, kaolin, or dicalcium phosphate. The powder mixture can be wet-granulated with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solutions, syrups, and elixirs can be prepared in dosage unit form so that a given quantity contains a predetermined amount of the compound. Syrups can be prepared, for example, by dissolving the compound in a suitably flavored aqueous solution, while elixirs are prepared through the use of a non-toxic alcoholic vehicle. Suspensions can be formulated generally by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) and salts, solvates, and physiological functional derivatives thereof, can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula (I) and salts, solvates, and physiologically functional derivatives thereof may also be delivered by the use of monoclonal antibodies as individual carriers to which the compound molecules are coupled.

The compounds may also be coupled with soluble polymers as targetable drug carriers. Such polymers can include polyvinylpyrrolidone (PVP), pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug; for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6), 318 (1986), incorporated herein by reference as related to such delivery systems.

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations may be applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouthwashes.

Pharmaceutical formulations adapted for nasal administration, where the carrier is a solid, include a coarse powder having a particle size for example in the range 20 to 500 microns. The powder is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered dose pressurized aerosols, nebulizers, or insufflators.

Pharmaceutical formulations adapted for rectal administration may be presented as suppositories or as enemas.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In addition to the ingredients particularly mentioned above, the formulations may include other agents conventional in the art having regard to the type of formulation in question. For example, formulations suitable for oral administration may include flavoring or coloring agents.

The compounds of the present invention and their salts, solvates, and physiologically functional derivatives thereof, may be employed alone or in combination with other therapeutic agents. The compound(s) of formula (I) and the other pharmaceutically active agent(s) may be administered together or separately and, when administered separately, administration may occur simultaneously or sequentially, in any order. The amounts of the compound(s) of formula (I) and the other pharmaceutically active agent(s) and the relative timings of administration will be selected in order to achieve the desired combined therapeutic effect. The administration in combination of a compound of formula (I) salts, solvates, or physiologically functional derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

The compounds of the present invention may be used in the treatment of a variety of disorders and conditions and, as such, the compounds of the present invention may be used in combination with a variety of other suitable therapeutic agents useful in the treatment or prophylaxis of those disorders or conditions. Treatment will depend upon the nature and type of HPV infection. As discussed briefly above, treatment for warts can be divided into ablative and medical approaches. The compounds of the present invention may be combined with either or both approaches.

Ablative methods include classic surgical excision and destruction by electrodesiccation, laser, or liquid nitrogen. Thus, the compounds of the present invention may be used in conjunction with such methods or upon reoccurrence after such methods. The compounds of the present invention may be used in conjunction with ablative methods to reduce the frequency of reoccurrence.

Alternatively, the present invention may be combined with other medical therapies including a variety of cytotoxic or antiviral agents. For example, and not meant to limit the invention, the compounds of the present invention may be combined with other therapeutic agents such as 5-fluorouracil, retinoic acid, podophyllin, podofilox, keratolytic agents such as salicylic acid and/or lactic acid, haptens such as diphencyprone (DPC), squaric acid dibutyl ester (SADBE) or dinitrochlorobenzene (DNCB), formalin, topical trichloroacetic acid, topical tretinoin, cidofovir, imiquimod and/or cytokines such as interferon alfa-2b.

One aspect of the present invention is the use of the compounds of the present invention for the treatment or prophylaxis of a variety of disorders including, but not limited to, diseases and conditions caused by oncogenic viruses, including adenoviruses, retroviruses, and viruses from the papovavirus family, such as polyoma viruses and papilloma viruses and more particularly papilloma viral infections. The present invention includes administering to a subject in need thereof a therapeutically effective amount of a compound of the present invention or a pharmaceutically acceptable salt, solvate or physiologically functional derivative thereof.

More specifically, the present invention includes the treatment or prophylaxis of conditions or diseases associated with papilloma viral infections. These conditions and diseases include warts (e.g. plantar warts), genital warts, recurrent respiratory papillomatosis (e.g., laryngeal papillomas), and cancers associated with papillomavirus infection. Cancers that have been associated with papillomavirus infection include anogenital cancers (e.g., cervical, anal and perianal, vulvar, vaginal, penile cancers), head and neck cancers (e.g., oral pharyngeal region, esophagus), and skin cancers (e.g., basal cell carcinoma, squamous cell carcinoma). The present invention includes administering to a subject in need thereof a therapeutically effective amount of a compound of the present invention or a salt, solvate or physiologically functional derivative thereof.

The compounds of this invention may be made by a variety of methods, including well-known standard synthetic methods. Illustrative general synthetic methods are set out below and then specific compounds of the invention are prepared in the working Examples.

In all of the examples described below, protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of formula (I).

Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, such may be obtained by stereospecific synthesis, by resolution of the final product or any convenient intermediate, or by chiral chromatographic methods as are known in the art. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994), incorporated by reference with regard to stereochemistry.

Experimental Section

As used herein the symbols and conventions used in these processes, schemes and examples, regardless of whether a particular abbreviation is specifically defined, are consistent with those used in the contemporary scientific literature, for example, the *Journal of the American Chemical Society or the*

Journal of Biological Chemistry. Specifically, but without limitation, the following abbreviations may be used in the examples and throughout the specification:

g (grams);
mg (milligrams);
L (liters);
mL (milliliters);
μL (microliters);
psi (pounds per square inch);
M (molar);
mM (millimolar);
Hz (Hertz);
MHz (megahertz);
mol (moles);
mmol (millimoles);
RT (room temperature);
h (hours);
min (minutes);
TLC (thin layer chromatography);
mp (melting point);
RP (reverse phase);
$T_r$ (retention time);
TFA (trifluoroacetic acid);
TEA (triethylamine);
THF (tetrahydrofuran);
TFAA (trifluoroacetic anhydride);
$CD_3OD$ (deuterated methanol);
$CDCl_3$ (deuterated chloroform);
DMSO (dimethylsulfoxide);
$SiO_2$ (silica);
atm (atmosphere);
EtOAc (ethyl acetate);
$CHCl_3$ (chloroform);
HCl (hydrochloric acid);
Ac (acetyl);
DMF (N,N-dimethylformamide);
Me (methyl);
$Cs_2CO_3$ (cesium carbonate);
EtOH (ethanol);
Et (ethyl);
tBu (tert-butyl);
MeOH (methanol).

Unless otherwise indicated, all temperatures are expressed in ° C. (degrees Centigrade). All reactions conducted at room temperature unless otherwise noted.

$^1$H NMR spectra were recorded on a Varian VXR-300, a Varian Unity-300, a Varian Unity400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), or br (broad).

Mass spectra were obtained on Micromass Platform or ZMD mass spectrometers from Micromass Ltd., Altricham, UK, using either Atmospheric Chemical Ionization (APCI) or Electrospray Ionization (ESI).

Analytical thin layer chromatography was used to verify the purity of intermediate(s) which could not be isolated or which were too unstable for full characterization as well as to follow the progress of reaction(s).

Compounds of formula (I), wherein X is NH, $R^1$ and p are as defined above and LV is a leaving group such as halogen (F, Cl, Br, I), SOAy, $SO_2$Ay, SOR, $SO_2$R, may be conveniently prepared by the process outlined below:

Scheme 1

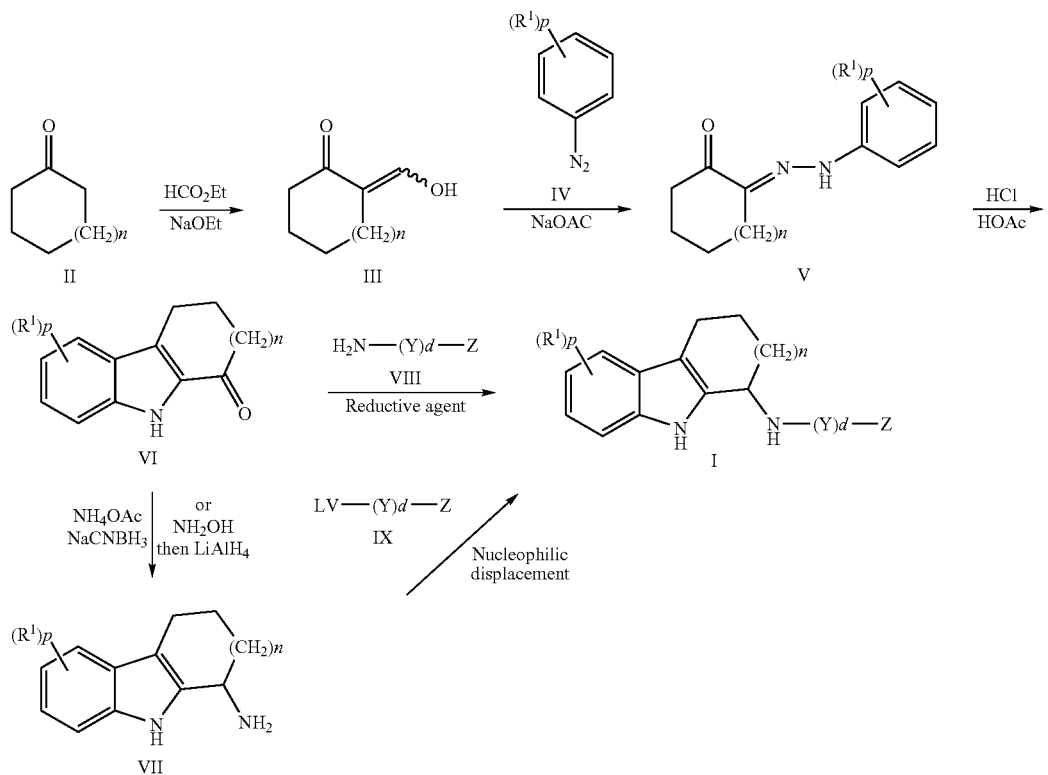

Generally, the process for preparing the compounds of formula (I), where LV is as defined above (all formulas and all other variables having been defined above) comprises the steps of:

a) reacting a compound of formula (II) with ethyl formate;
b) reacting the compound of formula (III) with diazocompound of formula (IV);
c) indolizing the compound of formula (V) to prepare a compound of formula (VI);
d) reductive amination of compound of formula (VI) to form compound of formula (VII); and
e) forming compounds of formula (I) from compound (VII) by nucleophilic displacement.

Alternatively, f) forming compounds of formula (I) via reductive amination of compound (VI).

More specifically, a compound of formula (I), wherein all variables are as defined above, can be prepared reacting the compound of formula (VI) with an amine of formula (VIII) in the presence of a reducing agent:

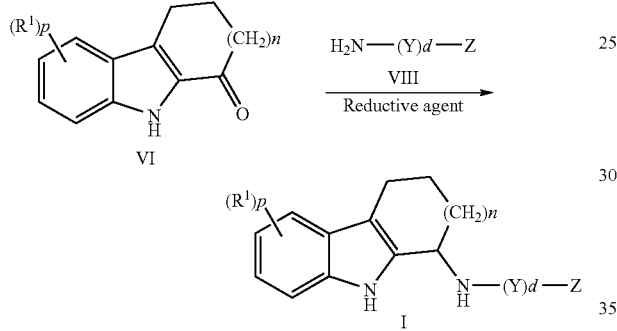

again, where all variables are as defined above.

The reaction may be carried out as a two step process where an imine is formed under conditions that allow for removal of water followed by reduction. Alternatively this reaction can be carried out in one pot by adding amine (VIII) and the reductive agent, either sequentially or at the same time.

For the two step process, typically a compound of formula (VI) is dissolved in an inert solvent such as toluene, and either an equivalent or an excess of an amine of formula (VIII) is added, followed by the optional addition of an acid catalyst such as para-toluenesulfonic acid. The reaction is heated to reflux for azeotropic removal of water. Optionally molecular sieves or dehydrating agents, such as trimethylorthoformate, can be used for the removal of water.

The imine can be isolated or used directly for the next step. The imine is dissolved in a suitable solvent and reduced by additon of a reductive agent. Suitable solvents include lower alcohols (methanol, ethanol, and the like) tetrahydrofuran, or other similar solvents well known to those skilled in the art. Suitable reductive agents include, but are not limited to, sodium cyanoborohydride, sodium triacetoxyborohydride, borane-tetrahydrofuran complex, sodium borohydride, and the like.

For a one pot process, a compound of formula (VI) is dissolved in an inert solvent. An amine of formula (VIII) is added to this solution, followed by the addition of a suitable reductive agent. The reaction may optionally be heated to between about 50° C.-150° C. Suitable solvents include but are not limited to, dichloromethane, dichloroethane, and the like. Suitable reductive agents include but are not limited to sodium cyanoborohydride, sodium triacetoxyborohydride, sodium borohydride, and the like.

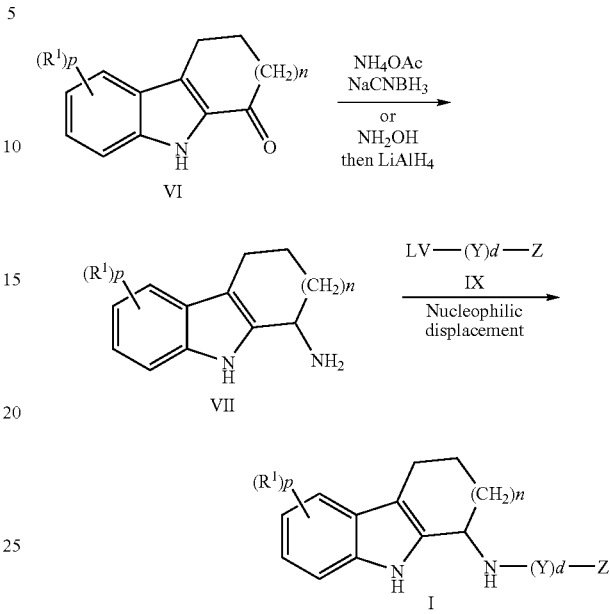

As described above, alternatively a compound of formula (I) can be formed from an amine of formula (VII). Treatment of compound of formula (VI) in an inert solvent with ammonium salt and a reductive agent, optionally with heating, gives an amine of formula (VII). Suitable solvents include, but are not limited to, methanol, ethanol, dichloro-methane, dichloroethane, and the like. Suitable reductive agents include, but are not limited to, sodium cyanoborohydride, sodium triacetoxyborohydride, sodium borohydride, and the like. Suitable ammonium salts include, but are not limited to, ammonium acetate, ammonium formate, and the like. An amine of formula (VII) can also be formed by treatment of compound of formula (VI) with hydroxylamine, followed by reduction with suitable reductive agents which include, but are not limited to, lithium aluminium hydride and the like.

Condensation of compound of formula (VII) with compound of formula (IX) gives compound of formula (I). This condensation can be carried out neat or in the presence of solvent, optionally with heating. The condensation optionally may be carried out in a microwave. Suitable solvents include, but are not limited to, N,N-dimethylformamide, 1-methyl-2-pyrrolidinone, dimethyl-sulfoxide, acetonitrile, nitromethane and the like. Optionally a base may be added to the condensation reaction. Examples of suitable bases include, but are not limited to, sodium carbonate, sodium bicarbonate, triethylamine, and the like.

As will be appreciated by those skilled in the art, compounds of formula (VI) may be prepared in a similar fashion as described in the literature (J. Med. Chem. 1973, 16, 425 and J. Org. Chem. 1968, 32, 1265), incorporated herein by reference with regard to such preparation.

Compounds of formula (I) where X is NH and —((Y)$_d$-Z) is —CONR$^2$R$^3$ can be formed from a compound of formula (VII) by reaction with isocyanates as outlined below.

Scheme 2

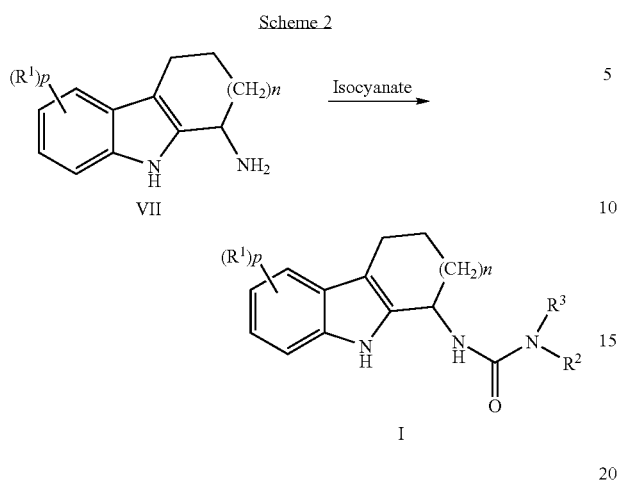

More specifically a compound of formula (VII) can be treated with isocyanate in a suitable solvent, optionally with heating. Suitable solvents include, but are not limited to, tetrahydrofuran, dichloromethane, lower alcohols (methanol, ethanol), and the like. Isocyanates are commercially available and/or can be made by methods readily available or known to those skilled in the art.

Generally, the process for preparing the compounds of formula (I), where X is O and —(Y)$_d$-Z is as defined above comprises the steps of:

a) forming a compound illustrated by formula (X) by protecting the depicted nitrogen in a compound of formula (VI);
b) reducing compound of formula (X) to an alcohol of formula (XI);
c) reaction of compound of formula (XI) with a compound of formula (XII) to give compound of formula (XIII);
d) deprotection of compound of formula (XIII) to give a compound of formula (I) where X is O and —(Y)$_d$-Z is as herein defined;

Scheme 3

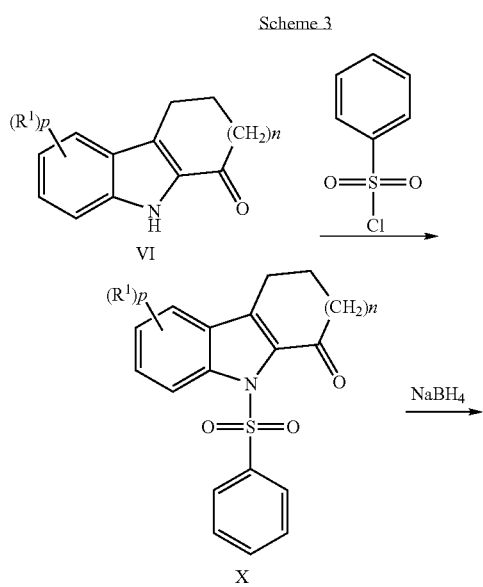

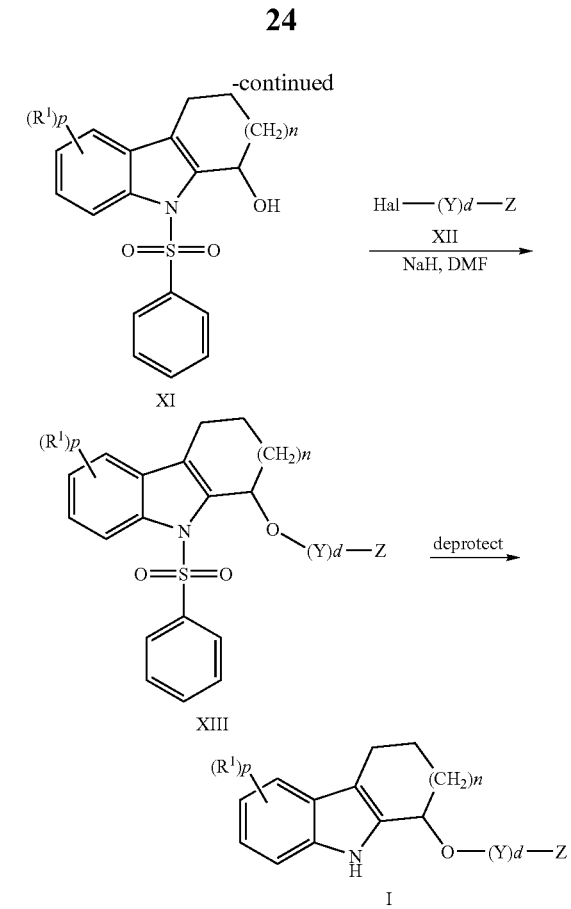

Scheme 3 illustrates one embodiment of this general process using a preferred protecting group, namely benzene sulfonylchloride. More specifically the depicted indole nitrogen in a compound of formula (VI) is protected using a suitable protecting group. Suitable protecting groups include phenylsulfonyl and other related protecting groups. Thus, treatment of a compound of formula (VI) with benzene sulfonylchloride in the presence of base and in a suitable solvent, optionally with heating, yields a compound of formula (X).

Reduction of a compound of formula (X) with a suitable reducing agent gives a compound of formula (XI). Suitable reducing agents include, but are not limited to, sodium borohydride, diborane, and the like. Suitable solvents for the reduction include, but are not limited to, tetrahydrofuran, halogenated solvents (dichloromethane and the like), lower alcohols (methanol, ethanol, and the like), and other similar solvents.

Reaction of compound of formula (XI) with a compound of formula (XII) in a suitable solvent in the presence of a deprotonating agent/base, optionally with heating gives a compound of formula (XIII). Suitable solvents include, but are not limited to, N,N-dimethylformamide, dimethylsulfoxide, acetonitrile, nitromethane, tetrahydrofuran, and the like. Suitable bases include, but are not limited to, sodium hydride, sodium t-butoxide, and the like.

Deprotection of compound of formula (XIII) with, for example, aqueous sodium hydroxide yields a compound of formula (I) where X is O.

One of ordinary skill in the art will appreciate the ability to adapt the illustrated schemes if another suitable protecting group is used.

Generally, as illustrated below, a compound of formula (I) where X is N and —((Y)$_d$-Z) is substituted alkylene—Ay, can be prepared from a compound of formula (VII).

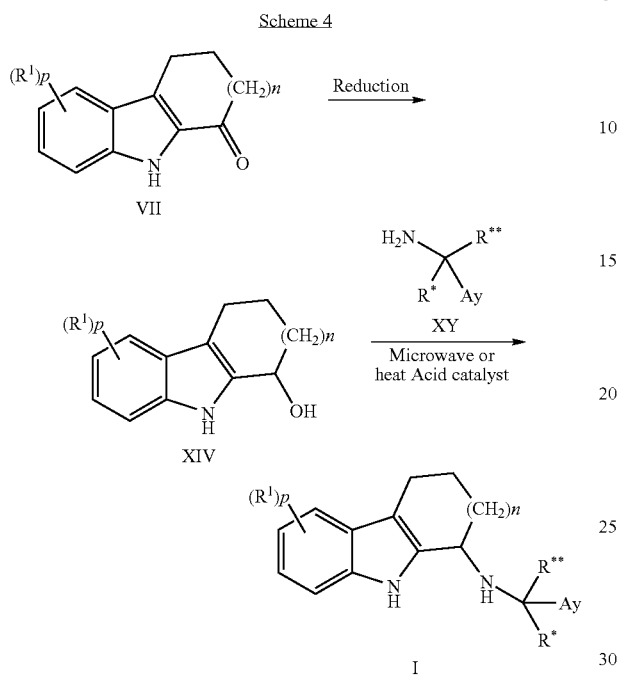

Scheme 4

More specifically compound of formula (VII) can be reduced to an alcohol of formula (XIV) with a suitable reducing agent. Suitable reducing agents include, but are not limited to, sodium borohydride, diborane, and the like. Suitable solvents for the reduction include, but are not limited to, tetrahydrofuran, dichloromethane, and lower alcohols (methanol, ethanol, and the like).

An alcohol of formula (XIV) can be treated with an amine of formula (XV) at high temperature, optionally in the presence of acid catalyst to give a compound of formula (I) where —((Y)$_d$-Z) is substituted alkylene—Ay, such as —CR*R**Ay. As described the depiction of —CR*R**— is substituted alkylene. Thus, R* and R** may be a variety of substituents, including the substituents listed herein under the description of optionally substituted. Preferably, one of R* and R** is H and the other is selected from H, alkyl, or aryl; or both R* and R** are alkyl. This reaction may be performed in a microwave, as described below in more detail.

Additionally a compound of formula (I) where R is halogen (abbreviated "Hal" herein below) and R is at the 8-position of the depicted tetrahydrocarbazole core may be synthesized from a compound of formula (XV) as outlined below.

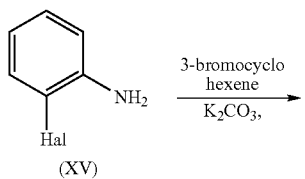

Scheme 5

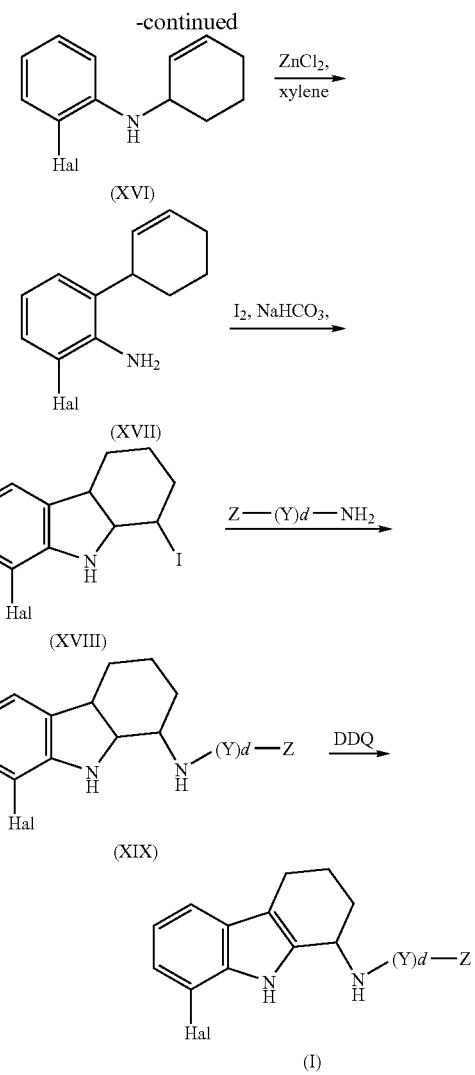

Generally the process for preparing compound of formula (I) where a halogen (Hal) is at the 8-position comprises the steps of:
a) reaction of a compound of formula (XV) with 3-bromocyclohexene to give a compound of formula (XVI);
b) rearrangement of a compound of formula (XVI) to give a compound of formula (XVII);
c) cyclization of a compound of formula (XVII) to give a compound of formula (XVIII);
d) reaction of a compound of formula (XVIII) with an amine (e.g., Z-(Y)$_d$—NH$_2$) to form a compound of formula (XIX); and
e) oxidation of a compound of formula (XIX) to give a compound of formula (I).

More specifically, treatment of a compound of formula (XV) with 3-bromocyclo-hexene in a suitable solvent and in the presence of base, optionally with heating, gives a compound of formula (XVI). Suitable solvents include, but are not limited to, N,N-dimethylformamide, acetonitrile, nitromethane, and the like. Suitable bases include, but are not limited to, sodium bicarbonate, sodium carbonate, potassium carbonate, cesium carbonate, triethylamine, and the like.

Treatment of a compound of formula (XVI) in a suitable solvent with heating in the presence of a Lewis acid gives a compound of formula (XVII). Suitable solvents include high boiling solvents, such as xylene and the like. Suitable Lewis acids include, but are not limited to, zinc chloride and the like.

Treatment of a compound (XVII) with iodine and base in a suitable solvent gives a compound of formula (XVIII). Suitable bases include, but are not limited to, sodium bicarbonate, sodium carbonate, potassium carbonate, cesium carbonate, triethylamine, and the like. Suitable solvents include, but are not limited to, tetrahydrofuran, acetonitrile, dichloromethane, and the like.

Reaction of a compound (XVIII) with an amine of formula Z-(Y)$_d$—NH$_2$ in a suitable solvent, optionally with heating and optionally in the presence of base gives a compound of formula (XIX). As is appreciated in the art, an equivalent or an excess of the amine may be used or the amine may be used as solvent. Other suitable solvents include, but are not limited to, N,N-dimethylformamide, nitromethane, acetonitrile, and the like. Suitable bases include, but are not limited to, sodium bicarbonate, sodium carbonate, potassium carbonate, cesium carbonate, triethylamine, and the like. The reaction can optionally be heated to between about 30-200° C. or carried out in a microwave.

A compound of formula (XIX) then is oxidized to give compound of formula (I). Suitable oxidizing agents include, as depicted, but should not be considered limiting, 2,3-dichloro-5,6-dicyano-1,4-benzoquinone ("DDQ") and the like. Suitable solvents for the reaction include halogenated solvents (such as dichloromethane). The reaction can be carried out at room temperature or optionally with heating.

As will be appreciated by those skilled in the art, a compound of formula (I) can be converted to another compound of formula (I) by known or readily available methods.

EXAMPLES

Example 1

6-Chloro-2,3,4,9-tetrahydro-1H-carbazol-1-one

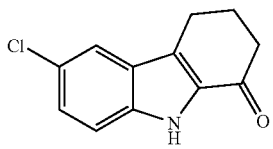

a) Cyclohexane-1,2-dione (4-chlorophenyl)hydrazone. To a cold (0° C.) solution of 4-chloroaniline (5.6 g, 44 mmol) in concentrated hydrochloric acid (5 mL) was added sodium nitrite (3.0 g, 44 mmol) dissolved in water (10 mL) portionwise over 20 minutes. The mixture was stirred at 0° C. for 30 minutes. In a separate flask, a cool solution of 2-(hydroxymethylene)cyclohexanone (Organic Syntheses, Collective Volume 4, 1963, pg. 536, incorporated herein by reference with regard to such synthesis) (5.0 g, 40 mmol) in methanol (30 mL) was treated with a solution of sodium acetate (8.3 g, 101 mmol) in water (25 mL). The mixture was stirred at 0° C. for 20 minutes and the diazonium salt slurry was added. The combined mixture was stirred for 10-15 minutes, collected by filtration, triturated with ethanol, and collected by filtration to give cyclohexane-1,2-dione (4-chlorophenyl)hydrazone (4.6 g, 49% yield) as a yellow solid. $^1$H-NMR (DMSO-d$_6$): δ 9.93 (s, 1H), 7.29 (m, 4H), 2.55 (m, 2H), 2.40 (m, 2H), 1.84-1.75 (m, 4H).

b) 6-Chloro-2,3,4,9-tetrahydro-1H-carbazol-1-one. A solution of cyclohexane-1,2-dione (4-chlorophenyl)hydrazone (2.3 g, 9.7 mmol) in hydrochloric acid (2 mL) and acetic acid (8 mL) was heated at 120° C. for 20 minutes. The mixture was cooled slightly and treated with ice water. The resulting precipitate was collected by filtration to give 6-chloro-2,3,4,9-tetrahydro-1H-carbazol-1-one (1.9 g, 88% yield) as brown solid. $^1$H-NMR (DMSO-d$_6$): δ 11.78 (s, 1H), 7.75 (m, 1H), 7.38 (d, 1H), 7.28 (dd, 1H), 2.92 (t, 2H), 2.55 (t, 2H), 2.13 (q, 2H); MS m/z 220 (M+1).

Example 2

6-Chloro-2,3,4,9-tetrahydro-1H-carbazol-1-amine

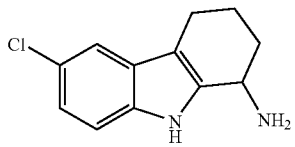

To a solution of to 6-chloro-2,3,4,9-tetrahydro-1H-carbazol-1-one (500 mg, 2.3 mmol) and ammonium acetate (1.8 g, 23 mmol) in methanol (9 mL) was added sodium cyanoborohydride (720 mg, 11.5 mmol). After heating at 60° C. for 15 hours, the mixture was cooled and treated with concentrated hydrochloric acid until pH=1. The organics were removed under reduced pressure and the resulting precipitate was collected by filtration, dissolved in ethyl acetate and methanol, and washed with saturated aqueous sodium carbonate. The phases were separated and the organic phase was concentrated to yield 6-chloro-2,3,4,9-tetrahydro-1H-carbazol-1-amine (260 mg, 52% yield) as a light brown solid. $^1$H-NMR (DMSO-d$_6$): δ 10.90 (s, 1H), 7.34 (m, 1H), 7.27 (d, 1H), 6.97 (dd, 1H), 3.90 (t, 1H), 2.54 (m, 2H), 2.04-1.89 (m, 2H), 1.66 (m, 1H), 1.50 (m, 1H); MS m/z 221 (M+1).

Example 3

6-Bromo-2,3,4,9-tetrahydro-1H-carbazol-1-one

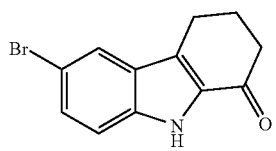

6-Bromo-2,3,4,9-tetrahydro-1H-carbazol-1-one was prepared from bromoaniline and 2-(hydroxymethylene)cyclohexanone in a similar manner as described above to give a brown solid. $^1$H-NMR (CDCl$_3$): δ 8.79 (s, 1H), 7.80 (s, 1H), 7.44 (d, 1H), 7.30 (d, 1H), 2.97 (t, 2H), 2.66 (t, 2H), 2.27 (m, 2H); MS m/z 263, 265 (M+1).

Example 4

6-Bromo-2,3,4,9-tetrahydro-1H-carbazol-1-amine

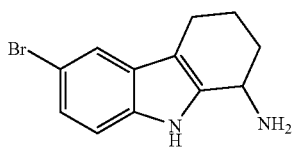

6-Bromo-2,3,4,9-tetrahydro-1H-carbazol-1-amine was prepared in a similar manner as described above to give a solid. ¹H-NMR (CDCl₃): δ 8.58 (s, 1H), 7.55 (s, 1H), 7.20 (m, 2H), 4.12 (t, 1H), 2.70 (t, 2H), 2.24 (m, 1H), 2.05 (m, 1H), 1.92 (m, 3H), 1.66 (m, 1H); MS m/z 266 (M+1).

Example 5

6-Methyl-2,3,4,9-tetrahydro-1H-carbazol-1-one

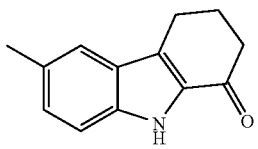

6-Methyl-2,3,4,9-tetrahydro-1H-carbazol-1-one was prepared from p-toluidine and 2-(hydroxymethylene)cyclohexanone in a similar manner as described above to give a tan solid. ¹H-NMR (CDCl₃): δ 8.65 (s, 1H), 7.43 (s, 1H), 7.30 (d, 1H), 7.20 (d, 1H), 2.98 (t, 2H), 2.65 (t, 2H), 2.45 (s, 3H), 2.26 (m, 2H); MS m/z 220 (M+1).

Example 6

6-Methyl-2,3,4,9-tetrahydro-1H-carbazol-1-amine

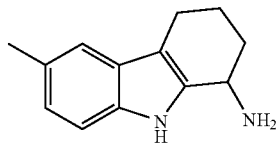

6-Methyl-2,3,4,9-tetrahydro-1H-carbazol-1-amine was prepared in a similar manner as described above to give a solid. ¹H-NMR (DMSO-d₆): δ 10.5 (s, 1H), 7.15 (d, 1H), 7.11 (s, 1H), 6.81 (d, 1H), 3.98 (t, 1H), 3.30 (s, 2H), 2.53 (t, 2H), 2.32 (s, 3H), 2.02 (m, 1H), 1.90 (m, 1H), 1.68 (m, 1H), 1.65 (m, 1H); MS m/z 201 (M+1).

Example 7

2,3,4,9-Tetrahydro-1H-carbazol-1-one

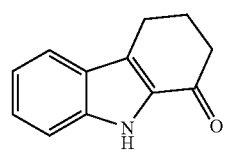

2,3,4,9-Tetrahydro-1H-carbazol-1-one was prepared from aniline (2.9 g, 31 mmol) and 2-(hydroxymethylene)cyclohexanone (3.5 g, 28 mmol) in a similar manner as described above to give 2.5 g (49%). of a brown solid. ¹H-NMR (DMSO-d₆): δ 11.6 (s, 1H), 7.66 (d, 1H), 7.38 (d, 1H), 7.30 (t, 1H), 7.07 (t, 1H), 2.90 (t, 2H), 2.56 (t, 2H), 2.15 (m, 2H); MS m/z 186 (M+1).

Example 8

2,3,4,9-Tetrahydro-1H-carbazol-1-amine hydrochloride

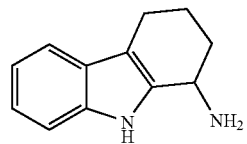

To a solution of 2,3,4,9-tetrahydro-1H-carbazol-1-one (1.5 g, 8.10 mmol) in ethanol (20 mL) was added a solution of hydroxylamine hydrochloride (1.13 g, 16.2 mmol) in water (10 mL) and a solution of sodium acetate (2.19 g, 26.7 mmol) in water (10 mL). The reaction mixture was heated at reflux for 2 h, cooled, and concentrated. The residue was diluted with water and extracted with ethyl acetate (2×100 mL). The organic phase was dried over sodium sulfate, filtered, and concentrated to a brown solid. The oxime was dissolved in THF (80 mL) and lithium aluminium hydride (1.0 M in THF, 24.3 mL) was added dropwise. The reaction was heated at reflux for 7 h and cooled in an ice bath. Methanol was added dropwise until bubbling ceased. The mixture was diluted with aqueous Na/K tartrate, stirred vigorously for 15 min and extracted with ethyl acetate (2×100 mL). The extracts were combined, dried over sodium sulfate, filtered, and concentrated. The crude amine was purified by flash chromatography on silica (2% to 5% methanol/methylene chloride gradient) to provide 2,3,4,9-tetrahydro-1H-carbazol-1-amine as a brown oil. The oil was diluted in diethyl ether and HCl (1.0 M in diethyl ether) was added. The resulting precipitate was collected by filtration to provide 2,3,4,9-tetrahydro-1H-carbazol-1-amine hydrochloride (760 mg, 42%). as a light brown solid. ¹H-NMR (CD₃OD): δ 7.54 (d, 1H), 7.42 (d, 1H), 7.22 (t, 1H), 7.09 (t, 1H), 4.66 (t, 1H), 2.95-2.73 (m, 2H), 2.39-2.28 (m, 1H), 2.18-2.03 (m, 3H); MS m/z (M+1) 187.

Example 9

6-Methoxy-2,3,4,9-tetrahydro-1H-carbazol-1-one

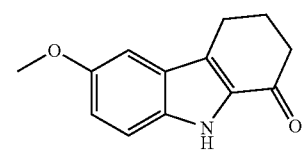

6-Methoxy-2,3,4,9-tetrahydro-1H-carbazol-1-one was prepared from p-anisidine and 2-(hydroxymethylene)cyclohexanone in a similar manner as described above to give a tan solid. ¹H-NMR (CDCl₃): δ 8.77 (br s, 1H), 7.32 (d, 1H), 7.06

(d, 1H), 7.03 (s, 1H), 3.88 (s, 3H), 2.98 (t, 2H), 2.66 (t, 2H), 2.28 (m, 2H); MS m/z 216 (M+1).

Example 10

6-Methoxy-2,3,4,9-tetrahydro-1H-carbazol-1-amine

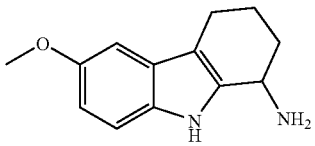

6-Methoxy-2,3,4,9-tetrahydro-1H-carbazol-1-amine was prepared in a similar manner as described above to give a solid. $^1$H-NMR (CDCl$_3$): δ 8.38 (s, 1H), 7.20 (d, 1H), 6.92 (s, 1H), 6.80 (d, 1H), 4.06 (t, 1H), 3.85 (s, 3H), 2.67 (t, 2H), 2.18 (m, 1H), 2.00 (m, 1H), 1.83 (m, 1H), 1.60 (m, 1H); MS m/z 217 (M+1).

Example 11

6-(Trifluoromethyl)-2,3,4,9-tetrahydro-1H-carbazol-1-one

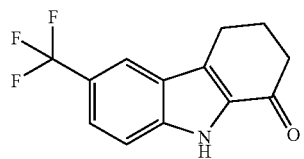

6-(Trifluoromethyl)-2,3,4,9-tetrahydro-1H-carbazol-1-one was prepared from 4-(trifluoromethyl)aniline (5.5 g, 34 mmol) and 2-(hydroxymethylene)cyclohexanone (3.9 g, 31 mmol) in a similar manner as described above to give 2.25 g (29%). of a dark brown solid. $^1$H-NMR (DMSO-d$_6$): δ 12.05 (s, 1H), 8.11 (s, 1H), 7.56 (s, 2H), 3.00 (t, 2H), 2.58 (t, 2H), 2.19-2.13 (m, 2H).

Example 12

2-Bromo-5a,7,8,9,10,10a-hexahydrocyclohepta[b]indol-6(5H)-one

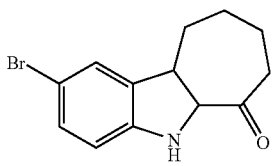

a) Cycloheptane-1,2-dione (4-bromophenyl)hydrazone. To a cold (0° C.) solution of 4-bromoaniline (7.8 g, 46 mmol) in concentrated hydrochloric acid (6 mL) was added sodium nitrite (3.2 g, 46 mmol) dissolved in water (15 mL) portionwise over 10 minutes. The mixture was stirred at 0° C. for 30 minutes. In a separate flask, a cool solution of 2-(hydroxymethylene)cycloheptanone (5.8 g, 41 mmol) in methanol (100 mL) was treated with a solution of sodium acetate (8.6 g, 105 mmol) in water (30 mL). The mixture was stirred at 0° C. for 20 minutes and the diazonium salt slurry was added. The combined mixture was stirred for 30 minutes, collected by filtration, recrystallized from ethanol, and collected by filtration to give cycloheptane-1,2-dione (4-bromophenyl)hydrazone (4.3 g, 48% yield) as an orange solid. $^1$H-NMR (CDCl3): δ 7.38 (d, 2H), 7.10 (d, 2H), 2.68 (d, 2H), 2.64 (d, 2H), 1.83-1.75 (m, 6H); MS m/z (M+1) 278, 280.

b) 2-Bromo-5a,7,8,9,10,10a-hexahydrocyclohepta[b]indol-6(5H)-one. A solution of cycloheptane-1,2-dione (4-bromophenyl)hydrazone (4.3 g, 15 mmol) in hydrochloric acid (30 mL) and acetic acid (8 mL) was heated at 120° C. for 15 minutes. The mixture was cooled slightly and treated with ice water. The resulting precipitate was collected by filtration to give 2-bromo-5a,7,8,9,10,10a-hexahydrocyclohepta[b]indol-6(5H)-one (3.51 g, 86% yield) as brown solid. $^1$H-NMR (DMSO-d$_6$): δ 8.96 (s, 1H), 7.79 (s, 1H), 7.41 (d, 1H), 7.25 (d, 1H), 3.09 (t, 2H), 2.85 (t, 2H), 2.12-1.96 (m, 4H); MS m/z (M+1) 278, 280.

Example 13

2-Bromo-5,5a,6,7,8,9,10,10a-octahydrocyclohepta[b]indol-6-amine hydrochloride

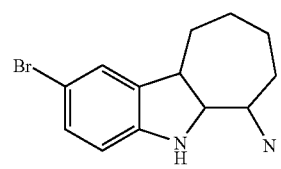

To a solution of to 2-bromo-5a,7,8,9,10,10a-hexahydrocyclohepta[b]indol-6(5H)-one (1.5 g, 5.4 mmol) in ethanol (14 mL) was added solutions of hydroxylamine hydrochloride (750 mg, 11 mmol) in water (10 mL) and sodium acetate (1.46 g, 18 mmol) in water (10 mL). The reaction mixture was heated at reflux for 5 h, cooled and concentrated. The residue was diluted with ethyl acetate and washed with water (2×50 mL). The organic phase was dried over sodium sulfate, filtered and concentrated to a brown solid. The oxime was dissolved in THF (54 mL) and LAH (1.0 M in THF, 16.2 mL, 16.2 mmol) was added dropwise. The reaction was heated at reflux for 4 h and cooled in an ice bath. Methanol was added dropwise until bubbling ceased. The mixture was diluted with aqueous NaHSO$_3$ and stirred vigorously for 15 min and extracted with ethyl acetate (2×150 mL). The extracts were combined, dried over sodium sulfate, filtered and concentrated. The crude amine was purified by flash chromatography on silica (2% to 5% methanol/methylene chloride gradient) to provide 2-bromo-5,5a,6,7,8,9,10,10a-octahydrocyclohepta[b]indol-6-amine as a brown oil. The oil was diluted in diethyl ether and HCl (1.0 M in diethyl ether) was added. The resulting precipitate was collected by filtration to provide 2-bromo-5,5a,6,7,8,9,10,10a-octahydrocyclohepta[b]indol-6-amine hydrochloride (980 mg, 57%). as a light brown solid. $^1$H-NMR (CD$_3$OD): δ 7.65 (s, 1H), 7.28-7.21 (m, 2H), 4.68-4.66 (m, 1H), 3.08-3.01 (m, 1H), 2.84-

2.76 (m, 1H), 2.33-2.25 (m, 1H), 2.15-1.93 (m, 4H), 1.65-1.55 (m, 1H); MS m/z (M−1) 277, 279.

Example 14

7-Bromo-2,3,4,9-tetrahydro-1H-carbazol-1-one

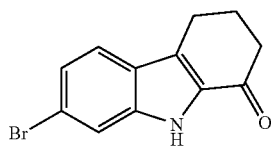

7-Bromo-2,3,4,9-tetrahydro-1H-carbazol-1-one was prepared 3-bromoaniline (7.6 g, 44 mmol) and 2-(hydroxymethylene)cyclohexanone (4.3 g, 34 mmol) in a similar manner as described above and recrystallization from methanol to isolate 7-bromo isomer to give 280 mg (1%). of a light brown solid. $^1$H-NMR (DMSO-$d_6$): δ 8.94 (s, 1H), 7.60 (d, 1H), 7.52 (d, 1H), 7.27-7.25 (m, 1H), 3.01-2.98 (m, 2H), 2.68-2.65 (m, 2H), 2.31-2.24 (m, 2H); MS m/z 263, 265 (M+1).

Example 15

N-Benzyl-2,3,4,9-tetrahydrocarbazole-1-amine hydrochloride salt

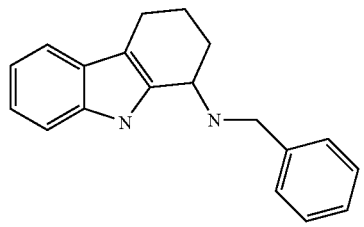

To a solution of 2,3,4,9-tetrahydro-1H-carbazol-1-one (0.1 g, 0.52 mmol) in dichloroethane (5 mL) was added sodium triacetoxyborohydride (0.17 g, 0.80 mmol), acetic acid (0.046 mL, 0.80 mmol) and benzyl amine (0.087 mL, 0.80 mmol). The mixture was stirred at room temperature for 16 hours. The reaction was quenched by adding saturated NaHCO$_3$ (5 mL) and EtOAc (5 mL) and stirred for 30 minutes. The layers were separated, the aqueous layer extracted with EtOAc (2×5 mL), the organic layers combined, dried over Na$_2$SO$_4$, filtered and evaporated. Purification was accomplished by silica gel chromatography with hexanes/ethyl acetate as the eluant to afford yellowish oil. The compound was dissolved in diethyl ether and a solution of HCl in diethyl ethyl ether was added to yield a white precipitate was upon evaporation. Recrystallization from methanol/diethyl ether afforded a white solid (42 mg, 35%). $^1$H-NMR (DMSO-d5): δ 11.2 (s, 1H), 9.70 (s, 1H), 9.58 (s, 1H), 7.64 (d, 2H), 7.43 (m, 5H), 7.14 (t, 1H), 7.02 (t, 1H), 4.67 (s, 1H), 4.29 (s, 2H), 2.71 (m, 2H), 2.22 (m, 2H), 2.08 (m, 1H), 1.82(m, 1H); $^{13}$C-NMR (CDCl$_3$): δ 140.7, 136.2, 135.7, 128.5, 128.1, 127.5, 127.1, 121.5, 119.0, 118.3, 111.2, 110.8, 51.9, 50.4, 30.5, 21.8, 21.0; MS m/z 277 (M).

Example 16

N-(4-Methoxybenzyl)-2,3,4,9-tetrahydro-1H-carbazol-1-amine hydrochloride salt

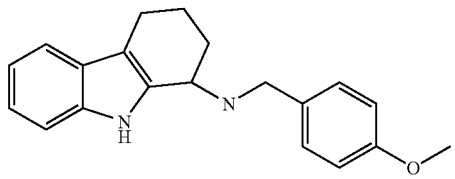

N-(4-Methoxybenzyl)-2,3,4,9-tetrahydro-1H-carbazol-1-amine hydrochloride salt was prepared from 2,3,4,9-tetrahydro-1H-carbazol-1-one (0.1 g, 0.52 mmol) and 4-methoxybenzyl amine (0.07 mL, 0.80 mmol), in a similar manner as described above to give a white solid (0.03 g, 19%). $^1$H-NMR (DMSO-$d_6$): δ 11.1 (s, 1H), 9.35 (s, 1H), 9.27 (s, 1H), 7.53 (d, 2H), 7.49 (d, 1H), 7.40 (d, 1H), 7.15 (t, 1H), 7.02 (t, 1H), 6.99 (d, 2H), 4.62 (s, 1H), 4.24 (s, 2H), 3.76 (s, 3H), 2.72 (m, 2H), 2.18 (m, 2H), 2.10 (m, 1H), 1.82 (m, 1H); MS m/z 305 (M−1).

Example 17

N-(2-Phenylethyl)-2,3,4,9-tetrahydro-1H-carbazol-1-amine hydrochloride salt

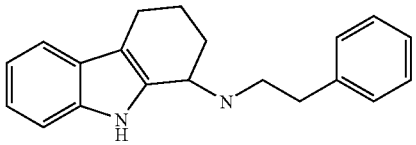

N-(2-Phenylethyl)-2,3,4,9-tetrahydro-1H-carbazol-1-amine hydrochloride salt was prepared from 2,3,4,9-tetrahydro-1H-carbazol-1-one (0.1 g, 0.52 mmol) and phenethyl amine (0.10 mL, 0.80 mmol), in a similar manner as described above to give a white solid (0.04 g, 23%). $^1$H-NMR (CD$_3$OD): δ 7.52 (d, 1H), 7.34 (m, 6H), 7.18 (t, 1H), 7.05 (t, 1H), 4.55 (s, 1H), 3.45 (m, 2H), 3.20 (m, 2H), 3.04 (m, 2H), 2.91 (m, 1H), 2.79 (m, 1H), 2.30 (m, 1H), 2.08 (m, 1H); MS m/z 291 (M+1).

Example 18

N-[(1R)-1-Phenylethyl]-2,3,4,9-tetrahydro-1H-carbazol-1-amine hydrochloride salt

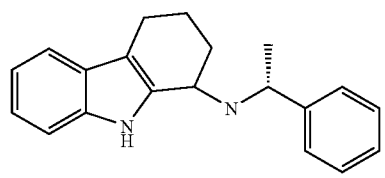

N-[(1R)-1-Phenylethyl]-2,3,4,9-tetrahydro-1H-carbazol-1-amine hydrochloride salt was prepared from 2,3,4,9-tetrahydro-1H-carbazol-1-one (0.1 g, 0.52 mmol) and (R)-α-methylbenzylamine (0.10 mL, 0.80 mmol), in a similar manner as described above to give a mixture of diastereomers as a white solid (0.04 g, 23%). $^1$H-NMR (CDCl$_3$): δ 8.15 (s, 1H), 7.27-7.49 (m, 7H), 7.15 (t, J=7.7 Hz, 1H), 7.08 (t, J=7.7 Hz, 1H), 4.13 (q, J=6.5 Hz, 1H), 4.02 (t, J=7.2 Hz, 1H), 2.70 (t, J=6.8 Hz, 2H), 2.23-2.14 (m, 1H), 2.07-1.97 (m, 1H), 1.86-1.74 (m, 1H), 1.50-1.64 (m, 1H), 1.44 (d, J=6.5 Hz, 3H); MS m/z 291 (M+1).

Example 19

N-Cyclohexyl-2,3,4,9-tetrahydro-1H-carbazol-1-amine hydrochloride salt

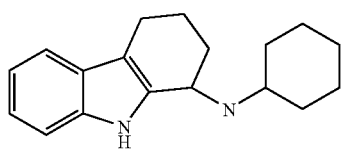

N-Cyclohexyl-2,3,4,9-tetrahydro-1H-carbazol-1-amine hydrochloride salt was prepared from 2,3,4,9-tetrahydro-1H-carbazol-1-one (0.1 g, 0.52 mmol) and cyclohexyl amine (0.09 mL, 0.80 mmol), in a similar manner as described above to give a white solid (0.015 g, 10%). $^1$H-NMR (CDCl$_3$): δ 8.34 (s, 1H), 7.47 (d, 1H), 7.30 (t, 1H), 7.13 (t, 1H), 7.08 (d, 1H), 4.04 (t, 1H), 2.81-2.68 (m, 3H), 2.32-2.25 (m, 1H), 2.07-1.99 (m, 2H), 1.84-1.41 (m, 5H), 1.37-1.10 (m, 6H); MS m/z 269 (M+1).

Example 20

N-(2.3-Dihydro-1H-inden-2-yl)-2,3,4,9-tetrahydro-1H-carbazol-1-amine hydrochloride salt

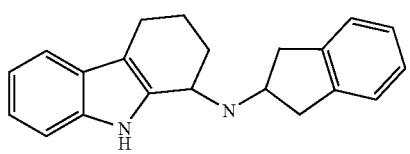

N-(2,3-Dihydro-1H-inden-2-yl)-2,3,4,9-tetrahydro-1H-carbazol-1-amine hydrochloride salt was prepared from 2,3,4,9-tetrahydro-1H-carbazol-1-one (0.1 g, 0.52 mmol) and 2-indaneamine (0.10 mL, 0.80 mmol), in a similar manner as described above to give a white solid (0.07 g, 38%). $^1$H-NMR (CDCl$_3$): δ 8.29 (s, 1H), 7.48 (d, 1H), 7.05-7.47 (m, 7H), 4.06 (t, 1H), 3.97 (m, 1H), 3.24 (d, 1H), 3.19 (d, 1H), 2.89 (d, 1H), 2.79-2.70 (m, 3H), 2.40 (m, 1H), 2.10 (m, 1H), 1.84 (m, 1H), 1.60 (m, 1H); MS m/z 303 (M+1).

Example 21

N-Propyl-2,3,4,9-tetrahydro-1H-carbazol-1-amine hydrochloride salt

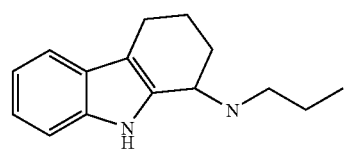

N-Propyl-2,3,4,9-tetrahydro-1H-carbazol-1-amine hydrochloride salt was prepared from 2,3,4,9-tetrahydro-1H-carbazol-1-one (0.1 g, 0.52 mmol) and n-propyl amine (0.065 mL, 0.80 mmol), in a similar manner as described above to give a white solid (0.060 g, 42%). $^1$H-NMR (CDCl$_3$): δ 8.48 (s, 1H), 7.50 (d, 1H), 7.33 (d, 1H), 7.16 (t, 1H), 7.08 (t, 1H), 3.99 (t, 1H), 2.84-2.61 (m, 4H), 2.32-2.23 (m, 1H), 2.10-2.00 (m, 1H), 1.86-1.49 (m, 4H), 0.98 (t, 3H); MS m/z 229 (M+1).

Example 22

N-(2-Methoxyethyl)-2,3,4,9-tetrahydro-1H-carbazol-1-amine hydrochloride salt

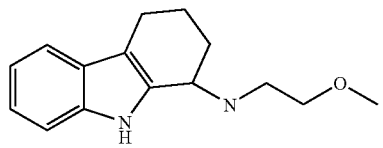

N-(2-Methoxyethyl)-2,3,4,9-tetrahydro-1H-carbazol-1-amine hydrochloride salt was prepared from 2,3,4,9-tetrahydro-1H-carbazol-1-one (0.1 g, 0.52 mmol) and 2-methoxyethanamine (0.07 mL, 0.80 mmol), in a similar manner as described above to give a white solid (0.065 g, 43%). $^1$H-NMR (CDCl$_3$): δ 8.58 (s, 1H), 7.48 (d, 1H), 7.27 (d, 1H), 7.14 (t, 1H), 7.07 (t, 1H), 4.01 (t, 1H), 3.55 (t, 2H), 3.41 (s, 3H), 3.07-2.98 (m, 1H), 2.87-2.78 (m, 1H), 2.72 (t, 2H), 2.26-2.17 (m, 1H), 2.12-2.02 (m, 1H), 1.85-1.65 (m, 2H); MS m/z 245 (M+1).

Example 23

(2R)-2-Phenyl-2-(2,3,4,9-tetrahydro-1H-carbazol-1-ylamino)ethanol hydrochloride salt

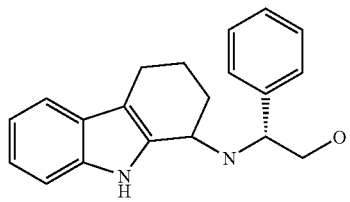

(2R)-2-Phenyl-2-(2,3,4,9-tetrahydro-1H-carbazol-1-ylamino)ethanol hydrochloride salt was prepared from 2,3,4,9-tetrahydro-1H-carbazol-1-one (0.1 g, 0.52 mmol) and (2R)-2-amino-2-phenylethanol (0.11 mL, 0.80 mmol), in a similar manner as described above to give a white solid (0.01 g, 5%). ¹H-NMR (CDCl₃): δ 8.47 (s, 1H), 7.47 (d, 1H), 7.41-7.26 (m, 6H), 7.15 (t, 1H), 7.08 (t, 1H), 4.06-4.00 (m, 2H), 3.80 (dd, 1H), 3.61 (dd, 1H), 3.07-2.98 (m, 1H), 2.67 (t, 2H), 2.04-1.87 (m, 2H), 1.77-1.66 (m, 1H), 1.57-1.47 (m, 1H); MS m/z 305 (M−1).

Example 24

N-[(1S)-1-Methyl-3-Phenylpropyl]-2,3,4,9-tetrahydro-1H-carbazol-1-aminehydrochloride salt

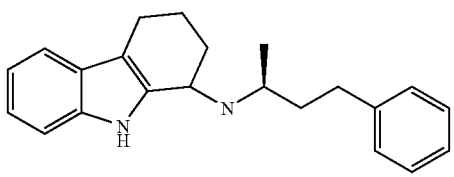

N-[(1S)-1-Methyl-3-phenylpropyl]-2,3,4,9-tetrahydro-1H-carbazol-1-amine hydrochloride salt was prepared from 2,3,4,9-tetrahydro-1H-carbazol-1-one (0.1 g, 0.52 mmol) and (2R)-4-phenylbutan-2-amine (0.12 mL, 0.80 mmol), in a similar manner as described above to give a white solid (0.01 g, 4%). ¹H-NMR (CD₃OD): δ 7.50 (d, 1H), 7.38 (d, 1H), 7.34-7.21 (m, 5H), 7.18 (t, 1H), 7.05 (t, 1H), 4.74 (t, 1H), 3.60 (m, 1H), 2.92-2.70 (m, 4H), 2.29-2.13 (m, 3H), 2.06-1.89 (m, 3H), 1.49 (d, 3H); MS m/z 318 (M).

Example 25

N-(1,3-Benzodioxol-5-ylmethyl)-2,3,4,9-tetrahydro-1H-carbazol-1-amine hydrochloride salt

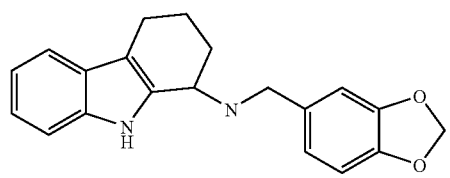

N-(1,3-Benzodioxol-5-ylmethyl)-2,3,4,9-tetrahydro-1H-carbazol-1-amine hydrochloride salt was prepared from 2,3,4,9-tetrahydro-1H-carbazol-1-one (0.1 g, 0.52 mmol) and 1-(1,3-benzodioxy-5-yl)methaneamine (0.10 mL, 0.80 mmol), in a similar manner as described above to give a white solid (0.02 g, 9%). ¹H-NMR (DMSO-d₆): δ 10.70 (s, 1H), 9.18 (d, 2H), 7.40 (m, 3H), 7.13-6.88 (m, 4H), 6.00 (s, 2H), 3.90 (m, 1H), 2.59 (m, 2H), 2.00 (m, 2H), 1.71 (m, 2H); MS m/z 321 (M+1).

Example 26

6-Bromo-N-(2-phenylethyl)-2,3,4,9-tetrahydro-1H-carbazol-1-amine hydrochloride salt

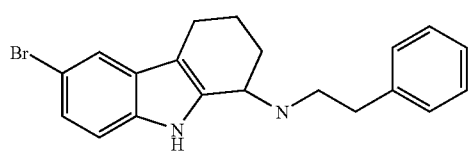

6-Bromo-N-(2-phenylethyl)-2,3,4,9-tetrahydro-1H-carbazol-1-amine hydrochloride salt was prepared from 6-bromo-2,3,4,9-tetrahydro-1H-carbazol-1-one (0.1 g, 0.38 mmol) and phenethyl amine (0.10 mL, 0.57 mmol), in a similar manner as described above to give a white solid (0.067 g, 44%). ¹H-NMR (CD₃OD): δ 7.66 (s, 1H), 7.38-7.25 (m, 7H), 4.57 (t, 1H), 3.50-3.37 (m, 2H), 3.07-3.00 (m, 2H), 2.94-2.86 (m, 1H), 2.77-2.70 (m, 1H), 2.43-2.20 (m, 2H), 2.08-2.04 (m, 2H); MS m/z 367, 369 (M−1).

Example 27

(1R)-6-Bromo-N-(2,3-dihydro-1H-inden-2-yl)-2,3,4,9-tetrahydro-1H-carbazol-1-amine hydrochloride salt

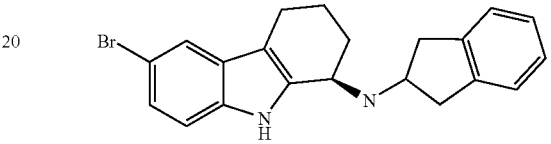

(1R)-6-Bromo-N-(2,3-dihydro-1H-inden-2-yl)-2,3,4,9-tetrahydro-1H-carbazol-1-amine hydrochloride salt was prepared by separation of racemic 6-bromo-N-(2,3-dihydro-1H-inden-2-yl)-2,3,4,9-tetrahydro-1H-carbazol-1-amine by Super critical Fluid Chromatography (hereinafter "SFC") (Diacel AD-H, Chiral Technologies, 30% methanol, 3000 psi, 40° C., 2 mL/min, retention time: 16.6 min.) The oil obtained was converted to the HCl salt to give a white solid. ¹H-NMR (DMSO-d₆): δ 11.4 (s, 1H), 9.61 (s, 1H), 9.42 (s, 1H), 7.69 (s, 1H), 7.36 (d, 1H), 7.35-7.19 (m, 5H), 4.68 (t, 1H), 4.32 (m, 1H), 3.47 (dd, 1H), 3.32 (m, 3H), 2.74 (m, 1H), 2.65 (m, 1H), 2.18 (m, 2H), 2.01 (m, 1H), 1.87 (m, 1H); MS m/z 379, 381 (ES-1).

Example 28

(1S)-6-Bromo-N-(2.3-dihydro-1H-inden-2-yl)-2,3,4,9-tetrahydro-1H-carbazol-1-amine hydrochloride salt

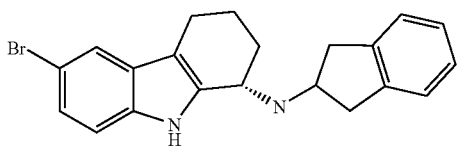

(1S)-6-Bromo-N-(2,3-dihydro-1H-inden-2-yl)-2,3,4,9-tetrahydro-1H-carbazol-1-amine hydrochloride salt was prepared by separation of racemic 6-bromo-N-(2,3-dihydro-1H-inden-2-yl)-2,3,4,9-tetrahydro-1H-carbazol-1-amine by preparative SFC (Diacel AD-H, Chiral Technologies, 30% methanol, 3000 psi, 40° C., 2 mL/min, retention time: 8.6 min.) The oil obtained was converted to the HCl salt to give a white solid. ¹H-NMR (DMSO-d₆): δ 11.4 (s, 1H), 9.61 (s, 1H), 9.42 (s, 1H), 7.69 (s, 1H), 7.36 (d, 1H), 7.35-7.19 (m, 5H), 4.68 (t, 1H), 4.32 (m, 1H), 3.47 (dd, 1H), 3.32 (m, 3H), 2.74 (m, 1H), 2.65 (m, 1H), 2.18 (m, 2H), 2.01 (m, 1H), 1.87 (m, 1H); MS m/z 379, 381 (ES-1).

Example 29

N-Benzyl-6-bromo-2,3,4,9-tetrahydro-1H-carbazol-1-amine hydrochloride salt

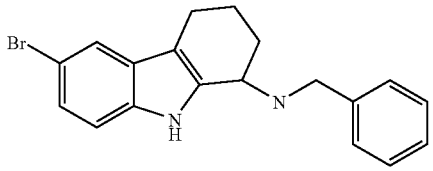

N-Benzyl-6-bromo-2,3,4,9-tetrahydro-1H-carbazol-1-amine hydrochloride salt was prepared from 6-bromo-2,3,4,9-tetrahydro-1H-carbazol-1-one (0.1 g, 0.38 mmol) and benzyl amine (0.062 mL, 0.57 mmol), in a similar manner as described above to give a white solid (0.042 g, 31%). $^1$H-NMR (CD$_3$OD): δ 7.67 (s, 1H), 7.54-7.45 (m, 5H), 7.30 (q, 2H), 4.69 (t, 1H), 4.42 (m, 2H), 2.86 (t, 1H), 2.79-2.69 (m, 1H), 2.34-2.27 (m, 2H), 2.04 (m, 2H); MS m/z 354, 356 (M+1); Anal. Calc'd for C$_{19}$H$_{20}$BrN$_2$Cl: C, 58.25; H, 5.15; N, 7.15. Found: C, 58.56; H, 5.17; N, 7.14.

Example 30

6-Bromo-N-[(1R)-1-phenylethyl]-2,3,4,9-tetrahydro-1H-carbazol-1-amine hydrochloride salt

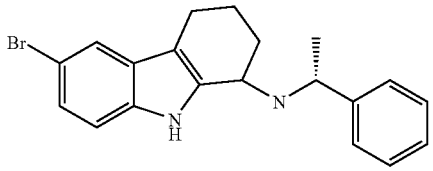

6-Bromo-N-[(1R)-1-phenylethyl]-2,3,4,9-tetrahydro-1H-carbazol-1-amine hydrochloride salt was prepared from 6-bromo-2,3,4,9-tetrahydro-1H-carbazol-1-one (0.1 g, 0.38 mmol) and (R)-α-methylbenzylamine (0.07 mL, 0.57 mmol), in a similar manner as described above to give a white solid (0.08 g, 52%). $^1$H-NMR (CD$_3$OD): δ 7.65 (m, 3H), 7.56-7.46 (m, 3H), 7.36 (d, J=8.7 Hz, 1H), 7.28 (d, J=8.7 Hz, 1H), 4.76 (q, J=7.8 Hz, 1H), 4.48 (t, J=4.2 Hz, 1H), 2.90-2.82 (m, 1H), 2.73-2.63 (m, 1H), 2.11-2.00 (m, 4H), 1.43 (d, J=6.6 Hz, 3H); $^{13}$C-NMR (DMSO-d$_6$): δ 138.6, 135.0, 130.3, 129.3, 129.2, 128.6, 128.3, 125.2, 121.3, 113.9, 113.6, 111.8, 56.0, 49.7, 26.1, 20.6, 20.2, 19.2; MS m/z 367, 369 (M−1).

Example 31A

(1R)-6-bromo-N-[(1R)-1-phenylethyl]-2,3,4,9-tetrahydro-1 H-carbazol-1-amine hydrochloride salt

(1R)-6-Bromo-N-[(1R)-1-phenylethyl]-2,3,4,9-tetrahydro-1H-carbazol-1-amine hydrochloride salt was prepared by separation of diastereomeric 6-bromo-N-[(1R)-1-phenylethyl]-2,3,4,9-tetrahydro-1H-carbazol-1-amine by SFC (Berger Amino, Chiral Technologies, 10% methanol, (2% diethyl amine/10% chloroform) 1500 psi, 50° C., 2 mL/min, retention time: 17.5 min.) The oil obtained was converted to the HCl salt to give a white solid. [α]$^{25}$=160 (c 0.20, MeOH); $^1$H-NMR (DMSO-d$_6$): δ 11.6 (s, 1H), 9.85 (s, 1H), 9.30 (s, 1H), 7.80 (d, J=6.8 Hz, 1H), 7.70 (d, J=1.8 Hz, 1H), 7.52-7.45 (m, 3H), 7.43 (d, J=8.6 Hz, 1H), 7.29 (dd, J=6.8 Hz, J=1.8 Hz, 1H), 4.78 (m, J=6.4 Hz, 1H), 4.60 (m, 1H), 2.77-2.65 (m, 2H), 2.20-2.05 (m, 1H), 2.05-1.95 (m, 2H), 1.88-1.80 (m, 1H), 1.71 (d, J=6.8 Hz, 3H); MS m/z 367, 369 (M−1); Anal. Calcd. For C$_{20}$H$_{22}$BrN$_2$Cl: C, 59.20; H, 5.46; N, 6.90; Cl, 8.69. Found: C, 59.34; H, 5.45; N, 6.87; Cl, 8.67.

Alternatively (1R)-6-Bromo-N-[(1R)-1-phenylethyl]-2,3,4,9-tetrahydro-1H-carbazol-1-amine could by synthesized using a enantioselective route:

Example 31B

(1R)-6-bromo-N-[(1R)-1-phenylethyl]-2,3,4,9-tetrahydro-1H-carbazol-1-amine hydrochloride A mixture of 6-bromo-2,3,4,9-tetrahydro-1H-carbazol-1-one (50 mg, 0.19 mmol), (R)-α-methylbenzylamine (23 mg, 0.19 mmol), and p-toluenesulfonic acid (5 mg) in toluene (15 mL) were refluxed with a Dean-Stark trap for 16 hours. The mixture was concentrated and the residue dried under high vacuum. The residue was dissolved in dichloromethane (3 mL) before formic acid (0.036 mL, 0.95 mmol), triethylamine (0.052 mL, 0.38 mmol), and (S)-RuCl[(1R,2R)-p-TsNCH(C$_6$He)CH(C$_6$H$_6$)NH$_2$](η-benzene) (16 mg, 0.038 mmol) were added and stirred for one hour at room temperature. (S)-RuCl[(1R,2R)-p-TsNCH(C$_6$H$_6$)CH(C$_6$H$_6$)NH$_2$](η-benzene) was prepared as described in *Journal of American Chemical Society* 1996, 118, 2521-2522, and references therein, incorporated herein by reference with regard to such synthesis. The mixture was diluted with dichloromethane (10 mL) and washed with saturated sodium bicarbonate (10 mL). The organic phase was applied directly to a silica gel chromatography column and was eluted with 5% ethyl acetate in dichloromethane. Appropriate fractions were concentrated to yield 48 mg (68%, 90% de) of (1R)-6-bromo-N-[(1R)-1-phenylethyl]-2,3,4,9-tetrahydro-1H-carbazol-1-amine. $^1$H NMR (DMSO-d$_6$): δ 10.84 (s, 1H), 7.47 (m, 3H), 7.32 (m, 3H), 7.22 (t, 1H), 7.12 (d, 1H), 4.10 (m, 1H), 3.78 (m, 1H), 2.50 (m under DMSO, 2H), 2.16 (bs, 1H), 1.87 (m, 1H), 1.76 (m, 1H), 1.59 (m, 1H), 1.49 (m, 1H), 1.31 (d, 3H); MS m/z 368 (M−1). (1R)-6-bromo-N-[(1R)-1-phenylethyl]-2,3,4,9-tetrahydro-1H-carbazol-1-amine (48 mg, 90% de) was dissolved in ethyl ether (2 mL) before 1 M HCl in ether (2 mL) was added dropwise. The resulting precipitate was collected by filtration to yield 36 mg of a yellow solid. The solid was dissolved in hot methanol (2 mL). The solution was allowed to cool and ethyl ether added dropwise until the solution became cloudy. Crystals precipitated and were collected by filtration to yield 16 mg (30%, 100% de) of (1R)-6-bromo-N-[(1R)-1-phenylethyl]-2,3,4,9-tetrahydro-1H-carbazol-1-amine hydrochloride. $^1$H NMR (DMSO-d$_6$): δ 11.66 (s, 1H), 9.86 (bs, 1H), 9.29 (m, 1H), 7.76 (d, 2H), 7.66 (s, 1H), 7.36-7.48 (m, 4H), 7.24 (d, 1H), 4.73 (m, 1H), 4.55 (m, 1H), 2.63 (m, 2H), 2.09 (m, 1H), 1.96 (m, 2H), 1.79 (m, 1H), 1.67 (d, 3H). MS m/z 367, 369 (M−1).

Example 32

(1S)-6-Bromo-N-[(1R)-1-Phenylethyl]-2,3,4,9-tetrahydro-1H-carbazol-1-amine hydrochloride salt

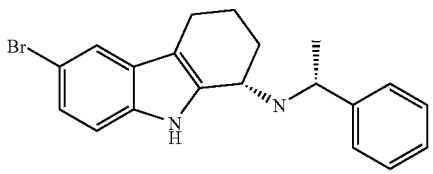

(1S)-6-bromo-N-[(1R)-1-phenylethyl]-2,3,4,9-tetrahydro-1H-carbazol-1-amine hydrochloride salt was prepared by separation of diastereomeric 6-bromo-N-[(1R)-1-phenylethyl]-2,3,4,9-tetrahydro-1H-carbazol-1-amine by SFC (Berger Amino, Chiral Technologies, 10% methanol, (2% diethyl amine/10% chloroform) 1500 psi, 50° C., 2 mL/min, retention time: 19.8 min.) The oil obtained was converted to the HCl salt to give a white solid. $[\alpha]^{25} = -4.3$ (c 0.23, MeOH); $^1$H-NMR (DMSO-$d_6$): δ 11.6 (s, 1H), 10.08 (s, 1H), 9.64 (s, 1H), 7.86 (d, J=6.8 Hz, 1H), 7.70 (d, J=1.8 Hz, 1H), 7.55-7.45 (m, 3H), 7.42 (d, J=8.6 Hz, 1H), 7.29 (dd, J=6.8 Hz, J=1.8 Hz, 1H), 4.75 (m, J=6.4 Hz, 1H), 4.57 (m, 1H), 3.47-3.37 (m, 2H), 2.70-2.64 (m, 2H), 2.13-2.07 (m, 2H), 1.65 (d, J=6.8 Hz, 3H); MS m/z 367, 369 (M−1); Anal. Calcd. For $C_{20}H_{22}BrN_2Cl$: C, 59.20; H, 5.46; N, 6.90. Found: C, 59.29; H, 5.55; N, 6.92.

Example 33

6-Bromo-N-(1-methyl-1-phenylethyl)-2,3,4,9-tetrahydro-1H-carbazol-1-amine hydrochloride salt

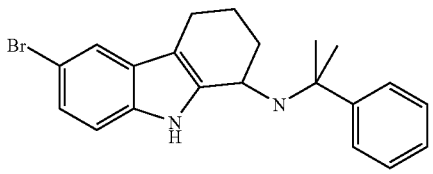

To a solution of 6-bromo-2,3,4,9-tetrahydro-1H-carbazol-1-one (500 mg, 1.9 mmol) in methanol (20 mL) was added sodium borohydride (144 mg, 3.8 mmol) portionwise. The reaction mixture was stirred for one hour and quenched with water (5 mL). The reaction was concentrated, diluted with methylene chloride, and washed with water. The organic phase was concentrated and the crude alcohol purified by flash chromatography on silica (5% to 30% ethyl acetate/hexanes gradient) to provide 6-bromo-2,3,4,9-tetrahydro-1H-carbazol-1-ol (255 mg, 50%). as a light brown solid. $^1$H-NMR (DMSO-$d_6$): δ 10.99 (s, 1H), 7.54 (d, 1H), 7.25 (d, 1H), 7.12 (dd, 1H), 5.18 (d, 1H), 4.75-4.70 (m, 1H), 2.64-2.53 (m, 2H), 2.02-1.91 (m, 2H), 1.77-1.66 (m, 2H); MS m/z (M+1) 267.

6-bromo-N-(1-methyl-1-phenylethyl)-2,3,4,9-tetrahydro-1H-carbazol-1-amine hydrochloride salt was prepared by dissolving 6-bromo-2,3,4,9-tetrahydro-1H-carbazol-1-ol (0.04 g, 0.15 mmol) in cumyl amine (0.5 mL) in the presence of p-toluene sulfonic acid in a 2 mL reaction vessel with a stir bar. The vessel was sealed and heated in a Personal Chemistry Microwave Synthesizer for 10 min. at 150° C. The crude reaction was purified by flash chromatography on silica (5% to 25% ethyl acetate/hexanes gradient) and converted to the HCl salt to afford a white solid (14 mg, 22%). $^1$H-NMR (DMSO-$d_6$): δ 11.20 (s, 1H), 9.50 (s, 1H), 9.06 (s, 1H), 7.79 (d, J=7.0 Hz, 2H), 7.64 (d, J=1.8 Hz, 1H), 7.49 (t, J=7.0 Hz, 2H), 7.43 (t, J=7.0 Hz, 1H), 7.37 (d, J=8.6 Hz, 2H), 7.24 (dd, J=8.6 Hz, J=1.8 Hz, 1H), 4.47 (s, 1H), 2.67-2.60 (m, 1H), 2.47-2.20 (m, 1H), 2.00 (s, 3H), 1.81 (m, 4H) 1.59-1.34 (m, 3H); MS m/z 381, 383 (M−1); Anal. Calcd. For $C_{21}H_{24}BrN_2Cl$: C, 60.08; H, 5.76; N, 6.67. Found: C, 60.01; H, 5.84; N, 6.67.

Example 34

6-Bromo-N-[(1S)-1-phenylethyl]-2,3,4,9-tetrahydro-1H-carbazol-1-amine hydrochloride salt

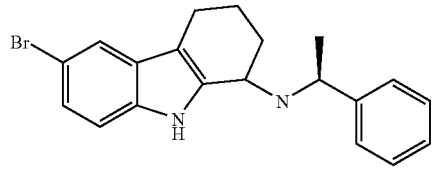

6-Bromo-N-[(1S)-1-phenylethyl]-2,3,4,9-tetrahydro-1H-carbazol-1-amine hydrochloride salt was prepared in an identical manner as described above to give a white solid. $^1$H-NMR (DMSO-$d_6$): δ 11.6 (s, 1H), 9.85 (s, 1H), 9.30 (s, 1H), 7.77 (d, J=6.8 Hz, 1H), 7.68 (d, J=1.8 Hz, 1H), 7.49-7.40 (m, 3H), 7.39 (d, J=8.6 Hz, 1H), 7.29 (dd, J=6.8 Hz, J=1.8 Hz, 1H), 4.78 (m, J=6.4 Hz, 1H), 4.60 (t, J=4.4 Hz, 1H), 2.77-2.65 (m, 2H), 2.20-2.05 (m, 1H), 2.05-1.95 (m, 2H), 1.88-1.80 (m, 1H), 1.71 (d, J=6.8 Hz, 3H); MS m/z 367, 369 (M−1).

Example 35

(1S)-6-Bromo-N-[(1S)-1-phenylethyl]-2,3,4,9-tetrahydro-1H-carbazol-1-amine hydrochloride salt

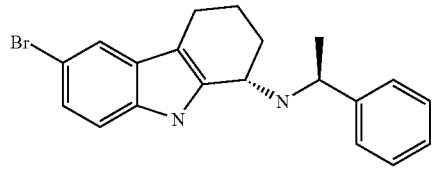

(1S)-6-Bromo-N-[(1S)-1-phenylethyl]-2,3,4,9-tetrahydro-1H-carbazol-1-amine hydrochloride salt was prepared by separation of diastereomeric 6-bromo-N-[(1S)-1-phenylethyl]-2,3,4,9-tetrahydro-1H-carbazol-1-amine by SFC (Berger Amino, Chiral Technologies, 10% methanol, (2% diethyl amine/10% chloroform) 1500 psi, 50° C., 2 mL/min, retention time: 17.5 min.) The oil obtained was converted to the HCl salt to give a white solid. $^1$H-NMR (DMSO-$d_6$): δ 11.6 (s, 1H), 9.85 (s, 1H), 9.30 (s, 1H), 7.80 (d, J=6.8 Hz, 1H), 7.70 (d, J=1.8 Hz, 1H), 7.52-7.45 (m, 3H), 7.43 (d, J=8.6 Hz, 1H), 7.29 (dd, J=6.8 Hz, J=1.8 Hz, 1H), 4.78 (m, J=6.4 Hz, 1H), 4.60 (m, 1H), 2.77-2.65 (m, 2H), 2.20-2.05 (m, 1H), 2.05-1.95 (m, 2H), 1.88-1.80 (m, 1H), 1.71 (d, J=6.8 Hz, 3H); MS m/z 367, 369 (M−1); Anal. Calcd. For C$_{20}$H$_{22}$BrN$_2$Cl: C, 59.20; H, 5.46; N, 6.90. Found: C, 59.36; H, 5.58; N, 6.97.

Example 36

(1R)-6-Bromo-N-[(1S)-1-phenylethyl]-2,3,4,9-tetrahydro-1H-carbazol-1-amine hydrochloride salt

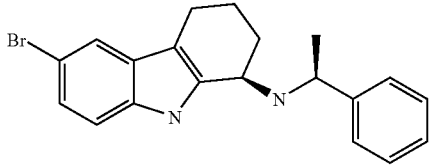

(1R)-6-Bromo-N-[(1S)-1-phenylethyl]-2,3,4,9-tetrahydro-1H-carbazol-1-amine hydrochloride salt was prepared by separation of diastereomeric 6-bromo-N-[(1S)-1-phenylethyl]-2,3,4,9-tetrahydro-1H-carbazol-1-amine by SFC (Berger Amino, Chiral Technologies, 10% methanol, (2% diethyl amine/10% chloroform) 1500 psi, 50° C., 2 mL/min, retention time: 19.8 min.) The oil obtained was converted to the HCl salt to give a white solid. $^1$H-NMR (DMSO-d$_6$): δ 11.6 (s, 1H), 10.08 (s, 1H), 9.64 (s, 1H), 7.86 (d, J=6.8 Hz, 1H), 7.70 (d, J=1.8 Hz, 1H), 7.55-7.45 (m, 3H), 7.42 (d, J=8.6 Hz, 1H), 7.29 (dd, J=6.8 Hz, J=1.8 Hz, 1H), 4.75 (m, J=6.4 Hz, 1H), 4.57 (t, J=4.4 Hz, 1H), 3.47-3.37 (m, 2H), 2.70-2.64 (m, 2H), 2.13-2.07 (m, 2H) 1.71 (d, J=6.8 Hz, 3H); MS m/z 367, 369 (M−1); Anal. Calcd. For C$_{20}$H$_{22}$BrN$_2$Cl: C, 59.20; H, 5.46; N, 6.90. Found: C, 59.32; H, 5.58; N, 6.97.

Example 37

6-Bromo-N-methyl-N-(2-phenylethyl)-2,3,4,9-tetrahydro-1H-carbazol-1-amine hydrochloride salt

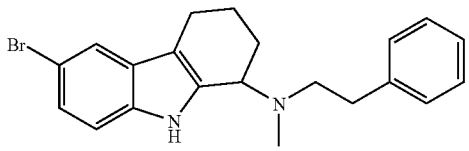

6-Bromo-N-methyl-N-(2-phenylethyl)-2,3,4,9-tetrahydro-1H-carbazol-1-amine hydrochloride salt was prepared from 6-bromo-N-(2-phenylethyl)-2,3,4,9-tetrahydro-1H-carbazol-1-amine hydrochloride salt (0.05 g, 0.12 mmol), diisopropylethyl amine (0.04 mL, 0.25 mmol) and methyl iodide (0.008 mL, 0.12 mmol) in THF (2.0 mL). The reagents were added to a round bottom flask and allowed to stir for 12 hrs. at room temperature under inert atmosphere. The solvent was evaporated, ethyl acetate was added (10 mL), the organics were washed with water (2.0 mL) and sat. NaCl (2.0 mL), dried over Na$_2$SO$_4$, filtered and evaporated to leave an oily residue. Purification by flash chromatography with gradient 10-50% ethyl acetate/hexanes eluent afforded a clear oil that was converted to the HCl salt to give a white solid (0.01 g, 20%). $^1$H-NMR (CDCl$_3$): δ 8.30 (s, 1H), 7.53 (d, 2H), 7.38-7.10 (m, 5H), 6.89 (d, 1H), 4.09 (m, 1H), 3.04-2.95 (m, 1H), 2.90-2.80 (m, 2H), 2.70-2.55 (m, 3H), 2.48 (s, 3H), 2.11-1.99 (m, 2H), 1.70-1.60 (m, 2H).

Example 38

6-Bromo-9-methyl-N-(2-phenylethyl)-2,3,4,9-tetrahydro-1H-carbazol-1-amine hydrochloride salt

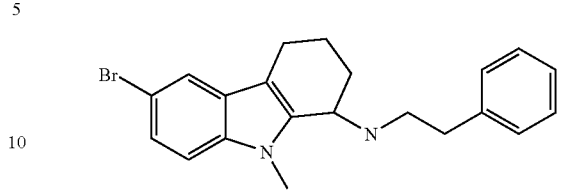

6-Bromo-9-methyl-N-(2-phenylethyl)-2,3,4,9-tetrahydro-1H-carbazol-1-amine hydrochloride salt was prepared by addition of methyl iodide (0.016 mL, 0.25 mmol) to a solution of 6-bromo-N-(2-phenylethyl)-2,3,4,9-tetrahydro-1H-carbazol-1-amine hydrochloride salt (0.05 g, 0.12 mmol) and sodium hydride (0.04 mL, 0.25 mmol) in THF (2.0 mL) that was under inert atmosphere and cooled to 0° C. The mixture was allowed to warm to room temperature and stirred for 12 hrs. The reaction was quenched with saturated ("sat.") ammonium chloride ("NH$_4$Cl") (2.0 mL), ethyl acetate was added (10 mL), the organic layer was separated and washed with sat. NaCl (2.0 mL), dried over sodium sulfate ("Na$_2$SO$_4$"), filtered and evaporated to leave an oily residue. Purification by flash chromatography with 10-50% gradient ethyl acetate/hexanes eluent afforded a clear oil that was converted to the HCl salt to give a white solid (0.005 g, 9%). $^1$H-NMR (CDCl$_3$): δ 7.57 (s, 1H), 7.31-7.21 (m, 7H), 7.09 (d, 1H), 3.86 (m, 1H), 3.53 (s, 3H), 3.19-3.13 (m, 1H), 2.94-2.87 (m, 1H), 2.84-2.80 (m, 2H), 2.74-2.67 (m, 1H), 2.55-2.47 (m, 1H), 2.17-2.11 (m, 1H), 1.83-1.70 (m, 3H); MS m/z 381, 383 (M−1).

Example 39

6-Bromo-N-[(2R)-2-phenylpropyl]-2,3,4,9-tetrahydro-1H-carbazol-1-amine hydrochloride salt

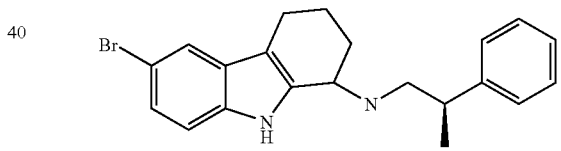

6-Bromo-N-[(2R)-2-phenylpropyl]-2,3,4,9-tetrahydro-1H-carbazol-1-amine hydrochloride salt was prepared from 6-bromo-2,3,4,9-tetrahydro-1H-carbazol-1-one (0.1 g, 0.38 mmol) and (2R)-2-phenylpropan-1-amine (0.075 mL, 0.57 mmol), in a similar manner as described above to give a white solid (0.030 g, 19%). $^1$H-NMR (DMSO-d$_6$): δ 11.6 (s, 1H), 9.60 (s, 1H), 9.28 (s, ½H), 9.06 (s, ½H), 7.67 (d, 1H), 7.39-7.20 (m, 6H), 7.11 (s, 1H), 4.65 (m, 1H), 3.30-3.15 (m, 3H), 2.68-2.60 (m, 2H), 2.23-2.15 (m, 1H), 2.10-2.97 (m, 2H), 1.78-1.70 (m, 1H), 1.32 (dd, 3H); MS m/z 381, 383 (M−1).

Example 40

6-Methyl-N-(2-phenylethyl)-2,3,4,9-tetrahydro-1H-carbazol-1-amine hydrochloride salt

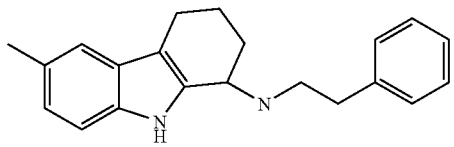

6-Methyl-N-(2-phenylethyl)-2,3,4,9-tetrahydro-1H-carbazol-1-amine hydrochloride salt was prepared from 6-methyl-2,3,4,9-tetrahydro-1H-carbazol-1-one (0.1 g, 0.5 mmol) and phenethyl amine (0.095 mL, 0.75 mmol), in a similar manner as described above to give a white solid (0.04 g, 23%). $^1$H-NMR (CD$_3$OD): δ 7.38-7.22 (m, 7H), 7.00 (dd, 1H), 4.55 (t, 1H), 3.51-3.40 (m, 2H), 3.07-3.00 (m, 2H), 2.94-2.84 (m, 1H), 2.77-2.66 (m, 1H), 2.39 (s, 3H), 2.32-2.14 (m, 2H), 2.09-2.00 (m, 2H); MS m/z 303 (M−1).

Example 41

N-(2.3-Dihydro-1H-inden-2-yl)-6-methyl-2,3,4,9-tetrahydro-1H-carbazol-1-amine hydrochloride-salt

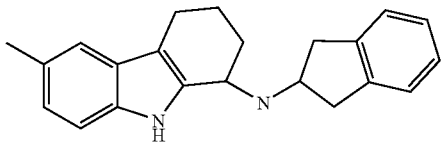

N-(2,3-Dihydro-1H-inden-2-yl)-6-methyl-2,3,4,9-tetrahydro-1H-carbazol-1-amine hydrochloride salt was prepared from 6-methyl-2,3,4,9-tetrahydro-1H-carbazol-1-one (0.1 g, 0.5 mmol) and 2-indaneamine (0.10 mL, 0.75 mmol), in a similar manner as described above to give a white solid (0.027 g, 15%). $^1$H-NMR (CD$_3$OD): δ 7.36-7.22 (m, 6H), 7.00 (dd, 1H), 4.70 (t, 1H), 4.43 (m, 1H), 3.66 (dd, 1H), 3.44 (dd, 1H), 3.28-3.12 (m, 2H), 2.95-2.86 (m, 1H), 2.80-2.69 (m, 1H), 2.40 (s, 3H), 2.32-2.25 (m, 2H), 2.09-2.00 (m, 2H); MS m/z 184 (M−133).

Example 42

6-Methyl-N-[(1R)-1-phenylethyl]-2,3,4,9-tetrahydro-1H-carbazol-1-amine hydrochloride salt

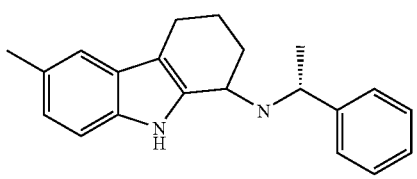

6-Methyl-N-[(1R)-1-phenylethyl]-2,3,4,9-tetrahydro-1H-carbazol-1-amine hydrochloride salt was prepared from 6-methyl-2,3,4,9-tetrahydro-1H-carbazol-1-one (0.1 g, 0.5 mmol) and (R)-α-methylbenzylamine (0.07 mL, 0.75 mmol), in a similar manner as described above to give a white solid (0.075 g, 44%). $^1$H-NMR (CDCl$_3$): δ 8.05 (s, 1H), 7.50-7.18 (m, 7H), 7.36 (d, J=8.1 Hz, 1H), 4.13 (q, J=5.77 Hz, 1H), 3.99 (t, J=6.3 Hz, 1H), 2.44 (s, 3H), 2.20-2.13 (m, 1H), 2.05-1.95 (m, 1H), 1.64-1.48 (m, 4H), 1.42 (d, J=6.3 Hz, 3H); MS m/z 184 (M−121).

Example 43

(1R)-Methyl-N-[(1R)-1-phenylethyl]-2,3,4,9-tetrahydro-1H-carbazol-1-amine hydrochloride salt

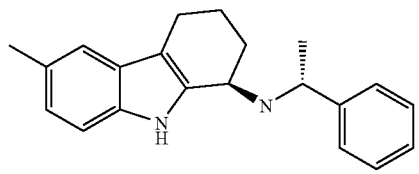

(1R)-6-Methyl-N-[(1R)-1-phenylethyl]-2,3,4,9-tetrahydro-1H-carbazol-1-amine hydrochloride salt was prepared by separation of diastereomeric 6-methyl-N-[(1R)-1-phenylethyl]-2,3,4,9-tetrahydro-1H-carbazol-1-amine the free base by SFC (Berger Amino, 8% methanol, 1500 psi, 40° C., 2 mL/min, retention time: 8.7 min.) The oil obtained was converted to the HCl salt to give a white solid. [α]$^{25}$=153 (c 0.23, MeOH); $^1$H-NMR (CD$_3$OD): δ 7.63 (d, J=7.6 Hz, 2H), 7.55-7.46 (m, 3H), 7.29 (d, J=8.0 Hz, 1H), 7.27 (s, 1H), 7.02 (d, J=8.4 Hz, 1H), 4.75 (q, J=7.2 Hz, 1H), 4.43 (m, 1H), 2.85 (dt, J=16.4 Hz, J=4.0 Hz, 1H), 2.67 (dt, J=16.4 Hz, J=4.0 Hz, 1H), 2.40 (s, 3H), 2.11-1.96 (m, 4H), 1.71 (d, J=7.2 Hz, 3H); MS m/z 184 (M−121); Anal. Calcd. For C$_{21}$H$_{25}$BrN$_2$Cl: C, 73.99; H, 7.39; N, 8.22. Found: C, 73.85; H, 7.38; N, 8.23.

Example 44

(1S)-6-Methyl-N-[(1R)-1-phenylethyl]-2,3,4,9-tetrahydro-1H-carbazol-1-amine hydrochloride salt

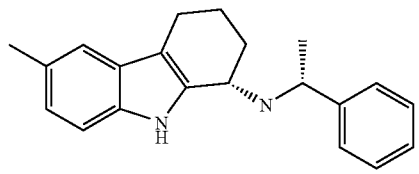

(1S)-6-Methyl-N-[(1R)-1-phenylethyl]-2,3,4,9-tetrahydro-1H-carbazol-1-amine hydrochloride salt was prepared by separation of diastereomeric 6-methyl-N-[(1R)-1-phenylethyl]-2,3,4,9-tetrahydro-1H-carbazol-1-amine by SFC (Berger Amino, 10% methanol, 1500 psi, 40° C., 2 mL/min, retention time: 10.0 min.) The oil obtained was converted to the HCl salt to give a white solid. [α]$^{25}$=−20.0 (c 0.20, MeOH); $^1$H-NMR (DMSO-d$_6$): δ 7.58 (d, J=7.6 Hz, 2H), 7.55-7.46 (m, 3H), 7.26 (d, J=8.0 Hz, 1H), 7.26 (m, 1H), 7.01 (d, J=8.8 Hz, 1H), 4.74 (q, J=7.2 Hz, 1H), 4.43 (t, J=4.8 Hz, 1H), 2.82 (dt, J=16.4 Hz, J=4.0 Hz, 1H), 2.68 (dt, J=16.4 Hz, J=4.8 Hz, 1H), 2.40 (s, 3H), 2.32-2.20 (m, 1H), 2.18-2.00 (m, 2H), 1.98-1.88 (m, 1H), 1.75 (d, J=6.8 Hz, 3H); MS m/z 184 (M−121); Anal. Calcd. For C$_{21}$H$_{25}$BrN$_2$Cl: C, 73.99; H, 7.39; N, 8.22. Found: C, 74.02; H, 7.30; N, 8.31.

Example 45

6-Methyl-N-[(1S)-1-phenylethyl]-2,3,4,9-tetrahydro-1H-carbazol-1-amine hydrochloride salt

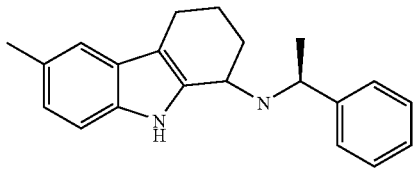

6-Methyl-N-[(1S)-1-phenylethyl]-2,3,4,9-tetrahydro-1H-carbazol-1-amine hydrochloride salt was prepared from 6-methyl-2,3,4,9-tetrahydro-1H-carbazol-1-one (0.1 g, 0.5 mmol) and S-α-methylbenzylamine in an identical manner as above. $^1$H-NMR (CDCl$_3$): δ 8.05 (s, 1H), 7.50-7.18 (m, 7H), 7.36 (d, J=8.1 Hz, 1H), 4.13 (q, J=5.77 Hz, 1H), 3.99 (t, J=6.3 Hz, 1H), 2.44 (s, 3H), 2.20-2.13 (m, 1H), 2.05-1.95 (m, 1H), 1.64-1.48 (m, 4H), 1.42 (d, J=6.3 Hz, 3H); MS m/z 184 (M−121).

Example 46

(1S)-6-Methyl-N-[(1S)-1-phenylethyl]-2,3,4,9-tetrahydro-1H-carbazol-1-amine hydrochloride salt

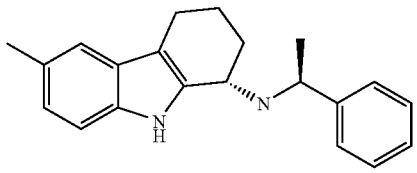

(1S)-6-Methyl-N-[(1S)-1-phenylethyl]-2,3,4,9-tetrahydro-1H-carbazol-1-amine hydrochloride salt was prepared by separation of diastereomeric 6-methyl-N-[(1S)-1-phenylethyl]-2,3,4,9-tetrahydro-1H-carbazol-1-amine by SFC (Berger Amino, 8% methanol, 1500 psi, 40° C., 2 mL/min, retention time: 8.7 min.) The oil obtained was converted to the HCl salt to give a white solid. [α]$^{25}$=−133.5 (c 0.20, MeOH); $^1$H-NMR (CD$_3$OD): δ 7.63 (d, J=7.6 Hz, 2H), 7.55-7.46 (m, 3H), 7.29 (d, J=8.0 Hz, 1H), 7.27 (s, 1H), 7.02 (d, J=8.4 Hz, 1H), 4.75 (q, J=7.2 Hz, 1H), 4.43 (m, 1H), 2.85 (dt, J=16.4 Hz, J=4.0 Hz, 1H), 2.67 (dt, J=16.4 Hz, J=4.0 Hz, 1H), 2.40 (s, 3H), 2.11-1.96 (m, 4H), 1.71 (d, J=7.2 Hz, 3H); MS m/z 184 (M−121).

Example 47

(1R)-6-Methyl-N-[(1S)-1-phenylethyl]-2,3,4,9-tetrahydro-1H-carbazol-1-amine hydrochloride salt

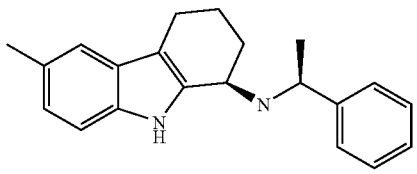

(1R)-6-Methyl-N-[(1S)-1-phenylethyl]-2,3,4,9-tetrahydro-1H-carbazol-1-amine hydrochloride salt was prepared by separation of diastereomeric 6-methyl-N-[(1S)-1-phenylethyl]-2,3,4,9-tetrahydro-1H-carbazol-1-amine by SFC (Berger Amino, 10% methanol, 1500 psi, 40° C., 2 mL/min, retention time: 10.0 min.) The oil obtained was converted to the HCl salt to give a white solid. [α]$^{25}$=22.5 (c 0.20, MeOH); $^1$H-NMR (DMSO-d$_6$): δ 7.58 (d, J=7.6 Hz, 2H), 7.55-7.46 (m, 3H), 7.26 (d, J=8.0 Hz, 1H), 7.26 (m, 1H), 7.01 (d, J=8.8 Hz, 1H), 4.74 (q, J=7.2 Hz, 1H), 4.43 (t, J=4.8 Hz, 1H), 2.82 (dt, J=16.4 Hz, J=4.0 Hz, 1H), 2.68 (dt, J=16.4 Hz, J=4.8 Hz, 1H), 2.40 (s, 3H), 2.32-2.20 (m, 1H), 2.18-2.00 (m, 2H), 1.98-1.88 (m, 1H), 1.75 (d, J=6.8 Hz, 3H); MS m/z 184 (M−121).

Example 48

N-Benzyl-6-nitro-2,3,4,9-tetrahydro-1H-carbazol-1-amine hydrochloride salt

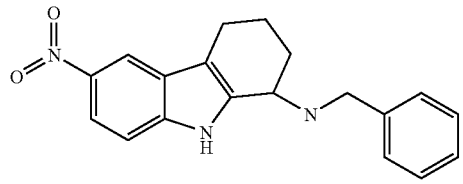

N-Benzyl-6-nitro-2,3,4,9-tetrahydro-1H-carbazol-1-amine hydrochloride salt was prepared from 6-nitro-2,3,4,9-tetrahydro-1H-carbazol-1-one (0.1 g, 0.22 mmol) (see, *J. Heterocyclic Chemistry*, 1990, 27(7), 1947-51, herein incorporated by reference with regard to the synthesis of this starting material) and benzyl amine (0.03 mL, 0.33 mmol), in a similar manner as described above to give a white solid (0.01 g, 8%). $^1$H-NMR (CD$_3$OD): δ 8.55 (s, 1H), 8.14 (d, 1H), 7.56-7.53 (m, 3H), 7.49-7.45 (m, 3H), 4.71 (t, 1H), 4.44 (m, 2H), 2.99 (dt, 1H), 2.83 (dt, 1H), 2.38-2.25 (m, 2H), 2.15-2.00 (m, 2H); MS m/z 320 (M−1).

Example 49

6-Nitro-N-[(1R)-1-phenylethyl]-2,3,4,9-tetrahydro-1H-carbazol-1-amine hydrochloride salt

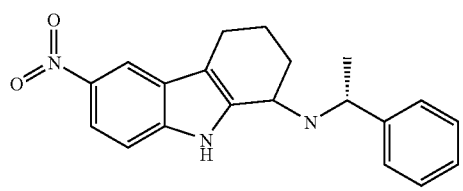

6-Nitro-N-[(1R)-1-phenylethyl]-2,3,4,9-tetrahydro-1H-carbazol-1-amine hydrochloride salt was prepared from 6-bromo-2,3,4,9-tetrahydro-1H-carbazol-1-one (0.05 g, 0.22 mmol) and (R)-α-methylbenzylamine (0.04 mL, 0.33 mmol), in a similar manner as described above to give a white solid (0.005 g, 6%). $^1$H-NMR (DMSO-d$_6$): δ 12.2 (s, 1H), 9.86 (s, 1H), 9.32 (s, 1H), 8.49 (s, 1H), 8.04 (d, 1H), 7.75 (d, 2H), 7.59 (d, 1H), 7.47-7.38 (m, 3H), 4.76 (q, 1H), 4.46 (t, J=4.2 Hz, 1H), 2.81-2.67 (m, 2H), 2.14-2.08 (m, 1H), 2.00-1.93 (m, 2H) 1.87-1.80 (m, 1H), 1.67 (d, 3H); MS m/z 334 (M−1).

Example 50

7-Bromo-N-(2-phenylethyl)-1,2,3,4-tetrahidrocyclopenta[b]indol-3-amine hydrochloride salt

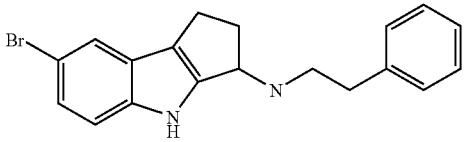

7-Bromo-1,4-dihydrocyclopenta[b]indol-3(2H)-one was prepared from bromoaniline and 2-(hydroxymethylene)cyclopentanone in a similar manner as described above to give 0.5 g of a brown solid. $^1$H-NMR (DMSO-$d_6$): δ 8.73 (s, 1H), 7.87 (s, 1H), 7.48 (d, 1H), 7.36 (d, 1H), 3.09 (dd, 2H), 3.02 (dd, 2H); MS m/z 249, 251 (M+1).

7-Bromo-N-(2-phenylethyl)-1,2,3,4-tetrahydrocyclopenta[b]indol-3-amine hydrochloride salt was prepared from 7-bromo-1,4-dihydrocyclopenta[b]indol-3(2H-one (0.1 g, 0.4 mmol) and phenethyl amine (0.075 mL, 0.6 mmol), in a similar manner as described above to give a white solid (0.005 g, 3%). $^1$H-NMR (DMSO-$d_6$): δ 11.2 (s, 1H), 9.28 (s, 2H), 7.67 (s, 1H), 7.40-7.22 (m, 7H), 7.36 (d, 3H), 4.80 (m, 1H), 3.30-3.23 (m, 2H), 3.09-3.06 (m, 1H), 3.02-2.85 (m, 2H), 2.75-2.70 (m, 1H); MS m/z 353, 355 (M−1).

Example 51

(3R)-7-Bromo-N-[(1R)-1-phenylethyl]-1,2,3,4-tetrahydrocyclooenta[b]indol-3-amine hydrochloride salt

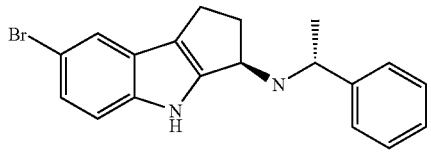

(3R)-7-Bromo-N-[(1R)-1-phenylethyl]-1,2,3,4-tetrahydrocyclopenta[b]indol-3-amine hydrochloride salt was prepared from 7-bromo-11,4-dihydrocyclopenta[b]indol-3(2H)-one (0.1 g, 0.4 mmol) and (R)-α-methylbenzylamine (0.075 mL, 0.6 mmol), in a similar manner as described above to give a white solid. Purification, by prep. TLC, afforded (0.004 g, 3%). $^1$H-NMR 80° C. (DMSO-$d_6$): δ 11.1 (s, 1H), 10.0 (s, 1H), 9.25 (s, 1H), 7.69-7.60 (m, 3H), 7.44-7.24 (m, 4H), 7.23 (d, 1H), 4.70 (s, 1H), 4.57 (s, 1H), 3.40 (m, 2H), 3.19 (m, 1H), 2.88-2.81 (m, 1H), 2.74-2.64 (m, 2H), 1.68 (d, 3H); MS m/z 353, 355 (M−1).

Example 52

(3S)-7-Bromo-N-[(1R)-1-phenylethyl]-1,2,3,4-tetrahydrocyclobenta[b]indol-3-amine hydrochloride salt

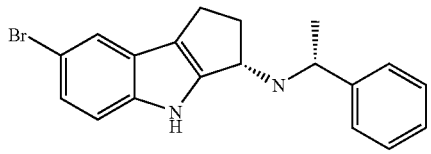

(3R)-7-Bromo-N-[(1R)-1-phenylethyl]-1,2,3,4-tetrahydrocyclopenta[b]indol-3-amine hydrochloride salt was prepared from 7-bromo-1,4-dihydrocyclopenta[b]indol-3(2H)-one (0.1 g, 0.4 mmol) and (R)-α-methylbenzylamine (0.075 mL, 0.6 mmol), in a similar manner as described above to give a white solid. Purification by preparative TLC gave the desired compound (0.001 g, 1%). $^1$H-NMR (DMSO-$d_6$): δ 11.4 (s, 1H), 9.67 (s, 1H), 9.60 (s, 1H), 8.13 (d, 1H), 7.74 (dd, 1H), 7.63 (dd, 1H), 7.43 (d, 1H), 7.39-7.34 (m, 1H), 7.31-7.2 (m, 3H), 4.96 (s, 1H), 4.85 (q, 1H), 3.76 (m, 1H), 3.58-3.50 (m, 2H), 3.30 (m, 1H), 3.23 (d, 3H); MS m/z 353, 355 (M−1).

Example 53

N-Benzyl-6-methoxy-2,3,4,9-tetrahydro-1H-carbazol-1-amine hydrochloride salt

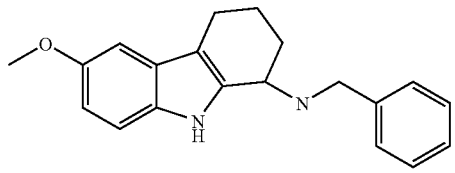

N-Benzyl-6-methoxy-2,3,4,9-tetrahydro-1H-carbazol-1-amine hydrochloride salt was prepared from 6-methoxy-2,3,4,9-tetrahydro-1H-carbazol-1-amine (0.05 g, 0.23 mmol), benzaldehyde (0.04 mL, 0.35 mmol) in THF in a similar manner as described above to give a white solid (0.02 g, 25%). $^1$H-NMR (DMSO-$d_6$): δ 11.1 (s, 1H), 9.68 (s, 1H), 9.54 (s, 1H), 7.63 (d, 2H), 7.44-7.39 (m, 3H), 7.28 (d, 1H), 6.95 (s, 1H), 6.78 (d, 1H), 4.62 (t, 1H), 4.26 (m, 2H), 3.74 (s, 3H), 2.71-2.60 (m, 2H), 2.21-2.17 (m, 2H), 2.10-2.04 (m, 1H), 1.81-1.75 (m, 1H); MS m/z 305 (M−1).

Example 54

N-Benzyl-2-bromo-5,6,7,8,9,10-hexahydrocyclohepta[b]indol-6-amine hydrochloride

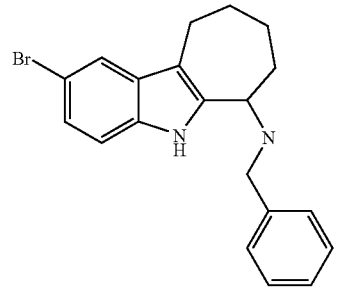

A solution of 2-bromo-5a,6,7,8,9,10,10a-hexahydrocyclohepta[b]indol-6-amine (50 mg, 0.16 mmol), benzyl bromide (54 mg, 0.32 mmol) and N,N-diisopropylethylamine (21 mg, 0.48 mmol) was stirred for 16 h at room temperature. The reaction mixture was diluted with ethyl acetate, washed with water (50 mL), separated and concentrated to a brown oil. The crude oil was purified by flash chromatography on silica (5% to 20% ethyl acetate/hexanes gradient) to provide the pure amine. The amine was diluted with diethyl ether and HCl (1.0 M in diethyl ether) was added. The solution was concentrated, dissolved in acetonitrile and water and lyophilized to give 25 mg (38%). of a light brown solid. $^1$H-NMR (DMSO-d$_6$): δ11.53 (s, 1H), 9.49 (d, 2H), 7.76 (s, 1H), 7.64-7.61 (d, 2H), 7.45-7.43 (m, 3H), 7.38 (d, 1H), 7.26-7.25 (m 1H), 4.68-4.61 (m, 1H), 4.37-4.29 (m, 1H), 4.02-3.93 (m, 1H), 3.02-2.98 (m, 2H), 2.22-1.89 (m, 4H), 1.51-1.26 (m, 2H); MS m/z (M−1) 367, 369.

Example 55

2-Bromo-N-[(1R)-1-phenylethyl]-5,6,7,8,9,10-hexahydrocycloheota[b]indol-6-amine hydrochloride

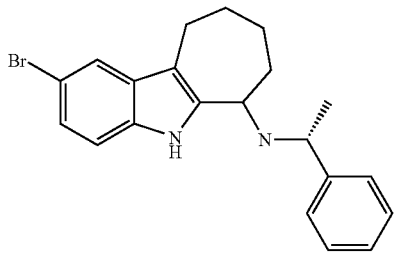

2-Bromo-N-[(1R)-1-phenylethyl]-5,6,7,8,9,10-hexahydrocyclohepta[b]indol-6-amine hydrochloride was prepared from 2-bromo-5a,7,8,9,10,10a-hexahydrocyclohepta[b]indol-6(5H)-one (150 mg, 0.54 mmol) and (R)-α-methylbenzylamine (98 mg, 0.81 mmol) in a similar manner as described above to give 2.5 mg (1%). of a white solid; MS m/z (M−1) 381, 383.

Example 56

2-Bromo-N-(2-phenylethyl)-5,6,7,8,9,10-hexahydrocycloheDta[b]indol-6-amine hydrochloride

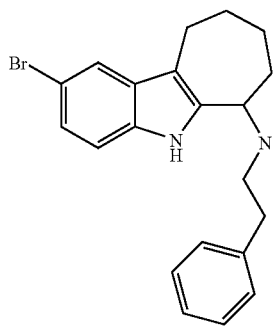

2-Bromo-N-(2-phenylethyl)-5,6,7,8,9,10-hexahydrocyclohepta[b]indol-6-amine hydrochloride was prepared from 2-bromo-5a,7,8,9,10,10a-hexahydrocyclohepta[b]indol-6 (5H)-one (150 mg, 0.54 mmol) and phenethylamine (65 mg, 0.54 mmol) in a similar manner as described above to give 81 mg (36%). of a white solid; $^1$H-NMR (DMSO-d$_6$): δ 11.45 (s, 1H), 9.47 (d, 1H), 9.10 (d, 1H), 7.71 (s, 1H), 7.31-7.28 (m, 3H), 7.20-7.18 (m, 4H), 4.57-4.56 (m, 1H), 3.39-3.05 (m, 2H), 2.97-2.83 (m, 4H), 2.45-2.42 (m, 1H), 2.16-1.85 (m, 4H), 1.45-1.35 (m, 1H); MS m/z 278, 280 (M−1) 381, 383.

Example 57

6-Bromo-N-(4-fluorobenzyl)-2,3,4,9-tetrahydro-1H-carbazol-1-amine hydrochloride

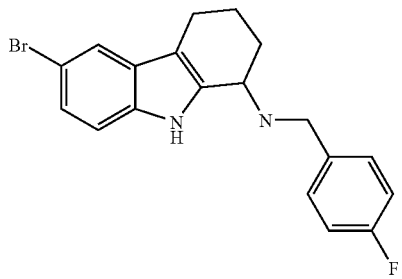

6-Bromo-N-(4-fluorobenzyl)-2,3,4,9-tetrahydro-1H-carbazol-1-amine hydrochloride was prepared from 6-bromo-2,3,4,9-tetrahydro-1H-carbazol-1-one (100 mg, 0.38 mmol) and 4-fluorobenzylamine (70 mg, 0.57 mmol) in a similar manner as described above to give 30 mg (19%). of a white solid; $^1$H-NMR (DMSO-d$_6$): δ 11.60 (s, 1H), 9.82-9.65 (m, 2H), 7.77-7.72 (m, 3H), 7.41 (d, 1H), 7.34-7.27 (m, 3H), 4.72-4.69 (m, 1H), 4.39-4.26 (m, 2H), 2.77-2.70 (m, 2H), 2.27-2.22 (m, 2H), 2.16-2.05 (m, 1H), 1.87-1.76 (m, 1H); MS m/z (M−1) 371, 373.

Example 58

N-Benzyl-6-(trifluoromethyl)-2,3,4,9-tetrahydro-1H-carbazol-1-amine hydrochloride

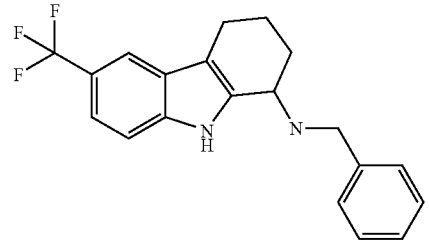

N-Benzyl-6-(trifluoromethyl)-2,3,4,9-tetrahydro-1H-carbazol-1-amine hydrochloride was prepared from 6-(trifluoromethyl)-2,3,4,9-tetrahydro-1H-carbazol-1-one (150 mg, 0.59 mmol) and benzylamine (130 mg, 1.2 mmol) in a similar manner as described above to give 52 mg (23%). of a white solid; $^1$H-NMR (DMSO-d$_6$): δ 12.07 (s, 1H), 10.13-9.95 (m, 2H), 7.87 (s, 1H), 7.68 (d, 2H), 7.57 (d, 1H), 7.42-7.39 (m, 4H), 4.72-4.68 (m, 1H), 4.29-4.25 (m, 2H), 2.74-2.71 (m, 2H), 2.31-2.23 (m, 2H), 2.13-2.08 (m, 1H), 1.81-1.74 (m, 1H).

Example 59

N-[(1R)-1-Phenylethyl]-6-(trifluoromethyl)-2,3,4,9-tetrahydro-1H-carbazol-1-amine hydrochloride

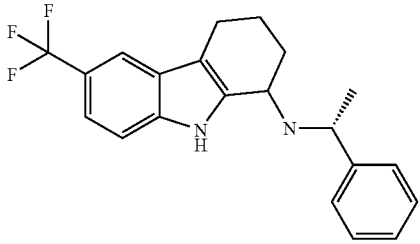

N-[(1R)-1-Phenylethyl]-6-(trifluoromethyl)-2,3,4,9-tetrahydro-1H-carbazol-1-amine hydrochloride was prepared from 6-(trifluoromethyl)-2,3,4,9-tetrahydro-1H-carbazol-1-one (150 mg, 059 mmol) and (R)-α-methylbenzylamine (150 mg, 1.2 mmol) in a similar manner as described above to give 11 mg (5%) of a white solid; $^1$H-NMR (DMSO-d$_6$): δ 12.00 (s, 1H), 9.98-9.74 (m, 2H), 7.97-7.90 (m, 1H), 7.79 (d, 1H), 7.61-7.57 (m, 1H), 7.54-7.38 (m, 5H), 4.77-4.62 (m, 1H), 4.17-4.00 (m, 1H), 2.73-2.70 (m, 1H), 1.60-1.58 (m, 1H), 1.65-1.54 (m, 2H), 1.29-1.27 (m, 1H), 1.23-1.07 (m, 4H); MS m/z (M−1)357.

Example 60

N-Benzhydryl-6-bromo-2,3,4,9-tetrahydro-1H-carbazol-1-amine hydrochloride

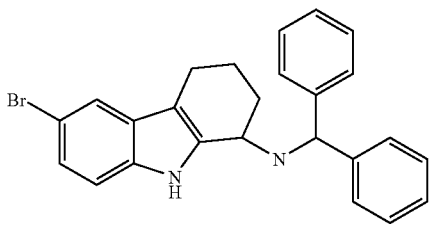

N-Benzhydryl-6-bromo-2,3,4,9-tetrahydro-1H-carbazol-1-amine hydrochloride was prepared from 6-bromo-2,3,4,9-tetrahydro-1H-carbazol-1-one (100 mg, 0.38 mmol)- and benzhydrylamine (70 mg, 0.38 mmol) in a similar manner as described above to give 40 mg (22%) of a white solid; $^1$H-NMR (DMSO-d$_6$): δ 11.97 (s, 1H), 10.51-10.46 (m, 1H), 10.14-10.11 (m, 1H), 7.97 (d, 2H), 7.86 (d, 2H), 7.65 (s, 1H), 7.48-7.31 (m, 7H), 7.24 (d, 1H), 5.97-5.94 (m, 1H), 4.42-4.38 (m, 1H), 2.63-2.61 (m, 2H), 2.17-1.97 (m, 3H), 1.75-1.66 (m, 1H); MS m/z (M−1)429, 431.

Example 61

N-Benzyl-7-bromo-2,3,4,9-tetrahydro-1H-carbazol-1-amine hydrochloride

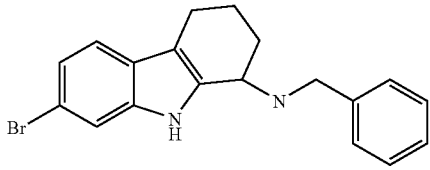

N-Benzyl-7-bromo-2,3,4,9-tetrahydro-1H-carbazol-1-amine hydrochloride was prepared from 7-bromo-2,3,4,9-tetrahydro-1H-carbazol-1-one (45 mg, 0.17 mmol) and ben- zylamine (18 mg, 0.17 mmol) in a similar manner as described above to give 35 mg (52%). of a white-solid; $^1$H-NMR (DMSO-d$_6$): δ 11.48 (s, 1H), 9.76-9.65 (m, 2H), 7.64-7.61 (m, 1H), 7.55-7.52 (m, 1H), 7.46-7.39 (m, 5H), 7.16-7.14 (m, 1H), 4.67-4.64 (m, 1H), 4.32-4.25 (m, 2H), 2.74-2.60 (m, 2H), 2.21-2.19 (m, 2H), 2.10-2.04 (m, 1H), 1.81-1.75 (m, 1H).

Example 62

7-Bromo-N-[(1R)-1-phenylethyl]-2,3,4,9-tetrahydro-1H-carbazol-1-amine hydrochloride

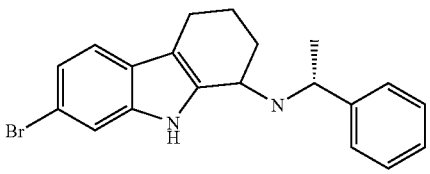

7-Bromo-N-[(1R)-1-phenylethyl]-2,3,4,9-tetrahydro-1H-carbazol-1-amine hydrochloride was prepared from 7-bromo-2,3,4,9-tetrahydro-1H-carbazol-1-one (45 mg, 0.17 mmol) and (R)-α-methylbenzylamine (21 mg, 0.17 mmol) in a similar manner as described above to give 37 mg (54%). of a white solid, $^1$H-NMR (DMSO-d$_6$): δ 11.56 (s, 1H), 9.80-9.75 (m, 1H), 9.31-9.21 (m, 1H), 7.75 (d, 2H), 7.60 (s, 1H), 7.47-7.38 (m, 4H), 7.14 (d, 1H), 4.76-4.70 (m, 1H), 4.55-4.51 (m, 1H), 2.69-2.57 (m, 2H), 2.10-1.72 (m, 4H), 1.66 (d, 3H).

Example 63

7-Bromo-N-(2.3-dihydro-1H-inden-2-yl)-2,3,4,9-tetrahydro-1H-carbazol-1-amine hydrochloride

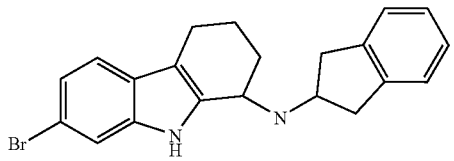

7-Bromo-N-(2,3-dihydro-1H-inden-2-yl)-2,3,4,9-tetrahydro-1H-carbazol-1-amine hydrochloride was prepared from 7-bromo-2,3,4,9-tetrahydro-1H-carbazol-1-one (45 mg, 0.17 mmol) and 2-aminoindane (23 mg, 0.17 mmol) in a similar manner as described above to give 23 mg (32%). of a white solid; $^1$H-NMR (DMSO-d$_6$): δ 11.38 (s, 1H), 9.74-9.60 (m, 2H), 7.58 (s, 1H), 7.46 (d, 1H), 7.45-7.15 (m, 5H), 4.67-4.66 (m, 1H), 4.35-4.31 (m, 1H), 3.49-3.25 (m, 4H); 2.76-2.62 (m, 2H), 2.22-2.00 (m, 3H), 1.86-1.82 (m, 1H); MS m/z (M−1) 379, 381.

Example 64

6-Bromo-1-[(phenylmethyl)oxy]-2,3,4,9-tetrahydro-1H-carbazole

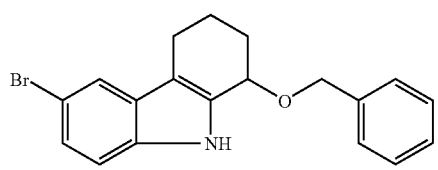

6-Bromo-9-(phenylsulfonyl)-2,3,4,9-tetrahydro-1H-carbozol-1-one. To a solution of 6-bromo-2,3,4,9-tetrahydro-1H-carbazol-1-one (300 mg, 1.1 mmol) in methylene chloride (10 mL) was added benzene sulfonylchloride (201 mg, 1.1 mmol), aqueous sodium hydroxide (5N, 1.1 mL, 5.5 mmol) and benzyltriethylammonium chloride (catalytic). The reaction mixture was stirred overnight at room temperature. Additional benzene sulfonylchloride (201 mg, 1.1 mmol) and sodium hydroxide (300 mg, 7.5 mmol) and the reaction was stiired for 1 hour. The reaction was washed with water, dried over sodium sulfate, filtered and concentrated. The crude ketone was purified by flash chromatography on silica (5% to 30% gradient of ethyl acetate/hexanes) to provide 6-bromo-9-(phenylsulfonyl)-2,3,4,9-tetrahydro-1H-carbozol-1-one (400 mg, 87%). as a light brown solid: $^1$H-NMR (DMSO-d$_6$): δ 8.26 (d, 1H), 8.12 (d, 2H), 7.76 (s, 1H), 7.63-7.58 (m, 2H), 7.52 (t, 2H), 2.91-2.89 (m, 2H), 2.62-2.59 (m, 2H), 2.20-2.14 (m, 2H).

6-Bromo-9-(phenylsulfonyl)-2,3,4,9-tetrahydro-1H-carbazol-1-ol. To a solution of 6-bromo-9-(phenylsulfonyl-2,3,4,9-tetrahydro-1H-carbazol-1-one (150 mg, 0.37 mmol) in methanol (10 mL) was added sodium borohydride (30 mg, 0.79 mmol). The reaction was stirred for 30 min at room temperature and quenched with water (10 mL). The resulting precipitate was collected by vacuum filtration and dried to provide 6-Bromo-9-(phenylsulfonyl)-2,3,4,9-tetrahydro-1H-carbazol-1-ol (135 mg, 89%). as a yellow solid: $^1$H-NMR (DMSO-d$_6$): δ 8.10-8.07 (m, 2H), 7.94 (d, 1H), 7.70-7.64 (m, 2H), 7.55 (t, 2H), 7.48-7.46 (m, 1H), 5.31 (d, 1H), 5.28-5.28 (m, 1H), 2.75-2.68 (m, 2H), 1.99-1.89 (m, 2H), 1.81-1.70 (m, 2H); MS m/z (M+1) 404, 406.

6-Bromo-1-[(phenylmethyl)oxy]-2,3,4,9-tetrahydro-1H-carbazole. To a solution of 6-bromo-9-(phenylsulfonyl)-2,3,4,9-tetrahydro-1H-carbazol-1-ol (25 mg, 0.06 mmol) in N,N-dimethylformamide (2 mL) was added benzyl bromide (0.5 mL) and sodium hydride (60% in oil, 50 mg, 1.2 mmol). The reaction was stirred 1.0 min and quenched with water (1 mL). The reaction was diluted with ethyl acetate, washed with water, and concentrated to provide 6-bromo-1-[(phenylmethyl)oxy]-9-(phenylsulfonyl)-2,3,4,9-tetrahydro-1H-carbolzole: MS m/z (m−1) 494, 496. The crude benzyl ether was dissolved in methanol (5 mL) and tetrahydrofuran (3 mL) and aqueous sodium hydroxide (5N, 2 mL) and sodium hydroxide pellets (300 mg, 1.1 mmol) were added. The reaction was stirred at 70° C. for 16 h. The reaction was concentrated, diluted with ethyl acetate, washed with water and concentrated. The crude ether was purified by flash chromatography on silica (5% to 10% ethyl acetate/hexanes) to provide 6-bromo-1-[(phenylmethyl)oxy]-2,3,4,9-tetrahydro-1H-carbazole (15 mg, 71%). as an oily white solid: $^1$H-NMR (DMSO-d$_6$): δ 11.10 (s, 1H), 7.57 (s, 1H), 7.39 (d, 2H), 7.33 (t, 2H), 7.29-7.24 (d, 2H), 7.13 (d, 1H), 4.72-4.61 (m, 3H), 2.69-2.63 (m, 1H), 2.55-2.50 (m, 1H), 1.99-1.91 (m, 3H), 1.78-1.71 (m, 1H); MS m/z (M−1) 354, 356.

Example 65

N-(6-Bromo-2,3,4,9-tetrahydro-1H-carbazol-1-yl)-N'-isopropylurea

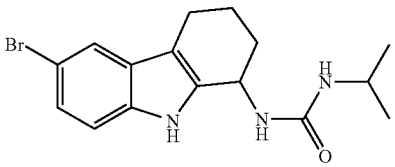

N-(6-Bromo-2,3,4,9-tetrahydro-1H-carbazol-1-yl)-N-isopropylurea was prepared from 6-bromo-2,3,4,9-tetrahydro-1H-carbazol-1-amine and isopropyl isocyanate to give a tan solid (58% yield). $^1$H-NMR (DMSO-d$_6$): δ 10.89 (s, 1H), 7.57 (d, 1H), 7.29 (d, 1H), 7.16 (dd, 1H), 6.18 (d, 1H), 5.63 (d, 1H), 4.90 (m, 1H), 3.78 (m, 1H), 2.64 (m, 2H), 1.97 (m, 1H), 1.90-1.67 (m, 3H), 1.08, (d, 6H); MS m/z 350 (M−1).

Example 66

Methyl 6-bromo-2,3,4,9-tetrahydro-1H-carbazol-1-ylcarbamate

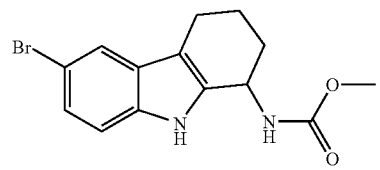

Methyl 6-bromo-2,3,4,9-tetrahydro-1H-carbazol-1-ylcarbamate was prepared from 6-bromo-2,3,4,9-tetrahydro-1H-carbazol-1-amine and methyl chloroformate to give a yellow oil (8% yield). $^1$H-NMR (CDCl$_3$): δ 8.70 (s, 1H), 7.60 (m, 1H), 7.28-7.16 (m, 2H), 4.98 (m, 1H), 4.90 (m, 1H), 3.74 (s, 3H), 2.66 (m, 2H), 2.21 (m, 1H), 1.90 (m, 2H), 1.81 (m, 1H); MS m/z 324 (M+1).

Example 67

N-(6-Bromo-2,3,4,9-tetrahydro-1H-carbazol-1-yl)acetamide

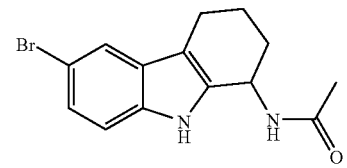

N-(6-Bromo-2,3,4,9-tetrahydro-1H-carbazol-1-yl)acetamide was prepared from 6-bromo-2,3,4,9-tetrahydro-1H-carbazol-1-amine and acetyl chloride in the presence of diisopropylethylamine to give a tan solid (52% yield). $^1$H-NMR (CDCl$_3$): δ 8.86 (s, 1H), 7.59 (m, 1H), 7.22 (m, 1H), 7.16 (d, 1H), 5.80 (m, 1H), 5.10 (m, 1H), 2.67 (m, 2H), 2.22 (m, 1H), 2.04 (s, 3H), 1.91 (m, 2H), 1.81 (m, 1H); MS m/z 306 (M−1).

Example 68

N-(6-Bromo-2,3,4,9-tetrahydro-1H-carbazol-1-yl)cyclohexanecarboxamide

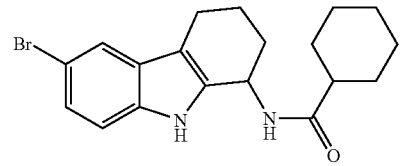

N-(6-Bromo-2,3,4,9-tetrahydro-1H-carbazol-1-yl)cyclohexanecarboxamide was prepared from 6-bromo-2,3,4,9-tetrahydro-1H-carbazol-1-amine and cyclohexane carbonyl chloride to give a tan solid (62% yield). $^1$H-NMR (CDCl$_3$): δ 8.86 (s, 1H), 7.58 (m, 1H), 7.21 (dd, 1H), 7.16 (d, 1H), 5.74 (m, 1H), 5.07 (m, 1H), 2.66 (m, 2H), 2.26-2.05 (m, 2H), 1.96-1.72 (m, 7H), 1.70-1.63 (m, 1H), 1.52-1.35 (m, 2H), 1.31-1.16 (m, 3H); MS m/z 375 (M−1):

Example 69

N-(6-Bromo-2,3,4,9-tetrahydro-1H-carbazol-1-yl)methanesulfonamide

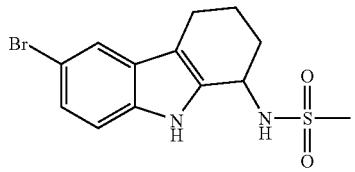

N-(6-Bromo-2,3,4,9-tetrahydro-1H-carbazol-1-yl)methanesulfonamide was prepared from 6-bromo-2,3,4,9-tetrahydro-1H-carbazol-1-amine and methane sulfonyl chloride to give a tan solid (57% yield). $^1$H-NMR (CDCl$_3$): δ 8.71 (s, 1H), 7.60 (m, 1H), 7.26 (m, 1H), 7.20 (d, 1H), 4.71A4.59 (m, 2H), 3.07 (s, 3H), 2.67 (m, 2H), 2.22 (m, 1H), 2.00-1.78 (m, 3H); MS m/z 343 (M−1).

Example 70

N-(6-Bromo-2,3,4,9-tetrahydro-1H-carbazol-1-yl) urea

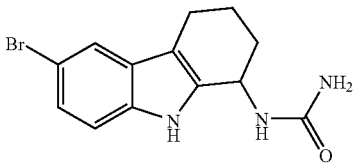

To a solution of 6-bromo-2,3,4,9-tetrahydro-1H-carbazol-1-amine (50 mg, 0.19 mmol) in isopropanol (0.30 mL) was added trimethylsilyl isocyanate. The mixture was stirred at room temperature 15 hours, the solvent removed, and the residue purified by flash chromatography (0-5% methanol-dichloromethane) to give 23 mg (40% yield) of a brown solid. $^1$H-NMR (DMSO-d$_6$): δ 10.91 (s, 1H), 7.57 (d, 1H), 7.30 (d, 1H), 7.16 (dd, 1H), 6.46 (d 1H), 4.87 (m, 1H), 2.64 (m, 2H), 1.97 (m, 1H), 1.90-1.65 (m, 3H); MS m/z 308 (M−1).

Example 71

N-Benzyl-8-bromo-2,3,4,9-tetrahydro-1H-carbazol-1-amine hydrochloride

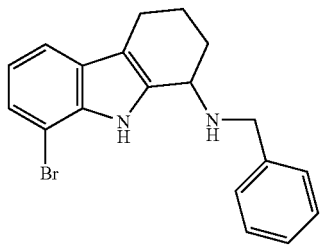

To a solution of 2-bromoaniline (2.0 g, 12 mmol) in N,N-dimethylformamide (15 mL) was added potassium carbonate (2.4 g, 18 mmol) and 3-bromocyclohexene (2.7 mL, 23 mmol). The mixture was heated at 75° C. for 16 hours. The reaction was allowed to cool before being diluted with ethyl acetate (50 mL) and toluene (15 mL). The solution was washed with brine, dried over magnesium sulfate, and concentrated. The residue was dried under high vacuum to yield 2.13 g (73%) of N-(2-bromophenyl)-N-cyclohex-2-en-1-ylamine. $^1$H NMR (DMSO-d$_6$): δ 7.40 (d, 1H), 7.16 (t, 1H), 6.79 (d, 1H), 6.53 (t, 1H), 5.83-5.88 (m, 1H), 5.66-5.71 (m, 1H); 4.43 (d, 1H), 4.06 (m, 1H), 1.99 (m, 2H), 1.82 (m, 1H), 1.60 (m, 3H). MS m/z 252, 254 (M+1).

A mixture of of N-(2-bromophenyl)-N-cyclohex-2-en-1-ylamine (2.13 g; 8.4 mmol) and zinc chloride (1.26 g, 9.3 mmol) were refluxed in xylenes' (30 mL) for 6 hours and then allowed to cool to room, temperature. The reaction was stirred at room temperature for 16 hours. The crude reaction mixture was poured directly onto a silica gel chromatography column and was eluted with a gradient of 3% to 5% to 10% ethyl ether in hexanes. Appropriate fractions were concentrated to leave a 1.0 g, 1:1 mixture of 2-bromo-6-cyclohex-2-en-1-ylaniline and by-product that was not separable by normal phase chromatography. A small amount (30 mg) of the mixture was purified by reverse phase chromatography to obtain an analytically pure sample, while the remainder of the material was carried forward as a mixture. $^1$H NMR (DMSO-d$_6$): δ7.22 (d, 1H), 7.32 (d, 1H), 6.47 (t, 1H), 5.90 (m, 1H), 5.58 (d, 1H), 5.05 (s, 2H), 3.55 (m, 1H), 2.01 (m, 2H), 1.91 (m, 1H), 1.54 (m, 2H), 1.37 (m, 1H). MS m/z 252, 254 (M+1).

To the 2-bromo-6-cyclohex-2-en-1-ylaniline mixture (0.85 g, 3.4 mmol) above in dichloromethane (50 mL) was added sodium bicarbonate (2.3 g, 27 mmol) followed by iodine (3.5 g, 14 mmol). The reaction was stirred for 3 hours and then diluted with dichloromethane (100 mL). The organic phase was washed with a 10% w/w aqueous solution of sodium thiosulfate, washed with brine, and was dried by passing through a hydrophobic frit. The organic solution was concentrated to leave crude 8-bromo-1-iodo-2,3,4,4a,9,9a-hexahydro-1H-carbazole. MS m/z 378, 380 (M+1).

8-bromo-1-iodo-2,3,4,4a,9,9a-hexahydro-1H-carbazole (0.63 g) from above, sodium bicarbonate (300 mg), and benzylamine (2.5 mL) were heated at 150° C. in a SmithCreator microwave for 600 seconds. The mix was allowed to cool and then diluted with dichloromethane. The organic phase was washed with water and concentrated. The residue was purified by silica gel chromatography eluting with ethyl acetate. Concentration of appropriate fractions yielded a 320 mg of a 1:1 mixture of 1-benzyl-8-methyl-2,3,4,4a,9,9a-hexahydro-1H-carbazole and a by-product that was not separable by normal phase chromatography. A small amount (25 mg) of the mixture was purified by reverse phase chromatography to obtain an analytically pure sample, while the remainder of the material was carried forward as a mixture. $^1$H NMR (DMSO-d$_6$): δ 7.30-7.38 (m, 4H), 7.26 (s, 2H), 7.14 (d, 1H), 6.92 (d, 1H), 6.59 (t, 1H), 4.00 (d, 1H), 3.71 (d, 1H), 3.50 (m, 1H), 3.42 (t, 1H), 2.33 (m, 1H), 2.15 (m, 1H), 2.03 (m, 1H), 1.61-1.82 (m, 2H), 1.15-1.27 (m, 1H), 1.03-1.14 (m, 1H); MS m/z 357, 359 (M+1).

To a solution of 1-benzyl-8-methyl-2,3,4,4a,9,9a-hexahydro-1H-carbazole (220 mg, 0.62 mmol) in dichloromethane (8 mL) was added 2,3-dichloro-5,6-dicyano-1,4-benzoquinone (210 mg, 0.93 mmol) and the mixture stirred at room temperature for 16 hours. The solution was diluted with dichloromethane (30 mL) and was washed with 1 M sodium hydroxide (2×25 mL). The organic phase was passed through a hydrophobic frit and concentrated to leave 200 mg of crude material. 100 mg of the crude material was purified by reverse phase chromatography. Appropriate fractions were concentrated to leave an oil. The oil was dissolved in ethyl ether and subject to dropwise addition of 2.5M HCl in ether. The resulting white precipitate was collected by filtration and dried under high vacuum to leave 16 mg of N-benzyl-8-bromo-2,3,4,9-tetrahydro-1H-carbazol-1-amine hydrochloride. $^1$H NMR (DMSO-$d_6$): δ 11.20 (s, 1H), 9.20 (bs, 2H), 7.63 (d, 2H), 7.53 (d 1H), 7.46 (m, 3H), 7.38 (d, 1H), 7.00 (t, 1H), 4.75 (m, 1H), 4.23-4.38 (m, 2H), 2.71 (t, 2H), 2.25-2.34 (m, 1H), 2.07-2.22 (m, 2H), 1.76-1.86 (m, 1H); MS m/z 248, 250 (M-benzylamine).

Biological Experimentals and Data

Compounds of the current invention are believed useful in the treatment and/or prophylaxis of conditions and diseases associated with HPV infection. Activity mediated through HPV was determined using the following W-12 cellular assay.

Cell Culture and Medium

The W12 cell line used contains HPV16 DNA and was derived from a low-grade cervical dysplasia tissue by Margaret Stanley and subsequently clonally selected by Paul Lambert (University of Wisconsin). One of these clones, W12-20850, contains 1000 copies of episomal HPV16 DNA and was used in the cell-based assay. W12-20850 cells were routinely cultured with a gamma-irradiated (6000 rads) feeder layer of 3T3 cells. Assays, however, were run in the absence of a 3T3 feeder layer. W12-20850 and 3T3 cells were routinely split when they were sub-confluent. W12-20850 were grown in W12 Medium which is constituted of 25% DMEM (Gibco BRL, Cat # 12430-047), 75% F12 Media (Gibco BRL, Cat # 11765-021) and 2.5% FBS. The additives include 24.0 mg/ml Adenine (Sigma, Cat # A-9795), 0.4 mg/ml Hydrocortisone (Calbiochem, Cat # 386698); 5.0 mg/ml Bovine Insulin (Sigma, Cat # I-1882), 8.4 ng/ml cholera toxin (Fluka, Cat # 26694) and 10 ng/ml EGF (Invitrogen, Cat # 13247-051). 3T3 cells were grown in DMEM containing 10% FBS. Cell lines were incubated at 37° C., in the presence of 5% $CO_2$.

Cell Based Assay

For the assay, W12-20850 cells were seeded into a 96 well plate-containing compound. Plates were incubated at 37° C. in the presence of 5% $CO_2$, for four days. On the fourth day, cells were lysed and the amount of episomal. HPV-16 DNA was quantified using a non-radioactive hybrid capture technique with HPV-16 specific capture and detection probes. The percent inhibition relative to untreated control cells' was then determined.

Hybrid Capture

The hybrid capture assay is run in a 96 well plate format. Hybridization plates (Nunc Maxisorb Cat # 450320) were coated with a mixture of capture probe and ReactiBind solution for at least 4 hours and then washed with 0.2×SSC, 0.05% Tween20 (SSCT) prior to blocking with 150 ml/well of 0.2 N NaOH, 1% Igepal, 10 mg/ml hsDNA for 6-8 hours. The hybridization was carried out by mixing 27 μl of lysed cells with 45 μl of denatured detection probe in 6M guanidine isothiocyanate. To prevent evaporation, 50 μl of mineral oil was added to each well. The plate was then heated to 90° C. for 6.5 minutes and the hybridization continued at 42° C. overnight. Assay plates were washed 6 times with SSC/T. Anti-digoxigenin HRP-conjugated Ab (Boehringer Mannheim 1207733, 1:5000) was incubated in the wells for 30 min at room temperature and washed with PBS/0.05% Tween-20. SuperSignal LBA substrate (Pierce Cat # 37070) was added, and chemiluminescence was measured using Wallac 1420 Victor plate reader.

| Example | W-12 |
|---|---|
| 15 | 6.6 uM |
| 16 | 1.5 uM |
| 17 | 7.4 uM |
| 18 | 12.3 uM |
| 19 | 14.5 uM |
| 20 | 3.3 uM |
| 21 | 40 uM |
| 22 | 47 uM |
| 23 | 30 uM |
| 24 | 5.3 uM |
| 25 | 1.5 uM |
| 26 | 410 nM |
| 27 | 57 nM |
| 28 | 3.7 uM |
| 29 | 115 nM |
| 30 | <200 nM |
| 31 | 30 nM |
| 32 | 525 nM |
| 33 | 750 nM |
| 34 | 290 nM |
| 35 | 3 uM |
| 36 | 20 nM |
| 37 | 3 uM |
| 38 | 27 uM |
| 39 | 160 nM |
| 40 | 2.7 uM |
| 41 | 400 nM |
| 42 | 540 nM |
| 43 | 240 nM |
| 44 | 8.4 uM |
| 45 | 7 uM |
| 46 | 8.6 uM |
| 47 | 160 nM |
| 48 | |
| 49 | 83 nM |
| 50 | 11 uM |
| 51 | 122 nM |
| 52 | 29 uM |
| 53 | 7.6 uM |
| 54 | 1.1 uM |
| 55 | 1 uM |
| 56 | 774 nM |
| 57 | 139 nM |
| 58 | 1 uM |
| 59 | 287 nM |
| 60 | 14 nM |
| 61 | 11 uM |
| 62 | 8 uM |
| 63 | 3.9 uM |
| 64 | 95 nM |
| 65 | 5 uM |
| 66 | 165 nM |
| 67 | 13 uM |
| 68 | 380 nM |
| 69 | 2.3 uM |
| 70 | 10.3 uM |
| 71 | 11.4 uM |

Test compounds were employed in free or salt form.

All research complied with the principles of laboratory animal care (NIH publication No. 85-23, revised 1985) and GlaxoSmithKline policy on animal use.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

What is claimed is:

1. A method for the treatment of HPV infection, genital warts, or cervical dysplasia comprising the administration of a compound of formula (I):

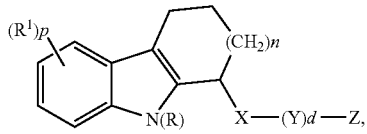

wherein:
n is 0, 1, or 2;
R is hydrogen or alkyl;
X is $NR^2$, O;
each $R^1$ is the same or different and is independently selected from the group consisting of hydrogen, halogen, haloalkyl, alkyl, alkenyl, alkynyl, cycloalkyl, cycloalkenyl, —$R^{10}$cycloalkyl, Ay, —$NHR^{10}$Ay, Het, —NHHet, —$NHR^{10}$Het, —$OR^2$, —OAy, —OHet, —$R^{10}OR^2$, —$NR^2R^3$, —$NR^2$Ay, —$R^{10}NR^2R^3$, —$R^{10}NR^2$Ay, —$R^{10}C(O)R^2$, —$C(O)R^2$, —$CO_2R^2$, —$R^{10}CO_2R^2$, —$C(O)NR^2R^3$, —C(O)Ay, —C(O)NR$^2$Ay, —C(O)Het, —$C(O)NHR^{10}$Het, —$R^{10}C(O)NR^2R^3$, —$C(S)NR^2R^3$, —$R^{10}C(S)NR^2R^3$, —$R^{10}NHC(NH)NR^2R^3$, —$C(NH)NR^2R^3$, —$R^{10}C(NH)NR^2R^3$, —$S(O)_2NR^2R^3$, —$S(O)_2NR^2$ Ay, —$R^{10}SO_2NHCOR^2$, —$R^{10}SO_2NR^2R^3$, —$R^{10}SO_2R^2$, —$S(O)_mR^2$, cyano, nitro, or azido;
Y is optionally substituted alkylene, optionally substituted cycloalkylene, optionally substituted alkenylene, optionally substituted cycloalkenylene, or optionally substituted alkynylene;
d is 0 or 1;
Z is —$R^2$, —$OR^2$, —$C(O)R^2$, —$C(O)_2R^2$, —$S(O)_mR^2$, —$C(O)NR^2R^3$, -Het, or -Ay, provided when d is 0, then Z is not -Het or -Ay;
each m independently is 0, 1 or 2;
each $R^{10}$ is the same or different and is independently selected from alkylene, cycloalkylene, alkenylene, cycloalkenylene, and alkynylene;
p is selected from 0, 1, 2, 3, or 4;
each of $R^2$ and $R^3$ are the same or different and are independently selected from the group consisting of hydrogen, alkyl, alkenyl, alkynyl, cycloalkyl, cycloalkenyl, —$R^{10}$cycloalkyl, —$R^{10}$OH, —$R^{10}(OR^{10})_w$, and —$R^{10}NR^5R^6$;
w is 1-10;
each of $R^5$ and $R^6$ are the same or different and are independently selected from the group consisting of alkyl, cycloalkyl, alkenyl, cycloalkenyl, and alkynyl;
Ay represents an optionally substituted aryl group;
Het represents an optionally substituted 5- or 6-membered heterocyclyl or heteroaryl group;
or a pharmaceutically acceptable salt thereof to a human in need thereof.

2. The method of claim 1 wherein d is 1 and Y is optionally substituted alkylene, said alkylene being optionally substituted with alkyl, dialkyl, or aryl.

3. The method of claim 2 wherein Y is methylene substituted with methyl, dimethyl, or optionally substituted phenyl.

4. The method of claim 1 wherein d is 1 and Y is optionally substituted cycloalkylene.

5. The method of claim 4 wherein Y is indane.

6. The method of claim 1 wherein when Ay is a substituted aryl, said aryl is substituted with alkyl, alkoxy, halogen, haloalkyl, alkylamine, nitro, or cyano.

7. The method of claim 1 wherein p is 1 and $R^1$ is halogen.

8. The method of claim 7 wherein $R^1$ is bromo.

9. The method of claim 1 wherein n is 1.

10. The method of claim 1 wherein X is —NH.

11. The method of claim 1 wherein Z is -Ay.

12. The method of claim 11 wherein -Ay is phenyl or optionally substituted phenyl.

13. The method of claim 1 wherein p is 1, $R^1$ is halogen and substituted para to the depicted N atom, n=1, X is NH, $(Y)_d$ is substituted alkylene, and Z is aryl.

14. The method of claim 13 wherein $R^1$ is bromo or chloro and is substituted para to the depicted N atom, said alkylene is substituted with alkyl, and said aryl is phenyl or optionally substituted phenyl.

15. The method of claim 14 wherein said alkyl is methyl.

16. The method of claim 1 wherein p is 1, $R^1$ is halogen, n is 1, X is NH, $(Y)_d$ is cycloalkylene, and Z is $R^2$.

17. The method of claim 16 wherein $R^1$ is bromo or chloro and is substituted para to the depicted N atom, $(Y)_d$ is indane, and $R^2$ is hydrogen.

18. The method of claim 1 wherein the compound is selected from the group consisting of:
N-Benzyl-2,3,4,9-tetrahydrocarbazole-1-amine hydrochloride salt,
N-(4-Methoxybenzyl)-2,3,4,9-tetrahydro-1H-carbazol-1-amine hydrochloride salt,
N-(2-Phenylethyl)-2,3,4,9-tetrahydro-1H-carbazol-1-amine hydrochloride salt,
N-[(1R)-1-Phenylethyl]-2,3,4,9-tetrahydro-1H-carbazol-1-amine hydrochloride salt,
N-Cyclohexyl-2,3,4,9-tetrahydro-1H-carbazol-1-amine hydrochloride salt,
N-(2,3-Dihydro-1H-inden-2-yl)-2,3,4,9-tetrahydro-1H-carbazol-1-amine hydrochloride salt,
N-Propyl-2,3,4,9-tetrahydro-1H-carbazol-1-amine hydrochloride salt,
N-(2-Methoxyethyl)-2,3,4,9-tetrahydro-1H-carbazol-1-amine hydrochloride salt
(2R)-2-Phenyl-2-(2,3,4,9-tetrahydro-1H-carbazol-1-ylamino)ethanol hydrochloride salt,
N-[(1S)-1-Methyl-3-phenylpropyl]-2,3,4,9-tetrahydro-1H-carbazol-1-aminehydrochloride salt,
N-(1,3-Benzodioxol-5-ylmethyl)-2,3,4,9-tetrahydro-1H-carbazol-1-amine hydrochloride salt,
6-Bromo-N-(2-phenylethyl)-2,3,4,9-tetrahydro-1H-carbazol-1-amine hydrochloride salt,
(1R)-6-Bromo-N-(2,3-dihydro-1H-inden-2-yl)-2,3,4,9-tetrahydro-1H-carbazol-1-amine hydrochloride salt,
(1S)-6-Bromo-N-(2,3-dihydro-1H-inden-2-yl)-2,3,4,9-tetrahydro-1H-carbazol-1-amine hydrochloride salt,
N-Benzyl-6-bromo-2,3,4,9-tetrahydro-1H-carbazol-1-amine hydrochloride salt,
6-Bromo-N-[(1R)-1-phenylethyl]-2,3,4,9-tetrahydro-1H-carbazol-1-amine hydrochloride salt,
(1R)-6-bromo-N-[(1R)-1-phenylethyl]-2,3,4,9-tetrahydro-1H-carbazol-1-amine hydrochloride salt
(1S)-6-Bromo-N-[(1R)-1-phenylethyl]-2,3,4,9-tetrahydro-1H-carbazol-1-amine hydrochloride salt,
6-Bromo-N-(1-methyl-1-phenylethyl)-2,3,4,9-tetrahydro-1H-carbazol-1-amine hydrochloride salt,
6-Bromo-N-[(1S)-1-phenylethyl]-2,3,4,9-tetrahydro-1H-carbazol-1-amine hydrochloride salt,
(1S)-6-Bromo-N-[(1S)-1-phenylethyl]-2,3,4,9-tetrahydro-1H-carbazol-1-amine hydrochloride salt, (1R)-6-Bromo-N-[(1S)-1-phenylethyl]-2,3,4,9-tetrahydro-1H-carbazol-1-amine hydrochloride salt,
6-Bromo-N-methyl-N-(2-phenylethyl)-2,3,4,9-tetrahydro-1H-carbazol-1-amine hydrochloride salt,
6-Bromo-9-methyl-N-(2-phenylethyl)-2,3,4,9-tetrahydro-1H-carbazol-1-amine hydrochloride salt,
6-Bromo-N-[(2R)-2-phenylpropyl]-2,3,4,9-tetrahydro-1H-carbazol-1-amine hydrochloride salt,
6-Methyl-N-(2-phenylethyl)-2,3,4,9-tetrahydro-1H-carbazol-1-amine hydrochloride salt,
N-(2,3-Dihydro-1H-inden-2-yl)-6-methyl-2,3,4,9-tetrahydro-1H-carbazol-1-amine hydrochloride salt,
6-Methyl-N-[(1R)-1-phenylethyl]-2,3,4,9-tetrahydro-1H-carbazol-1-amine hydrochloride salt,
(1R)-6-Methyl-N-[(1R)-1-phenylethyl]-2,3,4,9-tetrahydro-1H-carbazol-1-amine hydrochloride salt,
(1S)-6-Methyl-N-[(1R)-1-phenylethyl]-2,3,4,9-tetrahydro-1H-carbazol-1-amine hydrochloride salt,
6-Methyl-N-[(1S)-1-phenylethyl]-2,3,4,9-tetrahydro-1H-carbazol-1-amine hydrochloride salt,
(1S)-6-Methyl-N-[(1S)-1-phenylethyl]-2,3,4,9-tetrahydro-1H-carbazol-1-amine hydrochloride salt,
(1R)-6-Methyl-N-[(1S)-1-phenylethyl]-2,3,4,9-tetrahydro-1H-carbazol-1-amine hydrochloride salt,
N-Benzyl-6-nitro-2,3,4,9-tetrahydro-1H-carbazol-1-amine hydrochloride salt,
6-Nitro-N-[(1R)-1-phenylethyl]-2,3,4,9-tetrahydro-1H-carbazol-1-amine hydrochloride salt,
7-Bromo-N-(2-phenylethyl)-1,2,3,4-tetrahydrocyclopenta[b]indol-3-amine hydrochloride salt,
(3R)-7-Bromo-N-[(1R)-1-phenylethyl]-1,2,3,4-tetrahydrocyclopenta[b]indol-3-amine hydrochloride salt,
(3S)-7-Bromo-N-[(1R)-1-phenylethyl]-1,2,3,4-tetrahydrocyclopenta[b]indol-3-amine hydrochloride salt,
N-Benzyl-6-methoxy-2,3,4,9-tetrahydro-1H-carbazol-1-amine hydrochloride salt,
N-Benzyl-2-bromo-5,6,7,8,9,10-hexahydrocyclohepta[b]indol-6-amine hydrochloride,
2-Bromo-N-[(1R)-1-phenylethyl]-5,6,7,8,9,10-hexahydrocyclohepta[b]indol-6-amine Hydrochloride,
2-Bromo-N-(2-phenylethyl)-5,6,7,8,9,10-hexahydrocyclohepta[b]indol-6-amine Hydrochloride,
6-Bromo-N-(4-fluorobenzyl)-2,3,4,9-tetrahydro-1H-carbazol-1-amine hydrochloride,
N-Benzyl-6-(trifluoromethyl)-2,3,4,9-tetrahydro-1H-carbazol-1-amine hydrochloride
N-[(1R)-1-Phenylethyl]-6-(trifluoromethyl)-2,3,4,9-tetrahydro-1H-carbazol-1-amine Hydrochloride,
N-Benzhydryl-6-bromo-2,3,4,9-tetrahydro-1H-carbazol-1-amine hydrochloride,
N-Benzyl-7-bromo-2,3,4,9-tetrahydro-1H-carbazol-1-amine hydrochloride,
7-Bromo-N-[(1R)-1-phenylethyl]-2,3,4,9-tetrahydro-1H-carbazol-1-amine Hydrochloride,
7-Bromo-N-(2,3-dihydro-1H-inden-2-yl)-2,3,4,9-tetrahydro-1H-carbazol-1-amine Hydrochloride,
6-Bromo-1-[(phenylmethyl)oxy]-2,3,4,9-tetrahydro-1H-carbazole,
N-(6-Bromo-2,3,4,9-tetrahydro-1H-carbazol-1-yl)-N'-isopropylurea,
Methyl 6-bromo-2,3,4,9-tetrahydro-1H-carbazol-1-ylcarbamate,
N-(6-Bromo-2,3,4,9-tetrahydro-1H-carbazol-1-yl)acetamide,
N-(6-Bromo-2,3,4,9-tetrahydro-1H-carbazol-1-yl)cyclohexanecarboxamide,
N-(6-Bromo-2,3,4,9-tetrahydro-1H-carbazol-1-yl)methanesulfonamide,
N-(6-Bromo-2,3,4,9-tetrahydro-1H-carbazol-1-yl)urea, and
N-Benzyl-8-bromo-2,3,4,9-tetrahydro-1H-carbazol-1-amine hydrochloride.

19. The method of claim 1 wherein the compound is selected from the group consisting of:
N-Benzyl-2,3,4,9-tetrahydrocarbazole-1-amine hydrochloride salt,
N-(4-Methoxybenzyl)-2,3,4,9-tetrahydro-1H-carbazol-1-amine hydrochloride salt,
N-(2-Phenylethyl)-2,3,4,9-tetrahydro-1H-carbazol-1-amine hydrochloride salt,
N-(2,3-Dihydro-1H-inden-2-yl)-2,3,4,9-tetrahydro-1H-carbazol-1-amine hydrochloride salt,
N-[(1S)-1-Methyl-3-phenylpropyl]-2,3,4,9-tetrahydro-1H-carbazol-1-amine hydrochloride salt,
N-(1,3-Benzodioxol-5-ylmethyl)-2,3,4,9-tetrahydro-1H-carbazol-1-amine hydrochloride salt,
6-Bromo-N-(2-phenylethyl)-2,3,4,9-tetrahydro-1H-carbazol-1-amine hydrochloride salt,
(1R)-6-Bromo-N-(2,3-dihydro-1H-inden-2-yl)-2,3,4,9-tetrahydro-1H-carbazol-1-amine hydrochloride salt,
(1S)-6-Bromo-N-(2,3-dihydro-1H-inden-2-yl)-2,3,4,9-tetrahydro-1H-carbazol-1-amine hydrochloride salt,
N-Benzyl-6-bromo-2,3,4,9-tetrahydro-1H-carbazol-1-amine hydrochloride salt,
6-Bromo-N-[(1R)-1-phenylethyl]-2,3,4,9-tetrahydro-1H-carbazol-1-amine hydrochloride salt,
(1R)-6-bromo-N-[(1R)-1-phenylethyl]-2,3,4,9-tetrahydro-1H-carbazol-1-amine hydrochloride salt,
(1S)-6-Bromo-N-[(1R)-1-phenylethyl]-2,3,4,9-tetrahydro-1H-carbazol-1-amine hydrochloride salt,
6-Bromo-N-(1-methyl-1-phenylethyl)-2,3,4,9-tetrahydro-1H-carbazol-1-amine hydrochloride salt,
6-Bromo-N-[(1S)-1-phenylethyl]-2,3,4,9-tetrahydro-1H-carbazol-1-amine hydrochloride salt,
(1S)-6-Bromo-N-[(1S)-1-phenylethyl]-2,3,4,9-tetrahydro-1H-carbazol-1-amine hydrochloride salt,
(1R)-6-Bromo-N-[(1S)-1-phenylethyl]-2,3,4,9-tetrahydro-1H-carbazol-1-amine hydrochloride salt,
6-Bromo-N-methyl-N-(2-phenylethyl)-2,3,4,9-tetrahydro-1H-carbazol-1-amine hydrochloride salt,
6-Bromo-N-[(2R)-2-phenylpropyl]-2,3,4,9-tetrahydro-1H-carbazol-1-amine hydrochloride salt,
6-Methyl-N-(2-phenylethyl)-2,3,4,9-tetrahydro-1H-carbazol-1-amine hydrochloride salt,
N-(2,3-Dihydro-1H-inden-2-yl)-6-methyl-2,3,4,9-tetrahydro-1H-carbazol-1-amine hydrochloride salt,
6-Methyl-N-[(1R)-1-phenylethyl]-2,3,4,9-tetrahydro-1H-carbazol-1-amine hydrochloride salt,
(1R)-6-Methyl-N-[(1R)-1-phenylethyl]-2,3,4,9-tetrahydro-1H-carbazol-1-amine hydrochloride salt,
(1S)-6-Methyl-N-[(1R)-1-phenylethyl]-2,3,4,9-tetrahydro-1H-carbazol-1-amine hydrochloride salt,
6-Methyl-N-[(1S)-1-phenylethyl]-2,3,4,9-tetrahydro-1H-carbazol-1-amine hydrochloride salt,
(1S)-6-Methyl-N-[(1S)-1-phenylethyl]-2,3,4,9-tetrahydro-1H-carbazol-1-amine hydrochloride salt,
(1R)-6-Methyl-N-[(1S)-1-phenylethyl]-2,3,4,9-tetrahydro-1H-carbazol-1-amine hydrochloride salt,
6-Nitro-N-[(1R)-1-phenylethyl]-2,3,4,9-tetrahydro-1H-carbazol-1-amine hydrochloride salt,
(3R)-7-Bromo-N-[(1R)-1-phenylethyl]-1,2,3,4-tetrahydrocyclopenta[b]indol-3-amine hydrochloride salt,
N-Benzyl-6-methoxy-2,3,4,9-tetrahydro-1H-carbazol-1-amine hydrochloride salt,
N-Benzyl-2-bromo-5,6,7,8,9,10-hexahydrocyclohepta[b]indol-6-amine hydrochloride,
2-Bromo-N-[(1R)-1-phenylethyl]-5,6,7,8,9,10-hexahydrocyclohepta[b]indol-6-amine Hydrochloride,
2-Bromo-N-(2-phenylethyl)-5,6,7,8,9,10-hexahydrocyclohepta[b]indol-6-amine Hydrochloride, 6-Bromo-N-(4-fluorobenzyl)-2,3,4,9-tetrahydro-1H-carbazol-1-amine hydrochloride,
N-Benzyl-6-(trifluoromethyl)-2,3,4,9-tetrahydro-1H-carbazol-1-amine hydrochloride,
N-[(1R)-1-Phenylethyl]-6-(trifluoromethyl)-2,3,4,9-tetrahydro-1H-carbazol-1-amine Hydrochloride,
N-Benzhydryl-6-bromo-2,3,4,9-tetrahydro-1H-carbazol-1-amine hydrochloride,
7-Bromo-N-[(1R)-1-phenylethyl]-2,3,4,9-tetrahydro-1H-carbazol-1-amine Hydrochloride,
7-Bromo-N-(2,3-dihydro-1H-inden-2-yl)-2,3,4,9-tetrahydro-1H-carbazol-1-amine Hydrochloride,
6-Bromo-1-[(phenylmethyl)oxy]-2,3,4,9-tetrahydro-1H-carbazole,
N-(6-Bromo-2,3,4,9-tetrahydro-1H-carbazol-1-yl)-N'-isopropylurea,
Methyl 6-bromo-2,3,4,9-tetrahydro-1H-carbazol-1-ylcarbamate,
N-(6-Bromo-2,3,4,9-tetrahydro-1H-carbazol-1-yl)cyclohexanecarboxamide,
N-(6-Bromo-2,3,4,9-tetrahydro-1H-carbazol-1-yl)methanesulfonamide, and
N-(6-Bromo-2,3,4,9-tetrahydro-1H-carbazol-1-yl)urea.

20. The method of claim 1 wherein the compound is selected from the group consisting of:
N-(4-Methoxybenzyl)-2,3,4,9-tetrahydro-1H-carbazol-1-amine hydrochloride salt,
N-(1,3-Benzodioxol-5-ylmethyl)-2,3,4,9-tetrahydro-1H-carbazol-1-amine hydrochloride salt,
6-Bromo-N-(2-phenylethyl)-2,3,4,9-tetrahydro-1H-carbazol-1-amine hydrochloride salt,
(1R)-6-Bromo-N-(2,3-dihydro-1H-inden-2-yl)-2,3,4,9-tetrahydro-1H-carbazol-1-amine hydrochloride salt,
(1S)-6-Bromo-N-(2,3-dihydro-1H-inden-2-yl)-2,3,4,9-tetrahydro-1H-carbazol-1-amine hydrochloride salt,
N-Benzyl-6-bromo-2,3,4,9-tetrahydro-1H-carbazol-1-amine hydrochloride salt,
6-Bromo-N-[(1R)-1-phenylethyl]-2,3,4,9-tetrahydro-1H-carbazol-1-amine hydrochloride salt,
(1R)-6-bromo-N-[(1R)-1-phenylethyl]-2,3,4,9-tetrahydro-1H-carbazol-1-amine hydrochloride salt,
(1S)-6-Bromo-N-[(1R)-1-phenylethyl]-2,3,4,9-tetrahydro-1H-carbazol-1-amine hydrochloride salt,
6-Bromo-N-(1-methyl-1-phenylethyl)-2,3,4,9-tetrahydro-1H-carbazol-1-amine hydrochloride salt,
6-Bromo-N-[(1S)-1-phenylethyl]-2,3,4,9-tetrahydro-1H-carbazol-1-amine hydrochloride salt,
(1S)-6-Bromo-N-[(1S)-1-phenylethyl]-2,3,4,9-tetrahydro-1H-carbazol-1-amine hydrochloride salt,
(1R)-6-Bromo-N-[(1S)-1-phenylethyl]-2,3,4,9-tetrahydro-1H-carbazol-1-amine hydrochloride salt,
6-Bromo-N-methyl-N-(2-phenylethyl)-2,3,4,9-tetrahydro-1H-carbazol-1-amine hydrochloride salt,
6-Bromo-N-[(2R)-2-phenylpropyl]-2,3,4,9-tetrahydro-1H-carbazol-1-amine hydrochloride salt,
6-Methyl-N-(2-phenylethyl)-2,3,4,9-tetrahydro-1H-carbazol-1-amine hydrochloride salt,
N-(2,3-Dihydro-1H-inden-2-yl)-6-methyl-2,3,4,9-tetrahydro-1H-carbazol-1-amine hydrochloride salt,
6-Methyl-N-[(1R)-1-phenylethyl]-2,3,4,9-tetrahydro-1H-carbazol-1-amine hydrochloride salt,
(1R)-6-Methyl-N-[(1R)-1-phenylethyl]-2,3,4,9-tetrahydro-1H-carbazol-1-amine hydrochloride salt,
(1R)-6-Methyl-N-[(1S)-1-phenylethyl]-2,3,4,9-tetrahydro-1H-carbazol-1-amine hydrochloride salt,
6-Nitro-N-[(1R)-1-phenylethyl]-2,3,4,9-tetrahydro-1H-carbazol-1-amine hydrochloride salt,
(3R)-7-Bromo-N-[(1R)-1-phenylethyl]-1,2,3,4-tetrahydrocyclopenta[b]indol-3-amine hydrochloride salt,
N-Benzyl-2-bromo-5,6,7,8,9,10-hexahydrocyclohepta[b]indol-6-amine hydrochloride,
2-Bromo-N-[(1R)-1-phenylethyl]-5,6,7,8,9,10-hexahydrocyclohepta[b]indol-6-amine hydrochloride,
2-Bromo-N-(2-phenylethyl)-5,6,7,8,9,10-hexahydrocyclohepta[b]indol-6-amine hydrochloride,
6-Bromo-N-(4-fluorobenzyl)-2,3,4,9-tetrahydro-1H-carbazol-1-amine hydrochloride,
N-Benzyl-6-(trifluoromethyl)-2,3,4,9-tetrahydro-1H-carbazol-1-amine hydrochloride,
N-[(1R)-1-Phenylethyl]-6-(trifluoromethyl)-2,3,4,9-tetrahydro-1H-carbazol-1-amine hydrochloride,
N-Benzhydryl-6-bromo-2,3,4,9-tetrahydro-1H-carbazol-1-amine hydrochloride,
7-Bromo-N-[(1R)-1-phenylethyl]-2,3,4,9-tetrahydro-1H-carbazol-1-amine hydrochloride,
7-Bromo-N-(2,3-dihydro-1H-inden-2-yl)-2,3,4,9-tetrahydro-1H-carbazol-1-amine hydrochloride,
6-Bromo-1-[(phenylmethyl)oxy]-2,3,4,9-tetrahydro-1H-carbazole,
N-(6-Bromo-2,3,4,9-tetrahydro-1H-carbazol-1-yl)-N'-isopropylurea,
Methyl 6-bromo-2,3,4,9-tetrahydro-1H-carbazol-1-ylcarbamate,
N-(6-Bromo-2,3,4,9-tetrahydro-1H-carbazol-1-yl)cyclohexanecarboxamide, and
N-(6-Bromo-2,3,4,9-tetrahydro-1H-carbazol-1-yl)methanesulfonamide.

21. The method of claim 1 wherein the compound of claim 1 further comprises:

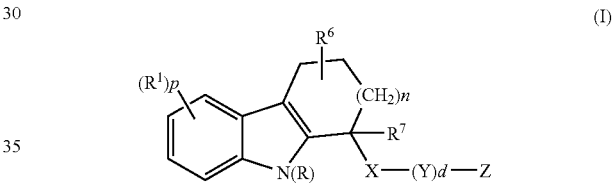

(I)

wherein $R^6$ is H, alkyl, —$OR^2$, —$NR^2R^3$, Ay, Het, —C(O)$R^2$, —$CO_2R^2$, —$CONR^2R^3$, —$S(O)_mR^2$, or oxo, where $R^2$, $R^3$, m, Ay, and Het are as defined; and
$R^7$ is H or alkyl;
provided $R^6$ and $R^7$ are not both H.

22. A compound selected from

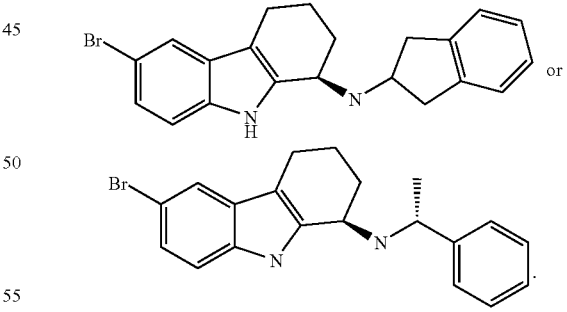

23. A method for the treatment of HPV infection comprising the administration of a compound of formula (I) as defined in claim 1.

24. A method for the treatment of HPV infection, genital warts, or cervical dysplasia comprising the administration of a compound of claim 22.

25. A method for the treatment of HPV infection comprising the administration of a compound of claim 22.

* * * * *